US012807576B2

(12) United States Patent
Oniciu et al.

(10) Patent No.: US 12,807,576 B2
(45) Date of Patent: Nov. 24, 2026

(54) PHENTOLAMINE MESYLATE AND THERAPEUTIC USES THEREOF

(71) Applicant: Opus Genetics, Inc., Farmington Hills, MI (US)

(72) Inventors: Daniela Carmen Oniciu, Gainesville, FL (US); Rosa Maria Espinosa Ferrer, Barcelona (ES)

(73) Assignee: Opus Genetics, Inc., Durham, NC (US)

( * ) Notice: Subject to any disclaimer, the term of this patent is extended or adjusted under 35 U.S.C. 154(b) by 424 days.

(21) Appl. No.: 18/587,397

(22) Filed: Feb. 26, 2024

(65) Prior Publication Data

US 2025/0162995 A1 May 22, 2025

(30) Foreign Application Priority Data

Nov. 21, 2023 (EP) .................................... 23383186

(51) Int. Cl.
*C07D 233/24* (2006.01)
*A61K 9/00* (2006.01)
(Continued)

(52) U.S. Cl.
CPC .......... *C07D 233/24* (2013.01); *A61K 9/0048* (2013.01); *A61K 9/08* (2013.01); *A61K 31/417* (2013.01)

(58) Field of Classification Search
CPC ...... C07D 233/24; A61K 9/0048; A61K 9/08; A61K 31/417
See application file for complete search history.

(56) References Cited

U.S. PATENT DOCUMENTS 4,252,721 A 2/1981 Silvestrini et al.
4,443,441 A 4/1984 Galin
(Continued)

FOREIGN PATENT DOCUMENTS

CN 101402579 A 4/2009
CN 101463009 A 6/2009
(Continued)

OTHER PUBLICATIONS

Phentolamine mesylate (United States Pharmacopeia (USP) Reference Standard), Sigma-Aldrich, Inc. (Product No. 1530004). Last SDS revision dated Aug. 8, 2024 (Retrieved from the internet on May 24, 2024 from URL: https://www.sigmaaldrich.com/US/en/product/usp/1530004). Prior SDS revision dated Aug. 4, 2021.
(Continued)

*Primary Examiner* — Brandon J Fetterolf
(74) *Attorney, Agent, or Firm* — Morgan, Lewis & Bockius LLP

(57) ABSTRACT

This invention provides phentolamine mesylate that exhibits a particular x-ray powder diffraction (XRPD) pattern or exhibits one or more particular XRPD peaks. The invention also provides compositions comprising the phentolamine mesylate and compositions in which the phentolamine mesylate is dissolved. The invention also provides methods for treating or preventing an ocular disease or condition, comprising administering to a subject in need thereof an effective amount of the phentolamine mesylate, a composition comprising the phentolamine mesylate or a composition in which the phentolamine mesylate is dissolved.

38 Claims, 26 Drawing Sheets

(51) Int. Cl.
*A61K 9/08* (2006.01)
*A61K 31/417* (2006.01)

(56) References Cited

U.S. PATENT DOCUMENTS

| | | | |
|---|---|---|---|
| 4,508,715 | A | 4/1985 | Booth et al. |
| 4,515,295 | A | 5/1985 | Dougherty |
| 4,590,202 | A | 5/1986 | Remy |
| 4,629,456 | A | 12/1986 | Edwards |
| 4,659,714 | A | 4/1987 | Watt-Smith |
| 4,834,727 | A | 5/1989 | Cope |
| 4,888,344 | A | 12/1989 | Sunagawa et al. |
| 4,906,613 | A | 3/1990 | Watkins |
| 4,938,970 | A | 7/1990 | Hustead et al. |
| 5,032,392 | A | 7/1991 | Varma |
| 5,059,188 | A | 10/1991 | Goddard |
| 5,134,124 | A | 7/1992 | Nisato et al. |
| 5,149,320 | A | 9/1992 | Dhaliwal et al. |
| 5,192,527 | A | 3/1993 | Abrahmsohn |
| 5,261,903 | A | 11/1993 | Dhaliwal et al. |
| 5,281,591 | A | 1/1994 | Burke |
| 5,288,759 | A | 2/1994 | DeSantis, Jr. |
| 5,488,050 | A | 1/1996 | Neufeld |
| 5,514,118 | A | 5/1996 | Kummer et al. |
| 5,584,823 | A | 12/1996 | Valberg |
| 5,591,426 | A | 1/1997 | Dabrowski et al. |
| 5,605,896 | A | 2/1997 | Leonardi et al. |
| 5,627,611 | A | 5/1997 | Scheiner |
| 5,731,339 | A | 3/1998 | Lowrey |
| 5,792,767 | A | 8/1998 | Meyer et al. |
| 5,885,550 | A | 3/1999 | Vallier |
| 5,891,882 | A | 4/1999 | Meyer et al. |
| 5,891,913 | A | 4/1999 | Sallmann et al. |
| 5,895,654 | A | 4/1999 | Hartford et al. |
| 6,001,845 | A | 12/1999 | Estok |
| 6,025,396 | A | 2/2000 | Kim et al. |
| 6,043,224 | A | 3/2000 | Lee et al. |
| 6,046,207 | A | 4/2000 | Meyer et al. |
| 6,051,594 | A | 4/2000 | Lowrey |
| 6,106,866 | A | 8/2000 | Ranney |
| 6,124,461 | A | 9/2000 | Shoemaker |
| 6,291,498 | B1 | 9/2001 | Horn |
| 6,420,407 | B1 | 7/2002 | Horn |
| 6,432,401 | B2 | 8/2002 | Weber et al. |
| 6,469,065 | B1 | 10/2002 | Garvey et al. |
| 6,515,006 | B2 | 2/2003 | Horn |
| 6,638,537 | B2 | 10/2003 | Dennis et al. |
| 6,730,065 | B1 | 5/2004 | Horn |
| 6,730,691 | B1 | 5/2004 | Galin |
| 6,764,678 | B2 | 7/2004 | Weber et al. |
| 6,872,390 | B2 | 3/2005 | Weber et al. |
| 7,229,630 | B2 | 6/2007 | Chen et al. |
| 7,569,230 | B2 | 8/2009 | Chen et al. |
| 7,575,757 | B2 | 8/2009 | Chen et al. |
| 7,868,035 | B2 | 1/2011 | Woodward et al. |
| 8,299,079 | B2 | 10/2012 | Kaufman |
| 8,445,526 | B2 | 5/2013 | Horn |
| 8,580,787 | B2 | 11/2013 | Horn |
| 8,597,629 | B1 | 12/2013 | Horn |
| 8,889,112 | B2 | 11/2014 | Horn |
| 8,979,809 | B2 | 3/2015 | Horn |
| 9,066,856 | B2 | 6/2015 | Demopulos et al. |
| 9,089,560 | B2 | 7/2015 | Meyer |
| 9,789,088 | B2 | 10/2017 | Meyer |
| 9,795,560 | B2 | 10/2017 | Meyer |
| 9,968,594 | B2 | 5/2018 | Horn et al. |
| 10,064,818 | B2 | 9/2018 | Horn et al. |
| 10,278,918 | B2 | 5/2019 | Meyer |
| 10,507,245 | B2 | 12/2019 | Vejarano Restrepo |
| 10,610,518 | B2 | 4/2020 | Robinson et al. |
| 10,639,297 | B2 | 5/2020 | Feinbaum et al. |
| 10,772,829 | B2 | 9/2020 | Meyer |
| 10,993,932 | B2 | 5/2021 | Pitlick et al. |
| 11,000,509 | B2 | 5/2021 | Meyer |
| 11,090,261 | B2 | 8/2021 | Meyer |
| 11,400,077 | B2 | 8/2022 | Pitlick et al. |
| 11,566,005 | B2 | 1/2023 | Oniciu |
| 11,717,510 | B2 | 8/2023 | Meyer |
| 11,844,858 | B2 | 12/2023 | Meyer |
| 11,976,044 | B2 | 5/2024 | Oniciu |
| 2002/0082288 | A1 | 6/2002 | Horn |
| 2002/0183356 | A1 | 12/2002 | Weber et al. |
| 2002/0183396 | A1 | 12/2002 | Weber et al. |
| 2002/0187986 | A1 | 12/2002 | Horn |
| 2003/0236306 | A1 | 12/2003 | Chen et al. |
| 2004/0053894 | A1 | 3/2004 | Mazess et al. |
| 2004/0176408 | A1 | 9/2004 | Horn |
| 2005/0080056 | A1 | 4/2005 | Horn |
| 2005/0203099 | A1 | 9/2005 | Chen et al. |
| 2006/0211753 | A1 | 9/2006 | Horn |
| 2006/0257388 | A1 | 11/2006 | Knowles |
| 2007/0098748 | A1 | 5/2007 | Chen et al. |
| 2008/0020076 | A1 | 1/2008 | Jhamandas et al. |
| 2008/0039507 | A1 | 2/2008 | Woodward et al. |
| 2009/0131303 | A1 | 5/2009 | Hong et al. |
| 2009/0220618 | A1 | 9/2009 | Xia et al. |
| 2009/0232763 | A1 | 9/2009 | Kabra et al. |
| 2010/0029663 | A1 | 2/2010 | Horn |
| 2010/0324031 | A1 | 12/2010 | Kabra |
| 2011/0152274 | A1 | 6/2011 | Kaufman |
| 2011/0178147 | A1 | 7/2011 | Likitlersuang et al. |
| 2012/0136072 | A1 | 5/2012 | Mosher et al. |
| 2012/0149748 | A1 | 6/2012 | Shanler et al. |
| 2012/0208858 | A1 | 8/2012 | Shanler et al. |
| 2012/0238615 | A1 | 9/2012 | Chow et al. |
| 2012/0277239 | A1 | 11/2012 | Horn et al. |
| 2013/0029919 | A1 | 1/2013 | Gore et al. |
| 2013/0143938 | A1 | 6/2013 | Horn |
| 2013/0172357 | A1 | 7/2013 | Horn |
| 2014/0221445 | A1 | 8/2014 | Meyer |
| 2014/0221446 | A1 | 8/2014 | Meyer |
| 2015/0150848 | A1 | 6/2015 | Horn |
| 2016/0008278 | A1 | 1/2016 | Horn et al. |
| 2016/0008337 | A1 | 1/2016 | Horn et al. |
| 2016/0051515 | A1 | 2/2016 | Meyer |
| 2017/0029365 | A1 | 2/2017 | Giordano et al. |
| 2017/0065664 | A1 | 3/2017 | Russ |
| 2017/0137453 | A1 | 5/2017 | Albrecht et al. |
| 2018/0221274 | A1 | 8/2018 | Meyer |
| 2018/0221340 | A1 | 8/2018 | Meyer |
| 2019/0248760 | A1 | 8/2019 | Liu et al. |
| 2019/0254963 | A1 | 8/2019 | Meyer |
| 2019/0321337 | A1 | 10/2019 | Robinson et al. |
| 2019/0358152 | A1 | 11/2019 | Meyer |
| 2020/0246310 | A1 | 8/2020 | Pitlick et al. |
| 2020/0253931 | A1 | 8/2020 | Pitlick et al. |
| 2022/0388965 | A1 | 12/2022 | Oniciu |
| 2023/0146674 | A1 | 5/2023 | Oniciu |

FOREIGN PATENT DOCUMENTS

| | | | |
|---|---|---|---|
| CN | 102813631 | A | 12/2012 |
| CN | 102858330 | A | 1/2013 |
| CN | 103408495 | * | 11/2013 |
| CN | 103408495 | A | 11/2013 |
| WO | WO-9505188 | A1 | 2/1995 |
| WO | WO-1999007353 | A1 | 2/1999 |
| WO | WO-1999065475 | A2 | 12/1999 |
| WO | WO-2001019364 | A1 | 3/2001 |
| WO | WO-2001085171 | A1 | 11/2001 |
| WO | WO-2003013515 | A1 | 2/2003 |
| WO | WO-2004000219 | A2 | 12/2003 |
| WO | WO-2005025570 | A1 | 3/2005 |
| WO | WO-2005123093 | A2 | 12/2005 |
| WO | WO-2007008666 | A2 | 1/2007 |
| WO | WO-2009077736 | A2 | 6/2009 |
| WO | WO-2010135731 | A1 | 11/2010 |
| WO | WO-2011050018 | A1 | 4/2011 |
| WO | WO-2011050030 | A1 | 4/2011 |
| WO | WO-2012075319 | A2 | 6/2012 |
| WO | WO-2012112566 | A1 | 8/2012 |
| WO | WO-2012119059 | A1 | 9/2012 |
| WO | WO-2012119070 | A2 | 9/2012 |
| WO | WO-2013115844 | A1 | 8/2013 |

(56) References Cited

FOREIGN PATENT DOCUMENTS

| | | | |
|---|---|---|---|
| WO | WO-2013130577 | A2 | 9/2013 |
| WO | WO-2013169315 | A1 | 11/2013 |
| WO | WO-2014121027 | A1 | 8/2014 |
| WO | WO-2014121028 | A1 | 8/2014 |
| WO | WO-2018033792 | A2 | 2/2018 |
| WO | WO-2020081562 | A1 | 4/2020 |
| WO | WO-2020087021 | A1 | 4/2020 |
| WO | WO-2021050980 | A1 | 3/2021 |
| WO | WO2022245964 | A1 * | 11/2022 |

OTHER PUBLICATIONS

International Search Report and Written Opinion for International Application No. PCT/US2024/056856, dated Feb. 19, 2025 (15 pages).

Abad et al. "Comparison of Astigmatism Correction Using Shorter Arc Length 90° / 120° Asymmetric Intacs Severe Keratoconus Versus 150° Single-Segment Intacs Severe Keratoconus in Asymmetric Keratoconus," Cornea. Nov. 1, 2011;30(11):1201-6.

Abdelkader et al. "Clinical outcomes of combined versus separate carbachol and brimonidine drops in correcting presbyopia," Eye and vision. Dec. 2016;3:1-6.

Abelson et al., "The Truth about Tachyphylaxis," Review of Ophthalmology. 2006;4(3):112-115.

ACETADOTE® (acetylcysteine) Prescribing Information/ Package Insert / Label, Approval 2004, Revised 2008, Manufactured for Cumberland Pharmaceuticals Inc., Nashville, TN, 7 pages.

Ackerman et al. "Low-dose brimonidine for relief of ocular redness: Integrated analysis of four clinical trials," Clinical and Experimental Optometry. Mar. 1, 2019;102(2):131-9.

ACULAR® Prescribing Information/ Package Insert / Label, 2012, Allergan, Inc., Palo Alto, CA, USA, Reference ID: 72379US10, 6 pages.

Akutsu et al. "Contrast Sensitivity and Reading Through Multifocal Intraocular Lenses," Archives of Ophthalmology. 1992; 1:110(8):1076-1080.

Alió et al. "Management of Complications in Refractive Surgery," Springer, 2nd Edition, 2018, 415 pages.

Al-Khersan et al. "Retinal Detachments Associated with Topical Pilocarpine Use for Presbyopia," American Journal of Ophthalmology. 2022, vol. 242, p. 52-55.

Amarikwa et al. "Vitreofoveal Traction Associated with Pilocarpine for Presbyopia," Ophthalmic Surg Lasers Imaging Retina. 2022; 53(7):410-411.

American Optometric Association, (2020) "Adult Vision: 41 to 60 Years of Age", [online]. Retrieved from the Internet URL: https://www.aoa.org/patients-and-public/good-vision-throughout-life/adult-vision-19-to-40-years-of-age/adult-vision-41-to-60-years-of-age, 5 pages.

American Society of Health-System Pharmacists; AHFS Drug Information 2010. Bethesda, MD. (2010), 4 pages.

Anastasi et al. "Effect of Pilocarpine in Counteracting Mydriasis," Archives of Ophthalmology. 1968;79(6): 710-715.

Antonelli-Incalzi et al. "Respiratory effects of beta-adrenergic receptor blockers," Current Medicinal Chemistry. 2007;14(10): 1121-1128.

Applegate et al. "Metrics of retinal image quality predict visual performance in eyes with 20/17 or better visual acuity," Optometry and Vision Science. 2006; 83(9):635-640.

Asa, "K-max Plus", Technical Attributes and Typical Analysis, retrieved from http://califasainc.com/pdf/Kmax_Analysis.pdf on May 29, 2016, 1 page.

Author Unknown, D-mannitol Safety Data Sheet by Columbus Chemical Industries Inc. (CCI), revised on Jul. 30, 2012. Generic Names: Mannite; Manufacturer: Columbus Chemical Industries, Inc., 5 pages.

Author Unknown, Glycerol (Glycerin, Anhydrous, ACS) Safety Data Sheet by Columbus Chemical Industries Inc. (CCI) (year 2012), Generic Names: 1,2,3-Propanetriol; Glycerol; Manufacturer: Columbus Chemical Industries, Inc., 6 pages.

Author Unknown "Phentolamine Mesylate," MOLBASE [online], CAS No. 65-28-1. Last Updated: Oct. 31, 2016 [retrieved on Jul. 7, 2022]. Retrieved from the Internet. Retrieved from the Internet URL: https://www.molbase.com/en/65-281_supplier-316642_product-41562822.html, 2 pages.

Barbee and Smith "A Comparative Study of Mydriatic and Cycloplegic Agents: in Human Subjects Without Eye Disease," American Journal of Ophthalmology. Nov. 1, 1957;44(5):617-622.

Batawi et al. "Adie's tonic pupil presenting with unilateral photophobia successfully treated with dilute pilocarpine," BMJ Case Reports CP. 2020;13(1):e233136 (3 pages).

Bellucci et al. "Visual acuity and contrast sensitivity comparison between Tecnis and AcrySof AS60AT intraocular lenses", Journal of Cataract & Refractive Surgery, Apr. 1, 2005;31(4):712-717.

Benson et al., "Is Phentolamine Stable in Solution with Papaverine," The Journal of Urology. 1988, vol. 140, p. 970-971.

Besada et al. "Pupillometry Study of Brimonidine Tartrate 0.2% and Apraclonidine 0.5%", The Journal of Clinical Pharmacology, 2011; 51(12):1690-1695.

BETAGAN® Prescribing Information / Package Insert / Label, NDA 19219/S-029, Revised Nov. 2017, Allergan, Inc., Palo Alto, CA, USA, Reference ID: 4198172, 8 pages.

Betoptic (Betaxol Hydrochloride Ophthalmic Solution), Pilo PI 2006, Prescribing Information / Package Insert / Label, NDA 19-270/S-031, 5 pages.

Bidgoli et al. "Night Vision Disturbances Following Refractive Surgery: Causes, Prevention, and Treatment," Management of Complications in Refractive Surgery. 2018:163-74.

European Glaucoma Society. European Glaucoma Society Terminology and Guidelines for Glaucoma,—Chapter 3: Treatment principles and options. Supported by the EGS Foundation: Part 1: Foreword; Introduction; Glossary; Chapter 3 Treatment principles and options. Br J Ophthalmol. 2017;101(6):130-95.

Boger et al. "Clinical Trial Comparing Timolol Ophthalmic Solution to Pilocarpine in Open-Angle Glaucoma," American Journal of Ophthalmology, 1978, 86(1):8-18. https://doi.org/10.1016/0002-9394(78)90006-5.

Boland et al. "Electronic monitoring to assess adherence with once-daily glaucoma medications and risk factors for nonadherence: the automated dosing reminder study," JAMA ophthalmology. Jul. 1, 2014;132(7):838-844.

Boyer et al. "Phentolamine Ophthalmic Solution Rapidly Reverses Pharmacologically Induced Mydriasis in Two Pivotal Phase 3 MIRA Trials," ASRS Annual Meeting. 2002, Abstract ID 665511, 10 pages.

Bradley et al. "International Harmonization of Nomenclature and Diagnostic Criteria (INHAND): Nonproliferative and Proliferative Lesions of the Rabbit," Journal of Toxicologic Pathology. 2021; 34 (3_Suppl. 2021-I001), 183S-292S.

Brooks et al. "Patient subjective visual function after corneal collagen crosslinking for keratoconus and corneal ectasia," Journal of Cataract & Refractive Surgery. 2012; 38(4), 615-619.

Bruner et al. "Spontaneous hibernomas in Sprague-Dawley rats," Toxicologic Pathology. 2009;37(4), 547-552.

Brunton et al. "Goodman & Gilman's Pharmacological Basis of Therapeutics, 12th Edition," McGraw-Hill Education/Medical. 2011, p. 308-310.

Büscher et al. "Comparison of guinea-pig, bovine and rat alpha 1-adrenoceptor subtypes," British journal of pharmacology, 1996;117(4):703-711.

Cankurtaran et al. "Effects of a Single Dose of Topical Brimonidine 0.15% on Anterior Segment Morphology, Pupil Characteristics, and Choroidal Thickness in Healthy Subjects,", Eye & Contact Lens: Science & Clinical Practice. 2021; 47(6), 323-329.

Canovetti et al. "Aceclidine, brimonidine tartrate, and dapiprazole: Comparison of miotic effect and tolerability under different lighting conditions," Journal of Cataract and Refractive Surgery. 2009; 35(1), 42-46.

CDRH/FDA, Summary of Safety and Effectiveness of VISX STAR Excimer Laser System, Premarket Approval Application No. P930016/S025, 2007, 9 pages.

(56) References Cited

OTHER PUBLICATIONS

Chu et al., "The Safety of Phentolamine Ophthalmic Solution for Reversal of Pharmacologically Induced Mydriasis from Multiple Late-Stage Clinical Trials," ASCRS Annual Meeting; 2022; Paper ID 80618, 10 pages.
Chylak et al. "Loss of contrast sensitivity in diabetic patients with LOCSII classified cataracts," British Journal of Ophthalmology. 1993; 77(1):7-11.
CLARINEX® (desloratadine) Prescribing Information/ Package Insert / Label, Initial US Approval 2001, Revised Nov. 2015, Manufactured by Bayer, Inc. 10 pages.
Cohen et al. "The Diagnosis of Adie's Pupil Using 0.0625% Pilocarpine Solution," American Journal of Ophthalmology. May 1, 1975;79(5):883-5.
Co-pending U.S. Appl. No. 18/619,535, inventor Oniciu; Daniela Carmen, filed Mar. 28, 2024.
Cskay et al. "Report from the NEI/FDA ophthalmic clinical trial design and endpoints symposium," Investigative ophthalmology & visual science. Feb. 1, 2008;49(2):479-89.
Dart R.C. (editor). Medical Toxicology. Third Edition, Lippincott Williams & Wilkins. Philadelphia, PA (2004); Chapter 124 Rauwolfia Alkaloids and Chapter 125 Vasolidators, p. 711-722.
De La Torre, JC. "Impaired Cerebromicrovascular Perfusion Summary of Evidence in Support of Its Causality in Alzheimer's Disease," Annals of the New York Academy of Sciences. Dec. 2000;924(1):136-152.
Degraff et al. "Phentolamine," American Heart Journal. Sep. 1, 1976;92(3):397-402.
Devries et al. "Phentolamine Ophthalmic Solution Reverses Pharmacologically Induced Mydriasis in Healthy Subjects: Subgroup Analyses in the Pivotal Phase 3 MIRA-2 Randomized Placebo Controlled Trial," ARVO Annual Meeting, 2022, Abstract ID 3709630, 1 page.
Dexl et al. "Reading performance after implantation of a small-aperture corneal inlay for the surgical correction of presbyopia: Two-year follow-up," Journal of Cataract & Refractive Surgery, 2011, 37(3), pp. 525-531.
Dick et al. "Contrast sensitivity after implantation of toric iris-claw lenses in phakic eyes." Journal of Cataract & Refractive Surgery. Nov. 1, 2004;30(11):2284-2289.
Diestelhorst et al. "Combined Therapy of Pilocarpine or Latanoprost with Timolol Versus Latanoprost Monotherapy," Survey of ophthalmology. Aug. 1, 2002;47:S155-S161.
Dinsmore et al. "Vasoactive intestinal polypeptide and phentolamine mesylate administered by autoinjector in the treatment of patients with erectile dysfunction resistant to other intracavernosal agents," British journal of urology. Mar. 1998;81(3):437-40.
Dinsmore et al. "Vasoactive intestinal polypeptide/phentolamine for intracavernosal injection in erectile dysfunction," BJU Int, 2008; 102:933-937.
Doughtry et al. "A Review of the Clinical Pharmacokinetics of Pilocarpine, Moxisylyte (Thymoxamine), and Dapiprazole in the Reversal of Diagnostic Pupillary Dilation," Optometry and Vision Science. May 1, 1992;69(5):358-368.
Dragoi, V. "Ocular Motor System," Neuroscience Online: An Electronic Textbook for the Neurosciences (2020). The University of Texas Health Science Center at Houston, 15 pages.
Draize et al. "Methods for the study of irritation and toxicity of substances applied topically to the skin and mucous membranes," J Pharmacol Exp Ther (1944) 82:377-390.
Draize, JH. "Appraisal of the Safety of Chemicals in Foods, Drugs and Cosmetics," The Association of Food and Drug Officials of the United States; (1955):49-51.
Drews-Bankiewicz et al. "Contrast Sensitivity in Patients with Nuclear Cataracts," Archives of Ophthalmology. Jul. 1, 1992;110(7):953-959.
Drugbank Online "Phentolamine," DrugBank Accession No. DB0692, 9 pages, [retrieved on Aug. 25, 2022]. Retrieved from the Internet URL: https://go.drugbank.com/drugs/DB00692.
Drum et al. "Assessment of visual performance in the evaluation of new medical products," Drug Discoveries Today: Technologies. 2007; 4(2) 55-61.
Drummond, P. D. "The Effect of Light Intensity and Dose of Dilute Pilocarpine Eyedrops on Pupillary Constriction in Healthy Subjects," American journal of ophthalmology. Aug. 1, 1991;112(2):195-199.
Du et al. "Cell membrane chromatography competitive binding analysis for characterization of α1A adrenoreceptor binding interactions," Analytical and Bioanalytical Chemistry. Jul. 2011; 400:3625-3633.
Dungan et al. "Amidephrine-I: Pharmacologic Characterization of a Sympathomimetic Alkylsulfonamidophenethanolamine," International Journal of Neuropharmacology. Jul. 1, 1965;4(4):219-234.
Durand-Cavagna et al. "Spontaneous pre-Descemet's membrane corneal opacities in rabbits," Laboratory Animal Science. 1998;48(3):310-313.
Edgar et al. "Effects of dipivefrin and pilocarpine on pupil diameter, automated perimetry and Log MAR acuity, " Graefe's Archive for Clinical and Experimental Ophthalmology. Jan. 1999;237:117-124.
El Deeb et al. "Evaluation of monolithic C18 HPLC columns for the fast analysis of pilocarpine hydrochloride in the presence of its degradation products," Die Pharmazie—An International Journal of Pharmaceutical Sciences. Sep. 1, 2006;61(9):751-756.
Elliott et al. "Improvements in clinical and functional vision and perceived visual disability after first and second eye cataract surgery," British Journal of Ophthalmology. Oct. 1, 1997;81(10):889-895.
Elliott et al. "The reliability of the Pelli-Robson chart," Ophthalmic and Physiological Optics. Jan. 1990; 10(1):21-24.
Enroth-Cugell et al. "The contrast sensitivity of retinal ganglion cells of the cat," The Journal of Physiology. Dec. 1, 1966;187(3):517-552.
European Search Report for EP Application No. 14746208.9, dated Jun. 21, 2016, 6 pages.
European Search Report for EP Application No. 23383186.6, dated May 22, 2024, 8 pages.
Eydelman et al. "Symptoms and Satisfaction of Patients in the Patient-Reported Outcomes with Laser In Situ Keratomileusis (PROWL) Studies," JAMA ophthalmology. Jan. 1, 2017;135(1):13-22.
Fan et al. "Improved high-performance liquid chromatographic determination of pilocarpine and its degradation products in ophthalmic solutions importance of octadecylsilane column choice," Journal of Chromatography A. 1996;740(2):289-295.
Fan-Paul et al. "Night vision disturbances after corneal refractive surgery," Survey of Ophthalmology. Nov. 1, 2002;47(6):533-546.
FDA Center for Drug Evaluation and Research, Clinical Pharmacology and Biopharmaceutics Review(s), Summary Basis of Approval (SBA) for Application No. 22-159, OraVerse, 73 pages, date unknown. https://www.accessdata.fda.gov/drugsatfda_docs/nda/2008/022159s000_ClinPharmR.Pdf.
Fejer et al. "Night myopia: implications for the young driver," Canadian journal of ophthalmology. Journal canadien d'ophtalmologie. Jun. 1, 1992;27(4):172-176. Retrieved from https://www.ncbi.nlm.nih.gov/pubmed/1633588.
Foster et al. "MIRA-4, Clinical Trial Evaluating the Safety and Efficacy of Phentolamine Ophthalmic Solution for Reversal of Pharmacologically Induced Mydriasis in Pediatric Subjects Aged 3-11 Years," AAOpt Annual Meeting, Abstract ID 10569, 1 page.
Fricke et al. "Global prevalence of presbyopia and vision impairment from uncorrected presbyopia: systematic review, meta-analysis, and modelling," Ophthalmology. Oct. 1, 2018;125(10):1492-1499.
Gambill et al., "Mydriatic Effect of Four Drugs Determined With Pupillograph," Archives of Ophthalmology. Jun. 1, 1967;77(6):740-746.
Geyer et al. "The additive miotic effects of dapiprazole and pilocarpine," Graefe's Archive for Clinical and Experimental Ophthalmology. Jul. 1995;233:448-451.
Gilmartin et al., "Reversal of tropicamide mydriasis with single instillations of pilocarpine can induce substantial pseudo-myopia in young adults," Ophthalmic and Physiological Optics. Sep. 1995;15(5):475-479.

(56) References Cited

OTHER PUBLICATIONS

Ginsburg AP "Contrast sensitivity and functional vision in Functional Vision," International ophthalmology clinics. Apr. 1, 2003;43(2):5-15.
Ginsburg AP "Contrast sensitivity: determining the visual quality and function of cataract, intraocular lenses and refractive surgery," Current opinion in ophthalmology. Feb. 1, 2006;17(1):19-26.
Ginsburg AP "Vision Channels, Contrast Sensitivity and Functional Vision," Proc. SPIE 5292, Human Vision and Electronic Imaging IX, (Jun. 7, 2004); pp. 215-225. https://doi.org/10.1117/12.548289.
Giovannitti et al. "Alpha-2 adrenergic receptor agonists: a review of current clinical applications," Anesthesia Progress. Mar. 1, 2015;62(1):31-38.
Godbillion J "Determination of the major metabolite of phentolamine in human plasma and urine by high performance liquid chromatography," Journal of Chromatography B: Biomedical Sciences and Applications. Mar. 1, 19813;222(3):461-466.
Goel et al. "Aqueous humor dynamics: a review," The Open Ophthalmology Journal. 2010;4:52-59.
Goel et al. "Driving ability after pupillary dilatation," Eye. Aug. 2003;17(6):735-738.
Goertz et al. "Review of the impact of presbyopia on quality of life in the developing and developed world", Acta Ophthalmol. 2014;92(6):497-500.
Goldstein I. "Oral phentolamine: an alpha-1, alpha-2 adrenergic antagonist for the treatment of erectile dysfunction," International Journal of Impotence Research. Mar. 2000;12(1):S75-80.
Gomez-Gomar et al. "HPLC method for the simultaneous determination of pilocarpine, isopilocarpine, pilocarpic acid and isopilocarpic acid," Journal of pharmaceutical and biomedical analysis. Jan. 1, 1989;7(12):1729-1734.
Hadzija et al., "Physicochemical Stability of Papaverine Hydrochloride-Phentolamine Mesylate Mixtures Used for Intracavernous Injection: A Preliminary Evaluation," The Journal of Urology. Jul. 1, 1988;140(1):64-65.
Hara et al., "Bunazosin, a Selective a1-Adrenoceptor Antagonist, as an Anti-glaucoma Drug: Effects on Ocular Circulation and Retinal Neuronal Damage," Cardiovascular Drug Reviews. Mar. 2005;23(1):43-56.
Hays et al. "Assessment of the Psychometric Properties of a Questionnaire Assessing Patient-Reported Outcomes with Laser in Situ Keratomileusis (PROWL)," JAMA Ophthalmology. Jan. 1, 2017;135(1):3-12.
Hersh et al. "Phase Four, Randomized, Double-Blinded, Controlled Trial of Phentolamine Mesylate in Two- to Five-year-old Dental Patients," Pediatric Dentistry. Jan. 15, 2017;39(1):39-45.
Hersh et al. "Phentolamine mesylate for accelerating recovery from lip and tongue anesthesia," Dental Clinics. Oct. 1, 2010;54(4):631-642.
Hill et al. "Specificity of innervation of iris musculature by sympathetic nerve fibres in tissue culture", Pflugers Archiv: European Journal of Physiology. Jan. 1, 1976;361(2):127-34.
Hogan et al. "Dose response study of dapiprazole HCI in the reversal of mydriasis induced by 2.5% phenylephrine," Journal of Ocular Pharmacology and Therapeutics. Aug. 1997;13(4):297-302.
Holladay et al. "Functional vision and corneal changes after laser in situ keratomileusis determined by contrast sensitivity, glare testing and corneal topography," Journal of Cataract & Refractive Surgery. May 1, 1999;25(5):663-669.
Holladay et al. "Phentolamine Mesylate Ophthalmic Solution Once Daily Reduces Pupil Diameter and Improves Night Vision Disturbances," AAO Annual Meeting, 2018, PA025, 14 pages.
Holve et al. "Optical Coherence Tomography and Slit Lamp Imaging of Corneal Dystrophy in the Dutch Belted Rabbit", vol. 8, p. 9, Unpublished data, (1page).
Hong et al. "Tropicamide," In: StatPearls [Internet]. Treasure Island (FL): StatPearls Publishing, 2020, 4 pages.
Howe et al. "The objective assessment of contrast sensitivity function by electrophysiological means," British Journal of Ophthalmology. Sep. 1, 1984;68(9):626-638.
International Preliminary Report on Patentability for International Application No. PCT/US2022/029862 dated Nov. 30, 2023, 12 pages.
International Search Report and Written Opinion for International Application No. PCT/US2014/014067, dated May 21, 2014, 8 pages.
International Search Report and Written Opinion for International Application No. PCT/US2014/014070, dated Apr. 15, 2014, 10 pages.
International Search Report and Written Opinion for International Application No. PCT/US2022/029862, dated Aug. 3, 2022, 15 pages.
Ishikawa et al. "Comparison of post-junctional alphaadrenoceptors in iris dilator muscle of humans, and albino and pigmented rabbits," Naunyn-Schmiedeberg's archives of pharmacology. Dec. 1996;354:765-772.
Isopto (2010). Isopto® Carpine (Pilocarpine Hydrochloride Ophthalmic Solution) FDA Documents 1%, 2% and 4%. Highlights of Prescribing Information/ / Package Insert / Label, 2009, Revised Jun. 2010, Alcon Laboratories, Inc. Fort Worth, TX, USA, 5 pages.
Israilov et al. "Intracavernous injections for erectile dysfunction in patients with cardiovascular diseases and failure or contraindications for sildenafil citrate," International Journal of Impotence Research. Feb. 2002;14(1):38-43.
Jackson et al. "A Combination of Phentolamine Eye Drops and Low Dose Pilocarpine Improves Near Vision in VEGA-1 Phase 2 Presbyopia Trial," AAO Annual Meeting, 2022, Abstract ID 30070768, 8 pages.
Jackson et al. "Influence of Pupil Size, Anisocoria, and Ambient Light on Pilocarpine Miosis: Implications for Supersensitivity Testing," Ophthalmology. Feb. 1, 1993;100(2):275-80.
Jin et al. "Degradation Characteristics of a Novel PAF Receptor Antagonist, SY0916, in Aqueous Solution," Journal of Analytical Methods in Chemistry. Jan. 14, 2019;2019, 8 pages. https://doi.org/10.1155/2019/8789470.
Johnston, C. "Relief for Patients Troubled by Night-Vision Complaints: Presented at AAO", PeerVoice Publication, dated Oct. 21, 2010, 1 page.
Kammarr et al. "LYNX-1: A Pivotal Phase 3 Randomized Placebo-Controlled Trial of Phentolamine Ophthalmic Solution in Subjects with Dim Light Vision Disturbance," AAOpt Annual Meeting, 2022, Abstract ID 10526, 1 page.
Kan et al. "UPLC-MS/MS Determination of Phentolamine in Human Plasma and its Application to a Pharmacokinetic Study," Drug Research. Jan. 22, 2014:607-612.
Karpecki et al. "Phentolamine eye drops reverse pharmacologically induced mydriasis in a randomized phase 2b trial," Optometry and Vision Science. Mar. 1, 2021;98(3):234-242.
Kass et al. "The Ocular Hypertension Treatment Study: a randomized trial determines that topical ocular hypotensive medication delays or prevents the onset of primary open-angle glaucoma," Archives of Ophthalmology. Jun. 1, 2002;120(6):701-713.
Kato et al. "Effects of brimonidine tartrate 0.1% ophthalmic solution on the pupil, refraction, and light reflex," Scientific Reports. Jun. 13, 2018;8(1):9003, 5 pages. doi:10.1038/s41598-018-27436-8.
Katz et al. "VEGA-1: Phentolamine Ophthalmic Solution as a Single Agent Improves Distance-Corrected Near Visual Acuity in Patients with Presbyopia," ARVO Annual Meeting, 2022, Abstract ID 3712883, 1 page.
Kennedy et al. "High-performance liquid chromatographic analysis of pilocarpine hydrochloride, isopilocarpine, pilocarpic acid and isopilocarpic acid in eye-drop preparations," Journal of Chromatography A. Aug. 7, 1981;212(3):331-338.
Kerger et al. "An assay for phentolamine using high performance liquid chromotography with electrochemical detection," Analytical biochemistry. Apr. 1, 1988;170(1):145-151.
Kesler et al. "Effect of brimonidine tartrate 0.2% ophthalmic solution on pupil size," Journal of Cataract and Refractive Surgery. 2004;30(8):1707-1710.
Kiel et al. "Paradoxical effect of phentolamine on aqueous flow in the rabbit," Journal of ocular pharmacology and therapeutics. Feb. 1, 2007;23(1):21-6.

(56) References Cited

OTHER PUBLICATIONS

Kimlin et al. "Nighttime Driving in Older Adults: Effects of Glare and Association with Mesopic Visual Function," Investigative Ophthalmology & Visual Science. May 1, 2017;58(5):2796-803.
Kinney et al. "Temporal Effects of 2% Pilocarpine Ophthalmic Solution on Human Pupil Size and Accommodation," Military Medicine. Jan. 7, 2020;185(Supplement_1):435-442.
Kirsten et al. Clinical pharmacokinetics of vasodilators. Part II. Clin Pharmacokinet (1998) 35(1):9-36.
Klein et al. "Prevalence of glaucoma. The Beaver Dam Eye Study," Ophthalmology. Oct. 1, 1992;99(10):1499-1504.
Kobayashi et al. "Efficacy of bunazosin hydrochloride 0.01% as adjunctive therapy of latanoprost or timolol," Journal of Glaucoma. Feb. 1, 2004;13(1):73-80.
Konno et al. "Characterization of postsynaptic alpha-1 adrenoceptors in the rabbit iris dilator smooth muscle," Naunyn-Schmiedeberg's archives of pharmacology. Jul. 1986;333:271-276.
Koss et al. "Pharmacological characterization of alphaadrenoceptors involved in nictitating membrane and pupillary responses to sympathetic nerve stimulation in cats," Naunyn-Schmiedeberg's archives of pharmacology. Jan. 1988;337(1):18-23.
Krupin et al. "Effect of prazosin on aqueous humor dynamics in rabbits," Archives of Ophthalmology. Sep. 1, 1980;98(9):1639-42.
Kupersmith et al. "Contrast sensitivity loss in multiple sclerosis," Investigative ophthalmology & visual science. Jun. 1, 1984;25(6):632-639.
Kwon et al. "Primary open-angle glaucoma." New England Journal of Medicine. Mar. 12, 2009;360(11):1113-1124.
Lai et al. "Improved Synthesis of Phentolamine Mesilate," Huagong Shikan, 2001, vol. 15, No. 5, p. 45-47 (Abstract).
Langevin et al. "Historical Data: Histopathology Lesions Observed in the Eyes of Control Rabbits in Topical Ocular Administration and Contact Lens Studies," Toxicologic Pathology. Oct. 2018;46(7):799-820.
Leavitt et al. "Pupillary Response to Four Concentrations of Pilocarpine in Normal Subjects: Application to Testing for Adie Tonic Pupil," American journal of ophthalmology. Mar. 1, 2002;133(3):333-336.
Lee et al. "Efficacy of brimonidine tartrate 0.2% ophthalmic solution in reducing halos after laser in situ keratomileusis," Journal of Cataract & Refractive Surgery. Jun. 1, 2008;34(6):963-967.
Lewis et al. "Fixed-dose combination of AR-13324 and latanoprost: A double-masked, 28-day, randomised, controlled study in patients with open-angle glaucoma or ocular hypertension," British Journal of Ophthalmology. Mar. 1, 2016;100(3):339-344.
Lin et al. "Pharmacokinetics Study of Phentolamine Mesylate Injection in Healthy Volunteers," Journal of Sichuan University (Medical Sciences). Nov. 20, 2018;49(6):929-933.
Liu et al. "Assessing the utility of 2.5% phenylephrine for diagnostic pupillary dilation," Canadian Journal of Ophthalmology. Aug. 1, 2017;52(4):349-354.
Lograno et al. "Receptor-responses in fresh human ciliary muscle," British journal of pharmacology. Feb. 1986;87(2):379-385.
Marshall et al. "Therapy for Open-Angle Glaucoma," The Consultant Pharmacist. Aug. 1, 2018;33(8):432-445.
Martell et al. "Chelates of Ascorbic Acid Formation and Catalytic Properties," Advances in Chemistry, 1982, vol. 200, pp. 153-187.
Martinez et al. "Effect of pupillary dilation on corneal optical aberrations after photorefractive keratectomy," Archives of Ophthalmology. Aug. 1, 1998;116(8):1053-1062.
Marx-Gross et al. "Brimonidine versus dapiprazole: Influence on pupil size at various illumination levels," Journal of Cataract and Refractive Surgery. 2005;31(7):1372-1376.
Matsuura et al. "Determination of pilocarpine in aqueous humour by liquid chromatography—atmospheric pressure chemical ionization mass spectrometry," Journal of Chromatography B: Biomedical Sciences and Applications. 1993;621(2):173-180.
Mcauliffe-Curtin et al. "Review of alpha adrenoceptor function in the eye," Eye. Jul. 1989;3(4):472-476.
Mcdonald et al. "MIRA-3: A 2nd Phase 3 Randomized Placebo-Controlled Trial of Phentolamine Ophthalmic Solution to Reverse Pharmacologically Induced Mydriasis," ASCRS Annual Meeting, Paper ID 81993, 2022, 12 pages.
Mcdonald et al. "Phentolamine Mesylate Treatment of Severe Night Vision Complaints," AAO Abstracts, PO433, Oct. 18, 2010, 3 pages.
Mcdonald et al. "Phentolamine mesylate treatment of severe night-vision complaints," Presented at: Annual Meeting of the American Society of Cataract and Refractive Surgery; Mar. 25-29, 2011; San Diego, CA, 17 pages.
Mcdonnell et al. "Associations of presbyopia with vision-targeted health-related quality of life," Arch Ophthalmol. 2003, 121(11), 1577-1581.
Mcmahon, CG "A pilot study of the role of intracavernous injection of vasoactive intestinal peptide (VIP) and phentolamine mesylate in the treatment of erectile dysfunction," International Journal of Impotence Research. Dec. 1, 1996;8(4):233-236.
Mittag et al. "Alpha-adrenergic antagonists: correlation of the effect on intraocular pressure and on alpha 2-adrenergic receptor binding specificity in the rabbit eye," Experimental eye research. Apr. 1, 1985;40(4):591-599.
Mohammadpour et al. "Updates on Managements for Keratoconus," Journal of current ophthalmology. Jun. 1, 2018;30(2):110-124.
Molinari et al. "Dapiprazole clinical efficiency for counteracting tropicamide 1%," Optometry and vision science. May 1, 1994;71(5):319-322.
Monestam et al. "Long-time results and associations between subjective visual difficulties with car driving and objective visual function 5 years after cataract surgery," Journal of Cataract & Refractive Surgery. Jan. 1, 2006;32(1):50-5.
Montes-Micro et al. "Choice of spatial frequency for contrast sensitivity evaluation after corneal refractive surgery," Journal of Refractive Surgery. Nov. 1, 2001;17(6):646-651.
Montes-Micro et al. "Visual performance with multifocal intraocular lenses: Mesopic contrast sensitivity under distance and near conditions," Ophthalmology 2004;111:85-96.
Moore et al. "Anterior Corneal Dystrophy of American Dutch Belted Rabbits: Biomicroscopic and Histopathologic Findings," Vet. Pathol. 1987; 24:28-33.
Moore et al. "Pharmacokinetics of lidocaine with epinephrine following local anesthesia reversal with phentolamine mesylate," Anesthesia progress. Jun. 1, 2008;55(2):40-48.
Motolko et al. "Contrast sensitivity in asymmetric glaucoma," International ophthalmology. Jan. 1984;7:45-49.
MUCOMYST® (acetylcysteine solution), Prescribing Information/ Package Insert / Label, 2001, Revised Oct. 2006, Bristol-Myers Squibb Company, 18 pages.
Muftuoglu et al. "Drug-induced intraocular lens movement and near visual acuity after AcrySof intraocular lens implantation," Journal of Cataract & Refractive Surgery. Jul. 1, 2005;31(7):1298-1305.
Murphy et al., "How red is white eye? Clinical grading of normal conjunctiva! Hyperemia," Eye. May 2007;21(5):633-638.
Nagasubramanian S. "A Comparison of the Ocular Hypotensive Efficacy, Safety and Acceptability of Brimonidine 0.2% Twice Daily Versus Pilocarpine 2.0% Thrice Daily as Adjunct Therapy with Beta-Blockers," Glaucoma Update VI. Springer Berlin Heidelberg; 2000:203-208.
Nakamura et al. "Evaluation of alpha-1 adrenoceptors in the rabbit iris: pharmacological characterization and expression of mRNA," British journal of pharmacology. Jul. 1999;127(6):1367-1374.
National Center for Biotechnology Information (2022). PubChem Compound Summary for CID 517293, Phentolamine, methane sulfonate. Retrieved Sep. 15, 2022 from https://pubchem.ncbi.nlm.nih.gov/compound/Phentolamine_-methane-sulfonate, 13 pages.
National Center for Biotechnology Information (2022). PubChem Compound Summary for CID 91430, Phentolamine mesylate. Retrieved Sep. 15, 2022 from https://pubchem.ncbi.nlm.nih.gov/compound/Phentolamine-mesylate, 39 pages.
National Institutes of Health "NIH urges dilated eye exams to detect glaucoma", Accessed Apr. 24, 2020, 3 pages. Retrieved online: https://www.nih.gov/news-events/news-releases/nih-urges-dilated-eye-exams-detect-glaucoma.
National Institutes of Health, "Visual acuity test", Feb. 23, 2015, online://medlineplus.qov/ency/article/003396.htm, 3 pages.

(56) References Cited

OTHER PUBLICATIONS

Neonatal Intensive Care Unit, "Edrophonium," Children's Hospital London Health Science Centre, Manual , May 26, 2011, 4 pages.
Nielsen et al. "Effect of alpha- and beta-receptor active drugs on corneal thickness," Acta Ophthalmologica. Jun. 1985;63(3):351-354.
Noordam et al. "Quantitative Determination of Pilocarpine, Isopilocarpine, Pilocarpic Acid, and Isopilocarpic Acid in Clinical Ophthalmic Pilocarpine Formulations by Reversed-Phase Liquid Chromatography," Journal of Pharmaceutical Sciences. 1981;70(1):96-97.
Notice of Allowance for U.S. Appl. No. 18/091,761 dated Feb. 28, 2024, 5 pages.
Notice of Intention to Grant a Patent dated Apr. 10, 2019 from European Patent Application 14746208.9 (162 pages). European Search Report for Patent No. 147462089 Ocularis 2018.
Nyman et al. "Effects of Dapiprazole on the Reversal of Pharmacologically Induced Mydriasis," Optometry and vision science. Sep. 1, 1990;67(9):705-709.
Office Action for U.S. Appl. No. 18/091,761 dated May 5, 2023, 12 pages.
Office Action for U.S. Appl. No. 18/091,761 dated Oct. 16, 2023, 5 pages.
Ogure et al. "Properties of [3H]bunazosin binding in rat kidney," Clinical Therapeutics. Jan. 1, 1988;10(5):559-567.
OraVerse® (2016b). OraVerse FDA Documents. FDA approves OraVerse for pediatric dental patients 3 years and older, May 2016, 3 pages.
ORAVERSE® (phentolamine mesylate) injection; Prescribing Information/ Package Insert / Label, Initial US Approval: 1952; Novalar 2008, 2 pages.
OraVerse® (2016a). OraVerse (phentolamine mesylate) FDA Documents injection, Highlights of Prescribing InformationPackage Insert / Label, Initial US approval 1952, Revised Mar. 2016, Septodont, Inc., 4 pages.
Oshika et al. "Effect of bunazosin hydrochloride on intraocular pressure and aqueous humor dynamics in normotensive human eyes," Archives of Ophthalmology. Nov. 1, 1991;109(11):1569-1574.
Oshika et al. "Incidence of intraoperative floppy iris syndrome in patients on either systemic or topical alpha(1)-adrenoceptor antagonist," American journal of ophthalmology. Jan. 1, 2007;143(1):150-151.
Owsley C. "Contrast Sensitivity," Ophthalmol Clin N Am. 2003; 16:171-177.
Owsley et al. "Contrast sensitivity, acuity, and the perception of 'real-world' targets," British Journal of Ophthalmology. Oct. 1, 1987;71(10):791-796.
Ozulken et al. "Effect of topical pilocarpine on refractive surgery outcomes," International Ophthalmology. Mar. 2020;40:733-740.
Padma-Nathan et al. "Long-term safety and efficacy of oral phentolamine mesylate (Vasomax) in men with mild to moderate erectile dysfunction," International journal of impotence research. Aug. 2002;14(4):266-270.
PARAMYD® (hydroxyamphetamine hydrobromide/ tropicamide ophthalmic solution) 1%/0.25% US Prescribing Information, Somerset, NJ.: Akorn, Inc.; 2001, 7 pages.
Park et al. "Clinical Efficacy of Pinhole Soft Contact Lenses for the Correction of Presbyopia," Seminars in Ophthalmology. 2019; 34(2), 106-114.
Pepose et al. "A randomized phase 2 clinical trial of phentolamine mesylate eye drops in patients with severe night vision disturbances," BMC Ophthalmology. Oct. 8, 2022;22(1):402, 11 pages.
Pepose et al. "Phase 2 Clinical Trial to Evaluate the Efficacy of Phentolamine Ophthalmic Solution and Low-Dose Pilocarpine for the Treatment of Presbyopia," American Society of Cataract and Refractive Surgery's annual meeting, Jul. 25, 2021, Las Vegas, Paper #76645, 13 pages.
Pepose et al. "Phase 3 clinical trial to evaluate the efficacy of phentolamine ophthalmic solution on the reversal of pharmacologically induced mydriasis," American Society of Cataract and Refractive Surgery's annual meeting, Jul. 26, 2021, Las Vegas, Paper #76599, 15 pages.
Pepose et al. "Phentolamine mesylate ophthalmic solution provides lasting pupil modulation and improves near visual acuity in presbyopic glaucoma patients in a randomized phase 2b clinical trial," Clin Ophthalmol. 2021; 15:79-91.
Pepose et al. "Phentolamine mesylate ophthalmic solution provides long lasting pupil modulation and improves visual acuity," The Association for Research in Vision and Ophthalmology's annual meeting, 2020, ARVO Abstract No. 3364450, 15 pages.
Pepose et al. "Phentolamine Ophthalmic Solution as a Single Agent Improves Distance-Corrected Near Visual Acuity in Patients with Presbyopia," American Society of Cataract and Refractive Surgery's annual meeting, Apr. 25, 2022, Washington D.C., Paper No. 80665, 11 pages.
Pepose et al. "VEGA-1: Phentolamine Ophthalmic Solution in combination with Low Dose Pilocarpine Improves Distance-Corrected Intermediate Visual Acuity in Patients with Presbyopia," The Association for Research in Vision and Ophthalmology's annual meeting, 2022, ARVO Abstract No. 3707817, 15 pages.
Pepose, J. "Phase 2 Clinical Trial to Evaluate the Efficacy of Phentolamine Ophthalmic Solution and Low-Dose Pilocarpine for the Treatment of Presbyopia," American Academy of Ophthalmology's annual meeting, 2021. Abstract ID 30068457, 10 pages.
Peter et al. "Pharmacokinetics of Pilocarpine in Subjects with Varying Degrees of Renal Function," Journal of Clinical Pharmacology. 2000;40(12 Pt 2):1470-1475.
Pop et al. "Risk factors for night vision complaints after LASIK for myopia," Ophthalmology, 2004; 111(1), 3-10.
Poulet et al. "Development of hibernomas in rats dosed with phentolamine mesylate during the 24-month carcinogenicity study," Toxicol Pathol, 2004; 32(5), 558-566.
Prata et al. "Iris morphologic changes related to alpha (1) adrenergic receptor antagonists: implications for intraoperative floppy iris syndrome," Ophthalmology, 2009;116:877-81.
Puell et al. "Mesopic contrast sensitivity in the presence or absence of glare in a large driver population," Graefes Arch Clin Exp Ophthalmol, 2004;242(8), 755-761.
Radi et al. "Comparative pathophysiology, toxicology, and human cancer risk assessment of pharmaceutical-induced hibernoma," Toxicol Appl Pharmacol, 2013;273(3), 456-463.
Rahman et al. "Brimonidine for glaucoma," Expert Opinion on Drug Safety. 2010;9(3):483-491.
Ramsay, D. A. "Dilute Solutions of Phenylephrine and Pilocarpine in the Diagnosis of Disordered Autonomic Innervation of the Iris: Observations in Normal Subjects, and in the Syndromes of Horner and Holmes-Adie," Journal of the Neurological Sciences, 1986; vol. 73(1):125-134.
Regan et al. "Visual acuity and contrast sensitivity in multiple sclerosis—hidden visual loss: an auxiliary diagnostic test," Brain. 1977; 100(3):563-579.
Regitine. (1998). Regitine FDA Documents. Highlights of Prescribing Information, 38 pages.
Regitine-phentolamine mesylate injection, powder, lyophilized, for suspension; label/prescribing information; Novartis Pharmaceuticals Corporation (1998), 5 pages.
Rengstorff et al. "Mydriatic and cycloplegic drugs: a review of ocular and systemic complications," Optometry and Vision Science. Feb. 1, 1982;59(2):162-177. Retrieved from https://www.ncbi.nlm.nih.gov/pubmed/7039329.
REV-EYES. (2013). Federal Register; 78(92):27971 "Determination that REV-EYES (dapiprazole hydrochloride ophthalmic solution), 0.5%, was not withdrawn from sale for reasons of safety or effectiveness", 1 page.
Rev-Eyes® dapiprazole hydrochloride ophthalmic solution 0.5%. NDA 019849. Dec. 31, 1990, 181 pages.
Rev-Eyes® (dapiprazole hydrochloride ophthalmic solution) Ophthalmic Eyedrops 0.5% (Bausch & Lomb), Drug Reference Encyclopedia, 1998, 4 pages, U.S. Pat. No. 4,252,721, Manufactured by Abbott Laboratories, North Chicago, IL. Retrieved online: https://theodora.com/drugs/rev_eyes_ophthalmic_eyedrops_05_bausch_lomb.html.

(56) References Cited

OTHER PUBLICATIONS

Rev-Eyes™, in Physicians' Desk Reference for Ophthalmic Medicines (2003) Thomson PDR, p. 258.
Rhopressa (2017). "Rhopressa pharmacology/toxicology NDA review and evaluation", United States Food and Drug Administration; Non-Clinical Review(s), Application No. 208254Orig1s000, 95 pages.
Richards et al. "Circulatory and alpha-adrenoceptor blocking effects of phentolamine," British Journal of Clinical Pharmacology. Jun. 1978;5(6):507-513.
Ridder et al. "Contrast Sensitivity and Tear Layer Aberrometry in Dry Eye Patients," Optometry and Vision Science. Sep. 1, 2009;86(9):E1059-68.
Robin et al. "Adherence in glaucoma: objective measurements of once-daily and adjunctive medication use," American journal of ophthalmology. Oct. 1, 2007;144(4):533-540.
Romero-Jimenez et al. "Keratoconus: A Review," Contact & Lens Anterior Eye, 2010: 33(4), 157-166.
Rosen, Emanuel S. "Night vision disturbance," Journal of Cataract & Refractive Surgery. 2005;31(2):247-249.
Rutherford et al. "Local and systemic toxicity of intraoral submucosal injections of phentolamine mesylate (OraVerse)," Anesthesia Progress. Dec. 1, 2009;56(4):123-127.
Ruthkowski et al. "Mydriasis and Increased Intraocular Pressure," Arch Ophthalmol. 1972;87(1):21-24.
Safety and Efficacy of Ophthalmic Phentolamine Mesylate in Glaucoma, a clinical study description, available from clinicaltrials.gov online on May 23, 2019, 5 pages.
Safety and Efficacy of Ophthalmic Phentolamine Mesylate in Glaucoma, a clinical study description, available from clinicaltrials.gov online on Oct. 14, 2019, 6 pages.
Safety and Efficacy of Ophthalmic Phentolamine Mesylate to Reverse Pharmacologically Induced Mydriasis, a clinical study description, available from clinicaltrials.gov online on Jul. 18, 2019; NCT04024891, 7 pages.
Safety and Efficacy of Ophthalmic Phentolamine Mesylate to Reverse Pharmacologically Induced Mydriasis, a clinical study description, available from clinicaltrials.gov online on Oct. 14, 2019; NCT04024891, 7 pages.
Sandoval et al. "Comparison of visual outcomes, photopic contrast sensitivity, wavefront analysis, and patient satisfaction following cataract extraction and IOL implantation: aspheric vs spherical acrylic lenses," Eye. 2008; 22:1469-1475.
Schallhorn et al. "Comparison of night driving performance after wavefront-guided and conventional LASIK for moderate myopia," Ophthalmology. 2009; 116(4), 702-709.
Serle et al. "Two Phase 3 Clinical Trials Comparing the Safety and Efficacy of Netarsudil to Timolol in Patients with Elevated Intraocular Pressure: Rho Kinase Elevated IOP Treatment Trial 1 and 2 (ROCKET-1 and ROCKET-2)," Am J Ophthalmol. 2017;186:116-127.
Shah et al. "Influence of thymoxamine eye-drops on the mydriatic effect of tropicamide and phenylephrine alone and in combination," Ophthalmic Physiol Opt. 1989; 9(2), 153-155.
Shemesh et al. "Effect of brimonidine tartrate 0.10% ophthalmic solution on pupil diameter," Journal of Cataract and Refractive Surgery. 2011;37(3):486-489.
Sherwood et al. "Twice-Daily 0.2% Brimonidine-0.5% Timolol Fixed-Combination Therapy vs Monotherapy with Timolol or Brimonidine in Patients with Glaucoma or Ocular Hypertension," Archives of Ophthalmology. Sep. 1, 2006;124(9):1230-1238.
Shiau et al. "The role of episcleral venous pressure in glaucoma associated with Sturge-Weber syndrome," Journal of American Association for Pediatric Ophthalmology and Strabismus. Feb. 1, 2012;16(1):61-64.
Shiose et al. "Epidemiology of glaucoma in Japan—a nationwide glaucoma survey," Japanese journal of ophthalmology. Jan. 1, 1991;35(2):133-155. Retrieved from https://www.ncbi.nlm.nih.gov/pubmed/1779484.
Siderov et al. "Pupillary dilation: the patient's perspective," Clinical and Experimental Optometry. 1996;79(2):62-66.
Silva et al. "Phentolamine bioequivalence study," International journal of clinical pharmacology and therapeutics. 2004;42(1):43-49.
Single Dose Study of Phentolamine Mesylate Eye Drops in Patients with Severe Night Vision Disturbances, Aug. 1, 2019, Ocuphire Pharma, Inc., 5 pages.
Sioufi et al. "Gas chromatographic determination of phentolamine (Regitine®) in Human Plasma," Journal of Chromatography B: Biomedical Sciences and Applications. Mar. 13, 1981;222(3):429-435.
Smith et al., "An increased effect of pilocarpine on the pupil by application of the drug in oil,". May 1, 1978;62(5):314-317.
Soli et al., "Vasoactive Cocktails for Erectile Dysfunction: Chemical Stability of PGE1, Papaverine and Phentolamine," The Journal of Urology. Aug. 1, 1998;160(2):551-555.
Sommer et al. "Relationship between intraocular pressure and primary open angle glaucoma among white and black Americans," The Baltimore Eye Survey. Archives of ophthalmology. Aug. 1, 1991;109(8):1090-1095.
Steiner "State of independent optometry: optometry dominates primary eyecare," Review of Optometric Business, 2013, 2 pages.
Steinhauer et al. "Sympathetic and parasympathetic innervation of pupillary dilation during sustained processing," International journal of psychophysiology. Mar. 1, 2004;52(1):77-86.
Sternitzke et al. "High-performance liquid chromatographic determination of pilocarpitie hydrochloride and its degradation products using a /l-cyclodextrin column," Journal of Chromatography. 1992;10(589):159-164.
Suzuki et al. "Distribution of alpha-1 adrenoceptor subtypes in RNA and protein in rabbit eyes," British journal of pharmacology. Feb. 2002;135(3):600-608.
Takayanagi et al. "Alpha 1B-adrenoceptor mechanisms in rabbit iris dilator," The Japanese Journal of Pharmacology. 1992;59(3):301-305.
Tang et al. "Visual performance of lasik patients," Ann Acad Med Singapore 2006; 35:541-546.
Tanzer et al. "A Pharmacokinetic and Pharmacodynamic Study of Intravenous Pilocarpine in Humans," Journal of dental research. Dec. 1995;74(12):1845-1849.
Taylor et al. "The circulatory effects of phentolamine in man," Circulation. 1965; 31(5):741-754. doi: 10.1161/01.cir.31.5.741.
Tecnis Multifocal Intraocular Lens, Models ZM900 and ZMA00, Premarket Approval Application No. P080010; CDRH/FDA, Summary of Safety and Effectiveness (SSED), 2009, 38 pages. Retrieved online: https://www.accessdata.fda.gov/cdrh_docs/pdf8/P080010B.pdf.
Tham et al. "Global prevalence of glauco ma and projections of glaucoma burden through 2040: a systematic review and meta-analysis," Ophthalmology. Nov. 1, 2014;121(11):2081-2090. doi:10.1016/j.ophtha.2014.05.013.
Thomas J. "Normal and amblyopic contrast sensitivity functions in central and peripheral retinas," Invest. Ophthalmol Visual Sci. 1978; 17:746-753.
Thompson, H. S. "Adie's Syndrome: Some New Observations," Transactions of the American Ophthalmological Society. 1977; 75:587-626.
Thordsen et al. "Miotic effect of brimonidine tartrate 0.15% ophthalmic solution in normal eyes," Journal of Cataract and Refractive Surgery. 2004;30(8):1702-1706.
Threw et al. "Ocular responses in healthy subjects to topical bunazosin 0.3%—an alpha 1-adrenoceptor antagonist," Br J Ophthalmol, 1991: 75(7), 411-413.
Troy et al., "Remington: The Science and Practice of Pharmacy," 21st ed., University of the Sciences, Philadelphia, Pennsylvania, 2006, p. 1032.
Tu et al. "Stability of papaverine hydrochloride and phentolamine mesylate in injectable mixtures," American Journal of Hospital Pharmacy. 1987; 44(11):2524-2527.
Tuan et al. "Improved contrast Sensitivity and visual acuity after wavefront-guided laser in situ Keratomileusis: In-depth statistical analysis," J. Cataract Refract. Surg. 2006; 32:215-230.
Tucker et al. "The depth-of-focus of the human eye for Snellen letters," Am J Optom Physiol Opt. 1975;52(1):3-21.

(56) References Cited

OTHER PUBLICATIONS

Uusitalo, H. "The effect of autonomic receptor blockers on the ocular response to topical chemical irritation," Acta Physiol Scand. 1984; 121:1-8.
Van Alphen, G. W. "The adrenergic receptors of the intraocular muscles of the human eye," Invest Ophthalmol. 1976;15(6):502-505. Retrieved online: https://www.ncbi.nlm.nih.gov/pubmed/6403.
Van Demark et al. "Phentolamine rescue for digital ischemia following lidocaine with epinephrine local anesthesia: Case presentation, review of the literature and treatment options," s. South Dakota Medicine: the Journal of the South Dakota State Medical Association. Nov. 1, 2021;74(11):532-536.
Van Gaalen et al. "Relationship between contrast sensitivity and spherical aberration: comparison of 7 contrast sensitivity tests with natural and artificial pupils in healthy eyes," Journal of Cataract & Refractive Surgery. Jan. 1, 2009;35(1):47-56.
Vivacy, "Stylage", retrieved from http://www.stylage.eu/technology.html on May 27, 2016, 4 pages.
Volkers et al. "Spatial contrast sensitivity and the diagnosis of amblyopia," Brit J Ophthalmology. 1987; 71:58-65.
Wachler et al. "Role of Clearance and treatment zones in refractive surgery," J. Cataract Refract. Surg. 1999; 25:16-23.
Wachler et al. "Comparison of Contrast Sensitivity in Different Soft Contact Lenses and Spectacles," CLAO Journal. 1999; 25;48-50.
Wang et al. "Degradation Kinetics of Phentolamine Hydrochloride in Solution," Journal of Pharmaceutical Sciences. Nov. 1, 1988;77(11):972-976.
Wang et al. "Different effects of topical prazosin and pilocarpine on uveoscleral outflow in rabbit eyes," China Academic Journal Electronic Publishing House. 2016;19(3):191-194.
Wang et al. "Risk of intraoperative floppy iris syndrome among selective alpha-1 blockers—A consistency model of 6,488 cases," Frontiers in Medicine. Aug. 30, 2022;9:941130, 12 pages.
Waring et al. "Safety and Efficacy of AGN-190584 in Individuals with Presbyopia: The GEMINI 1 Phase 3 Randomized Clinical Trial," JAMA Ophthalmol. 2022;140(4):363-371.
West et al. "How does visual impairment affect performance on tasks of everyday life?" The SEE Project. Salisbury Eye Evaluation. Arch Ophthalmol. 2002;120(6):774- 80.
Wiederholt et al. "The regulation of trabecular meshwork and ciliary muscle contractility," Progress in retinal and eye research. May 1, 2000;19(3):271-95.
Wilson et al. "Short-term, subchronic and chronic toxicology studies," Hayes' Principles and Methods of Toxicology. Hayes, A.W. and Kruger, C.L. (Eds). Chap. 24, CRC Press, N.Y., 2003, pp. 1205-1249.
Wilson et al. "Inconsistencies Exist in National Estimates of Eye Care Services Utilization in the United States," J Ophthalmol. 2015, Article ID: 435606, 5 pages.
Wood et al. "Pupil dilatation does affect some aspects of daytime driving performance," British journal of ophthalmology. Nov. 1, 2003;87(11):1387-1390.
Wright et al. "Time course of thymoxamine reversal of phenylephrine-induced mydriasis," Arch Ophthalmol. 1990;108(12):1729-32.
Xu et al. "Effect of Target Luminance on Optimum Pupil Diameter for Presbyopic Eyes," Optometry and Vision Science. 2016;91(11):1409-19.
Xu et al. "What is Optimal Pupil Size?" Cataract & Refractive Surgery Today. 2022, 10 pages. Retrieved online: https://crstoday.com/articles/jan-2022/what-is-the-optimal-pupil-size/.
Yoshitomi et al. "Adrenergic excitatory and cholinergic inhibitory innervations in the human iris dilator," Exp Eye Res, Mar. 1, 1985;40(3):453-9. 453-459.
Yu et al. "alpha(1A)-adrenoceptors mediate sympathetically evoked pupillary dilation in rats," Journal of Pharmacology and Experimental Therapeutics. Feb. 1, 2002;300(2):521-525.
Zetterstorm et al. "Pharmacological characterization of human ciliary muscle adrenoceptors in vitro," Experimental eye research. Mar. 1, 1988;46(3):421-430.
Zimmerman, T. J. "Pilocarpine," Ophthalmology, 1981; vol. 88, No. 1, p. 85-88.

* cited by examiner

PHENTOLAMINE MESYLATE AND THERAPEUTIC USES THEREOF

CROSS-REFERENCE TO RELATED APPLICATIONS

This application claims the benefit of European Patent Application No. 23383186.6, filed Nov. 21, 2023, the disclosure of which is incorporated by reference herein in its entirety.

FIELD OF THE INVENTION

This invention provides phentolamine mesylate that exhibits a particular x-ray powder diffraction (XRPD) pattern or exhibits one or more particular XRPD peaks. The invention also provides compositions comprising the phentolamine mesylate and compositions in which the phentolamine mesylate is dissolved. The invention also provides methods for treating or preventing an ocular disease or condition, comprising administering to a subject in need thereof an effective amount of the phentolamine mesylate, a composition comprising the phentolamine mesylate or a composition in which the phentolamine mesylate is dissolved.

BACKGROUND OF THE INVENTION

RYZUMVI®, an ophthalmic solution of phentolamine mesylate, was approved by the U.S. Food and Drug Administration (FDA) for treatment of pharmacologically induced mydriasis produced by adrenergic agonists or parasympatholytic agents. Phentolamine mesylate for injection was approved by the FDA for use in reversing soft-tissue anesthesia, for use in preventing or controlling hypertensive episodes in patients with pheochromocytoma, and for treatment of dermal necrosis following intravenous administration or extravasation of norepinephrine.

SUMMARY OF THE INVENTION

The present invention provides phentolamine mesylate that exhibits an XRPD pattern comprising a peak at 8.3±0.2 degrees 2-theta, a peak at 13.1±0.2 degrees 2-theta and a peak at 16.3±0.2 degrees 2-theta.

The invention further provides phentolamine mesylate that exhibits an XRPD pattern that is substantially the same as that depicted in FIG. 2A.

The invention further provides phentolamine mesylate that exhibits an XRPD pattern comprising the Table 3 peaks having at least 50% relative intensity.

The present invention provides phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta.

The invention further provides phentolamine mesylate that exhibits an XRPD pattern that is substantially the same as that depicted in FIG. 3A.

The invention further provides phentolamine mesylate that exhibits an XRPD pattern comprising the Table 4 peaks having at least 50% relative intensity.

Each phentolamine mesylate above is a "compound of the invention".

The present invention further provides compositions comprising a compound of the invention and a pharmaceutically acceptable carrier or vehicle and compositions in which a compound of the invention is dissolved (each composition being a "composition of the invention").

The present invention further provides a sealed container containing a compound of the invention and an inert gas.

The present invention further provides methods for treating or reversing pharmacologically induced mydriasis, comprising administering to a subject in need thereof an effective amount of a compound of the invention or a composition of the invention.

The present invention further provides methods for inhibiting contraction of smooth muscle of a subject's iris, comprising administering to a subject in need thereof an effective amount of a compound of the invention or a composition of the invention.

The present invention further provides methods for reducing a subject's pupil diameter, comprising administering to a subject in need thereof an effective amount of a compound of the invention or a composition of the invention.

The present invention further provides methods for improving visual contrast sensitivity or visual acuity, comprising administering to a subject in need thereof an effective amount of a compound of the invention or a composition of the invention.

The present invention further provides methods for treating or preventing an ocular disease or condition, comprising administering to a subject in need thereof an effective amount of a compound of the invention or a composition of the invention.

The present invention further provides methods for treating or preventing diabetic retinal disease, retinopathy of prematurity, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, sickle cell retinopathy, geographic atrophy, choroidal neovascularization, or corneal graft rejection, comprising administering to a subject in need thereof an effective amount of: phentolamine mesylate that exhibits an XRPD pattern that is substantially the same as that depicted in FIG. 1A or FIG. 1C; a composition comprising (i) phentolamine mesylate that exhibits an XRPD pattern that is substantially the same as that depicted in FIG. 1A or FIG. 1C and (ii) a pharmaceutically acceptable carrier or vehicle; or a composition in which phentolamine mesylate that exhibits an XRPD pattern that is substantially the same as that depicted in FIG. 1A or FIG. 1C is dissolved.

Each of the above methods is an "ocular method of the invention".

The present invention further provides methods for making phentolamine mesylate that exhibits an XRPD pattern comprising a peak at 8.4±0.2 degrees 2-theta and a peak at 16.3±0.2 degrees 2-theta, comprising: (a) heating a mixture comprising phentolamine mesylate comprising an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta; methane sulfonic acid; acetone; and water at about 45° C. for about thirty minutes to provide a heated mixture; (b) allowing the heated mixture to cool to room temperature to provide a cooled mixture; (c) diluting the cooled mixture with t-butyl methyl ether to provide a t-butyl methyl ether mixture; and (d) cooling the t-butyl methyl ether mixture to about −20° C. to precipitate the phentolamine mesylate that exhibits an XRPD pattern comprising a peak at 8.4±0.2 degrees 2-theta and a peak at 16.3±0.2 degrees 2-theta.

The present invention further provides methods for making phentolamine mesylate that exhibits an XRPD pattern comprising a peak at 8.4±0.2 degrees 2-theta and a peak at 16.3±0.2 degrees 2-theta, comprising: (a) heating a mixture comprising phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86 #0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta and dichloromethane at about 50° C. for about two hours to provide a heated mixture; (b) allowing the heated mixture to cool at about 25° C. for about two hours to provide cooled phentolamine mesylate; and (c) repeating steps (a) and (b) for up to about three days to provide the phentolamine mesylate that exhibits an XRPD pattern comprising a peak at 8.4±0.2 degrees 2-theta and a peak at 16.3±0.2 degrees 2-theta.

The present invention further provides methods for making phentolamine mesylate that exhibits an XRPD pattern comprising a peak at 8.4±0.2 degrees 2-theta and a peak at 16.3±0.2 degrees 2-theta, comprising: (a) dissolving phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta in a mixture comprising methyl ethyl ketone and water at about 80° C. to provide a solution; (b) cooling the solution to about 45° C. and adding one or more seeds of phentolamine mesylate that exhibits an XRPD pattern comprising a peak at 8.4±0.2 degrees 2-theta and a peak at 16.3±0.2 degrees 2-theta to provide a seeded mixture; (c) cooling the seeded mixture at 10° C. for about thirty minutes to provide a cooled mixture; (d) heating the cooled mixture at 35° C. under vacuum to reduce the volume of the mixture by about 33% and provide a reduced mixture; and (e) cooling the reduced mixture at 10° C. for about forty minutes to provide the phentolamine mesylate that exhibits an XRPD pattern comprising a peak at 8.4±0.2 degrees 2-theta and a peak at 16.3±0.2 degrees 2-theta.

The present invention further provides methods for making phentolamine mesylate that exhibits an XRPD pattern comprising a peak at 8.4±0.2 degrees 2-theta and a peak at 16.3±0.2 degrees 2-theta, comprising: (a) heating a mixture comprising phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta; methyl ethyl ketone; and water to 77° C. to provide a heated mixture; (b) cooling the heated mixture to 10° C. to provide a cooled mixture; and (c) repeating steps (a) and (b) twice to provide the phentolamine mesylate that exhibits an XRPD pattern comprising a peak at 8.4±0.2 degrees 2-theta and a peak at 16.3±0.2 degrees 2-theta.

The present invention further provides methods for making phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta, comprising (a) heating phentolamine mesylate that exhibits an XRPD pattern comprising a peak at 8.4±0.2 degrees 2-theta and a peak at 16.3±0.2 degrees 2-theta to about 126° C. to provide heated phentolamine mesylate; and (b) allowing the heated phentolamine mesylate to cool to room temperature to provide the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta.

The present invention further provides methods for making phentolamine mesylate that exhibits an XRPD pattern that is substantially the same as that depicted in FIG. 4A, comprising (a) heating a mixture comprising phentolamine mesylate that exhibits an XRPD pattern that is substantially the same as that depicted in FIG. 1A or FIG. 1C and acetone at about 50° C. for about two hours to provide a heated mixture; (b) allowing the heated mixture to cool at about 25° C. for about two hours to provide cooled phentolamine mesylate; and (c) repeating steps (a) and (b) for up to about three days to provide the phentolamine mesylate that exhibits an XRPD pattern that is substantially the same as that depicted in FIG. 4A.

The present invention further provides methods for making phentolamine mesylate that exhibits an XRPD pattern that is substantially the same as that depicted in FIG. 6A, comprising (a) pulverizing phentolamine mesylate that exhibits an XRPD pattern that is substantially the same as that depicted in FIG. 1A or FIG. 1C in the presence of an excess of 1,4-dioxane solvent to provide a pulverized mixture; and (b) removing the 1,4-dioxane solvent from the pulverized mixture to provide the phentolamine mesylate that exhibits an XRPD pattern that is substantially the same as that depicted in FIG. 6A.

Each of the above methods is a "synthesis method of the invention".

DETAILED DESCRIPTION OF THE INVENTION

Definitions

Figure 1A:
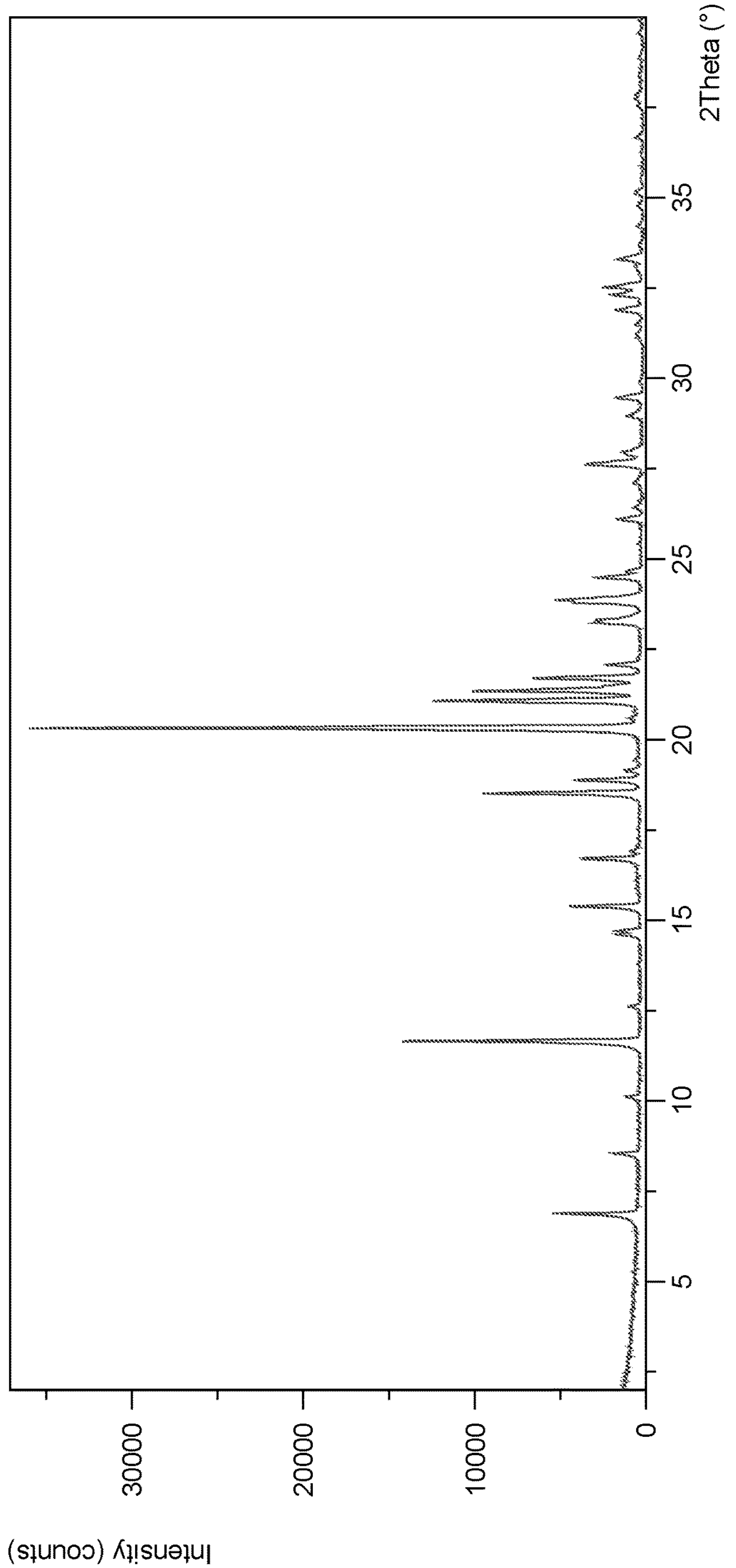
FIG. 1A depicts an XRPD pattern of phentolamine mesylate United States Pharmacopeia (USP) reference standard purchased from Sigma-Aldrich, Inc. (Product No. 1530004) ("Reference A").

The term "about" when immediately preceding a numerical value means±10% of the numerical value.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, "effective amount" refers to an amount of a compound or composition that is effective to treat or reverse pharmacologically induced mydriasis; inhibit contraction of smooth muscle of a subject's iris; reduce a subject's pupil diameter; improve visual contrast sensitivity or visual acuity; treat or prevent an ocular disease or condition; or treat or prevent diabetic retinal disease, retinopathy of prematurity, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, sickle cell retinopathy, geographic atrophy, choroidal neovascularization, or corneal graft rejection.

All weight percentages (i.e., "% by weight" and "wt. %" and w/w) referenced herein, unless otherwise indicated, are relative to the total weight of the compound or composition, as the case may be.

As used herein in connection with a compound of the invention, an "impurity" is a compound or substance other than phentolamine mesylate.

As used herein, "isolated" means isolated from a chemical synthesis reaction mixture. In some embodiments, an isolated compound is at least 95% pure and comprises no more than 5% of one or more impurities by weight, moles, or volume. By "x % pure" means that a compound includes no more than (100-x) % of one or more impurities by weight, moles, or volume. In some embodiments, an isolated compound is at least 96%, at least 97%, at least 98%, or at least 99% pure, and comprises no more than 4%, no more than 3%, no more than 2%, or no more than 1% of an impurity, respectively, by weight, moles, or volume. In some embodiments, the one or more impurities, if any, are present in the compound as a percent by weight. In some embodiments, the one or more impurities, if any, are present in the compound as a percent by mole. In some embodiments, the one or more impurities, if any, are present in the compound as a percent by volume.

As used herein, "room temperature" when used in connection with the synthesis methods of the invention is a temperature from about 20° C. to about 25° C.

As used herein, "substantially the same as" when used in connection with an XRPD pattern means that each peak (having an at least 2% relative intensity) of the XRPD pattern differs from a corresponding peak of a reference or comparative XRPD pattern by no more than ±0.2 degrees 2-theta. The most intense peak in an XRPD pattern is assigned 100% relative peak intensity and the intensity of all other peaks in the XRPD pattern is measured relative to the XRPD pattern's most intense peak (relative intensity).

As used herein, "substantially the same as" when used in connection with a DSC thermogram means that each peak of the DSC thermogram differs from a corresponding peak of a reference or comparative DSC thermogram by no more than ±3° C.

As used herein, "substantially the same as" when used in connection with a TG thermogram means that each peak of the TG thermogram differs from a corresponding peak of a reference or comparative TG thermogram by no more than ±2%.

As used herein, "stable" when used in connection with a compound means that the compound comprises no more than 10% of a degradation product by weight of the compound.

As used herein, "subject" a mammal. In some embodiments, the mammal is a human.

Compounds of the Invention

The present invention provides phentolamine mesylate that exhibits a particular XRPD pattern or exhibits one or more particular XRPD peaks.

Phentolamine mesylate has the structure:

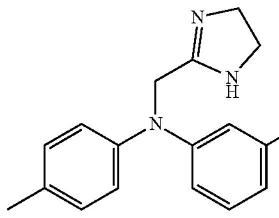
$CH_3SO_3H$.

In some embodiments, the phentolamine mesylate is crystalline. In some embodiments, the phentolamine mesylate is a phentolamine mesylate solvate. In some embodiments, the phentolamine mesylate solvate is crystalline.

In some embodiments, the compound of the invention is phentolamine mesylate that exhibits an XRPD pattern comprising a peak at 8.4±0.2 degrees 2-theta and a peak at 16.3±0.2 degrees 2-theta. In some embodiments, the XRPD pattern further comprises a peak at 13.1±0.2 degrees 2-theta, a peak at 19.4±0.2 degrees 2-theta, or a peak at 20.8±0.2 degrees 2-theta. In some embodiments, the XRPD pattern further comprises a peak at 18.8±0.2 degrees 2-theta or a peak at 20.0±0.2 degrees 2-theta. In some embodiments, the XRPD pattern further comprises a peak at 16.9±0.2 degrees 2-theta or a peak at 18.4±0.2 degrees 2-theta. In some embodiments, the XRPD pattern further comprises a peak at 8.9±0.2 degrees 2-theta or a peak at 22.2±0.2 degrees 2-theta. In some embodiments, the XRPD pattern further comprises a peak at 11.1±0.2 degrees 2-theta or a peak at 19.2±0.2 degrees 2-theta.

In some embodiments, the compound of the invention is phentolamine mesylate that exhibits an XRPD pattern comprising a peak at 8.4±0.2 degrees 2-theta, a peak at 13.1±0.2 degrees 2-theta, a peak at 16.3±0.2 degrees 2-theta, a peak at 19.4±0.2 degrees 2-theta, and a peak at 20.8±0.2 degrees 2-theta. In some embodiments, the XRPD pattern further comprises a peak at 18.8±0.2 degrees 2-theta or a peak at 20.0±0.2 degrees 2-theta. In some embodiments, the XRPD pattern further comprises a peak at 16.9±0.2 degrees 2-theta or a peak at 18.4±0.2 degrees 2-theta. In some embodiments, the XRPD pattern further comprises a peak at 8.9±0.2 degrees 2-theta or a peak at 22.2±0.2 degrees 2-theta. In some embodiments, the XRPD pattern further comprises a peak at 11.1±0.2 degrees 2-theta or a peak at 19.2±0.2 degrees 2-theta.

In some embodiments, the compound of the invention is phentolamine mesylate that exhibits an XRPD pattern comprising a peak at 8.4±0.2 degrees 2-theta, a peak at 13.1±0.2 degrees 2-theta, a peak at 16.3±0.2 degrees 2-theta, a peak at 18.8±0.2 degrees 2-theta, and a peak at 20.0±0.2 degrees 2-theta. In some embodiments, the XRPD pattern further comprises a peak at 19.4±0.2 degrees 2-theta or a peak at 20.8±0.2 degrees 2-theta. In some embodiments, the XRPD pattern further comprises a peak at 16.9±0.2 degrees 2-theta or a peak at 18.4±0.2 degrees 2-theta. In some embodiments, the XRPD pattern further comprises a peak at 8.9±0.2 degrees 2-theta or a peak at 22.2±0.2 degrees 2-theta. In some embodiments, the XRPD pattern further comprises a peak at 11.1±0.2 degrees 2-theta or a peak at 19.2±0.2 degrees 2-theta.

In some embodiments, the compound of the invention is phentolamine mesylate that exhibits an XRPD pattern comprising a peak at 13.1±0.2 degrees 2-theta, a peak at 16.3±0.2 degrees 2-theta, a peak at 16.9±0.2 degrees 2-theta, and a peak at 18.4±0.2 degrees 2-theta. In some embodiments, the XRPD pattern further comprises a peak at 8.4±0.2 degrees 2-theta, a peak at 19.4±0.2 degrees 2-theta, or a peak at 20.8±0.2 degrees 2-theta. In some embodiments, the XRPD pattern further comprises a peak at 18.8±0.2 degrees 2-theta or a peak at 20.0±0.2 degrees 2-theta. In some embodiments, the XRPD pattern further comprises a peak at 8.9±0.2 degrees 2-theta or a peak at 22.2±0.2 degrees 2-theta. In some embodiments, the XRPD pattern further comprises a peak at 11.1±0.2 degrees 2-theta or a peak at 19.2±0.2 degrees 2-theta.

In some embodiments, the compound of the invention is phentolamine mesylate that exhibits an XRPD pattern comprising a peak at 8.4±0.2 degrees 2-theta, a peak at 13.1±0.2 degrees 2-theta, a peak at 16.3±0.2 degrees 2-theta, a peak at 18.8±0.2 degrees 2-theta, a peak at 19.4±0.2 degrees 2-theta, a peak at 20.0±0.2 degrees 2-theta, and a peak at 20.8±0.2 degrees 2-theta. In some embodiments, the XRPD pattern further comprises a peak at 16.9±0.2 degrees 2-theta or a peak at 18.4±0.2 degrees 2-theta. In some embodiments, the XRPD pattern further comprises a peak at 8.9±0.2 degrees 2-theta or a peak at 22.2±0.2 degrees 2-theta. In some embodiments, the XRPD pattern further comprises a peak at 11.1±0.2 degrees 2-theta or a peak at 19.2±0.2 degrees 2-theta.

In some embodiments, the compound of the invention is phentolamine mesylate that exhibits an XRPD pattern comprising a peak at 8.4±0.2 degrees 2-theta, a peak at 13.1±0.2 degrees 2-theta, a peak at 16.3±0.2 degrees 2-theta, a peak at 19.4±0.2 degrees 2-theta, and a peak at 20.8±0.2 degrees 2-theta. In some embodiments, the XRPD pattern further comprises a peak at 8.9±0.2 degrees 2-theta, a peak at 10.3±0.2 degrees 2-theta, a peak at 10.9±0.2 degrees 2-theta, a peak at 11.1±0.2 degrees 2-theta, a peak at 16.9±0.2 degrees 2-theta, a peak at 18.4±0.2 degrees 2-theta, a peak at 18.8±0.2 degrees 2-theta, a peak at 19.2±0.2 degrees 2-theta, a peak at 20.0±0.2 degrees 2-theta or a peak at 22.2±0.2 degrees 2-theta. In some embodiments, the XRPD pattern further comprises a peak at 8.9±0.2 degrees 2-theta, a peak at 10.3±0.2 degrees 2-theta, a peak at 10.9±0.2 degrees 2-theta, a peak at 11.1±0.2 degrees 2-theta, a peak at 16.9±0.2 degrees 2-theta, a peak at 18.4±0.2 degrees 2-theta, a peak at 18.8±0.2 degrees 2-theta, a peak at 19.2±0.2 degrees 2-theta, a peak at 20.0±0.2 degrees 2-theta and a peak at 22.2±0.2 degrees 2-theta.

In some embodiments, the compound of the invention is phentolamine mesylate that exhibits an XRPD pattern comprising a peak at 8.4±0.2 degrees 2-theta and a peak at 16.3±0.2 degrees 2-theta, wherein the peak at 8.4±0.2 degrees 2-theta and the peak at 16.3±0.2 degrees 2-theta have a relative peak intensity (%) of greater than 10%. In some embodiments, the XRPD pattern further comprises a peak at 13.1±0.2 degrees 2-theta, a peak at 19.4±0.2 degrees 2-theta, or a peak at 20.8±0.2 degrees 2-theta, wherein the peak at 8.4±0.2 degrees 2-theta, the peak at 19.4±0.2 degrees 2-theta, or the peak at 20.8±0.2 degrees 2-theta has a relative peak intensity (%) of greater than 30%. In some embodiments, the XRPD pattern further comprises a peak at 18.8±0.2 degrees 2-theta or a peak at 20.0±0.2 degrees 2-theta, wherein the peak at 18.8±0.2 degrees 2-theta or the peak at 20.0±0.2 degrees 2-theta has a relative peak intensity (%) of greater than 40%. In some embodiments, the XRPD pattern further comprises a peak at 16.9±0.2 degrees 2-theta or a peak at 18.4±0.2 degrees 2-theta, wherein the peak at 16.9±0.2 degrees 2-theta or the peak at 18.4±0.2 degrees 2-theta has a relative peak intensity (%) of greater than 30%. In some embodiments, the XRPD pattern further comprises a peak at 8.9±0.2 degrees 2-theta or a peak at 22.2±0.2 degrees 2-theta, wherein the peak at 8.9±0.2 degrees 2-theta or the peak at 22.2±0.2 degrees 2-theta has a relative peak intensity (%) of greater than 20%. In some embodiments, the XRPD pattern further comprises a peak at 11.1±0.2 degrees 2-theta or a peak at 19.2±0.2 degrees 2-theta, wherein the peak at 11.1±0.2 degrees 2-theta or the peak at 19.2±0.2 degrees 2-theta has a relative peak intensity (%) of greater than 10%.

In some embodiments, the compound of the invention is phentolamine mesylate that exhibits an XRPD pattern comprising a peak at 16.3±0.2 degrees 2-theta. In some embodiments, the peak at 16.3±0.2 degrees 2-theta has a relative peak intensity (%) of greater than 10%. In some embodiments, the peak at 16.3±0.2 degrees 2-theta has a relative peak intensity (%) of greater than 15%.

In some embodiments, the compound of the invention is phentolamine mesylate that exhibits an XRPD pattern comprising a peak at 13.1±0.2 degrees 2-theta, wherein the peak at 13.1±0.2 degrees 2-theta has a relative peak intensity (%) of greater than 75%. In some embodiments, the peak at 13.1±0.2 degrees 2-theta has a relative peak intensity (%) of greater than 80%. In some embodiments, the peak at 13.1±0.2 degrees 2-theta is the XRPD pattern's most intense peak.

In some embodiments, the compound of the invention is phentolamine mesylate that exhibits an XRPD pattern comprising a peak at 8.4±0.2 degrees 2-theta and a peak at 16.3±0.2 degrees 2-theta, wherein the peak at 8.4±0.2 degrees 2-theta has a relative peak intensity (%) of greater than 30% and the peak at 16.3±0.2 degrees 2-theta has a relative peak intensity (%) of greater than 10%.

In some embodiments, the compound of the invention is phentolamine mesylate that exhibits an XRPD pattern comprising a peak at 8.4±0.2 degrees 2-theta and 1 other peak, 2 other peaks, 3 other peaks, 4 other peaks, 5 other peaks, 6 other peaks, 7 other peaks, 8 other peaks, or 9 other peaks of Table 3. In some embodiments, the phentolamine mesylate exhibits an XRPD pattern comprising a peak at 8.4±0.2 degrees 2-theta and 1 peak, 2 peaks, 3 peaks, 4 peaks, 5 peaks, 6 peaks, 7 peaks, 8 peaks, 9 peaks or 10 peaks of the following peaks: a peak at 8.9±0.2 degrees 2-theta, a peak at 13.1±0.2 degrees 2-theta, a peak at 16.3±0.2 degrees 2-theta, a peak at 16.9±0.2 degrees 2-theta, a peak at 18.4±0.2 degrees 2-theta, a peak at 18.8±0.2 degrees 2-theta, a peak at 19.4±0.2 degrees 2-theta, a peak at 20.0±0.2 degrees 2-theta, a peak at 20.8±0.2 degrees 2-theta, and a peak at 22.2±0.2 degrees 2-theta.

In some embodiments, the phentolamine mesylate exhibits an XRPD pattern comprising a Table 3 peak having a relative peak intensity (%) of greater than 50%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 20%. In some embodiments, the phentolamine mesylate exhibits an XRPD pattern comprising a Table 3 peak having a relative peak intensity (%) of greater than 15%. In some embodiments, the phentolamine mesylate exhibits an XRPD pattern comprising a Table 3 peak having a relative peak intensity (%) of greater than 10%.

Figure 2A:
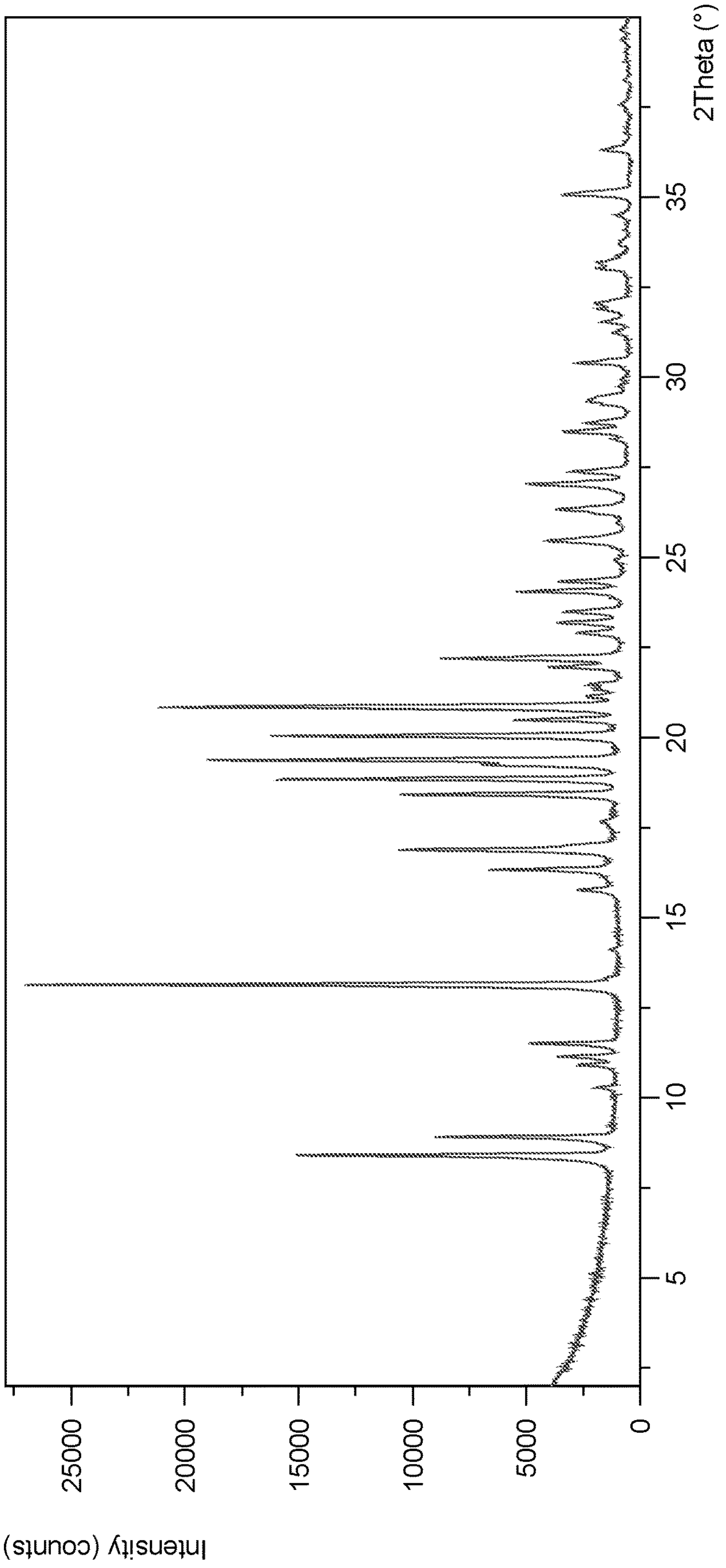
FIG. 2A shows an XRPD pattern of the phentolamine mesylate obtained as described in Example 1.

In some embodiments, the phentolamine mesylate exhibits an XRPD pattern that is substantially the same as that depicted in FIG. 2A.

In some embodiments, the phentolamine mesylate exhibits a DSC thermogram comprising an endothermic peak having a peak maximum at a temperature of from about 110° C. to about 130° C. In some embodiments, the phentolamine mesylate exhibits a DSC thermogram comprising an endothermic peak having a peak maximum at a temperature of from about 115° C. to about 125° C. In some embodiments, the phentolamine mesylate exhibits a DSC thermogram comprising an endothermic peak having a peak maximum at a temperature of about 120° C.

In some embodiments, the phentolamine mesylate exhibits a DSC thermogram comprising an endothermic peak having a peak maximum at a temperature of from about 120° C. to about 140° C. In some embodiments, the phentolamine mesylate exhibits a DSC thermogram comprising an endothermic peak having a peak maximum at a temperature of from about 125° C. to about 135° C. In some embodiments, the phentolamine mesylate exhibits a DSC thermogram comprising an endothermic peak having a peak maximum at a temperature of about 133° C.

In some embodiments, the phentolamine mesylate exhibits a DSC thermogram comprising an endothermic peak having a peak maximum at a temperature of from about 170° C. to about 190° C. In some embodiments, the phentolamine mesylate exhibits a DSC thermogram comprising an endothermic peak having a peak maximum at a temperature of from about 175° C. to about 185° C. In some embodiments, the phentolamine mesylate exhibits a DSC thermogram comprising an endothermic peak having a peak maximum at a temperature of about 180° C.

Figure 2B:
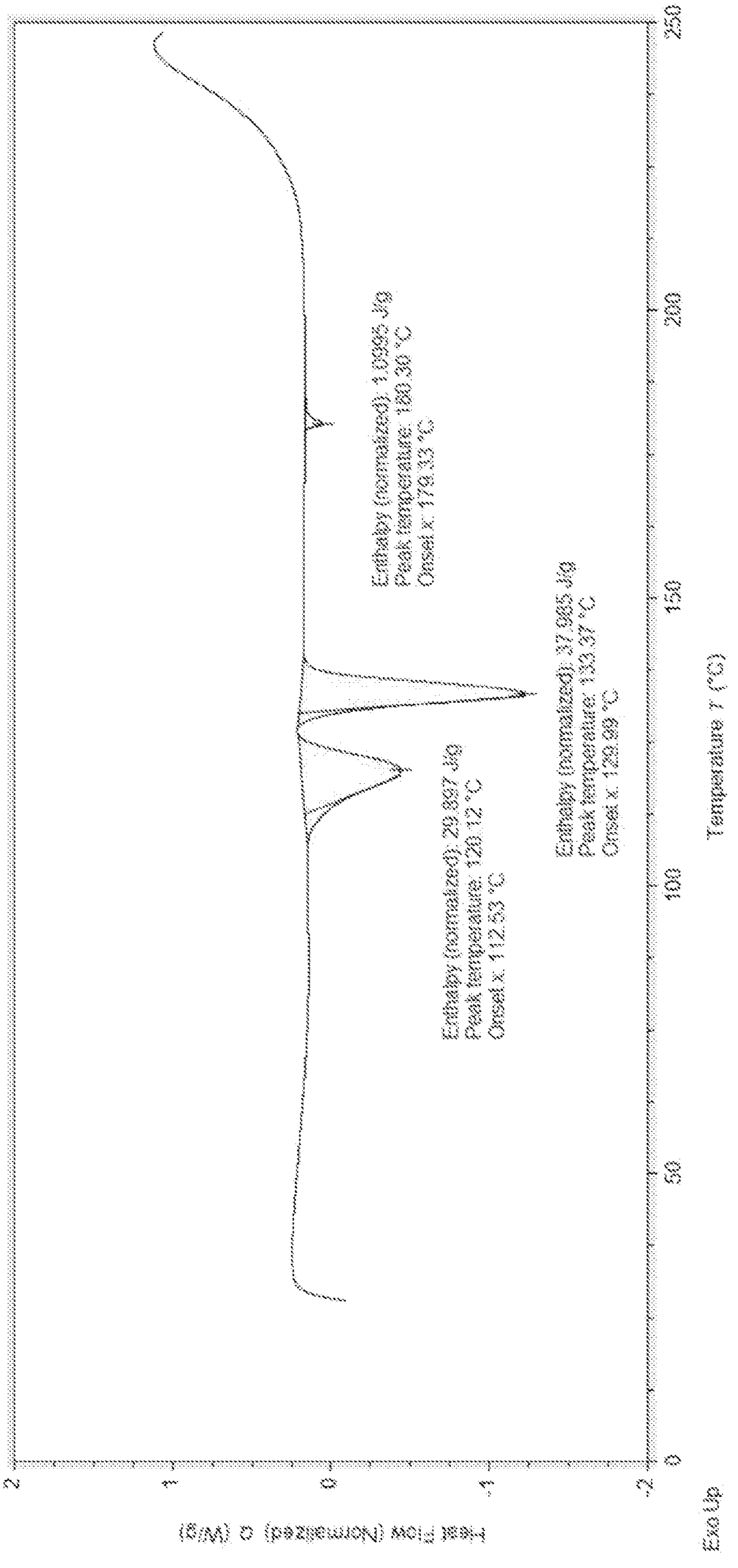
FIG. 2B shows a DSC thermogram of the phentolamine mesylate obtained as described in Example 1.

In some embodiments, the phentolamine mesylate exhibits a DSC thermogram that is substantially the same as that depicted in FIG. 2B.

In some embodiments, the compound of the invention is phentolamine mesylate obtained according to Example 1.

In some embodiments, the phentolamine mesylate obtained according to Example 1 is at least about 95% pure by weight. In some embodiments, the phentolamine mesylate obtained according to Example 1 is at least about 98% pure by weight. In some embodiments, the phentolamine mesylate obtained according to Example 1 is at least about 99% pure by weight.

In some embodiments, the phentolamine mesylate obtained according to Example 1 is at least about 90% pure by weight after being exposed to 25° C./60% relative humidity (RH) for 3 weeks. In some embodiments, the phentolamine mesylate obtained according to Example 1 is at least about 95% pure by weight after being exposed to 25° C./60% RH for 3 weeks. In some embodiments, the phentolamine mesylate obtained according to Example 1 is at least about 98% pure by weight after being exposed to 25° C./60% RH for 3 weeks.

In some embodiments, the compound of the invention is phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the XRPD pattern further comprises a peak at 16.7±0.2 degrees 2-theta or a peak at 20.3±0.2 degrees 2-theta. In some embodiments, the XRPD pattern further comprises a peak at 18.8±0.2 degrees 2-theta. In some embodiments, the XRPD pattern further comprises a peak at 18.9±0.2 degrees 2-theta. In some embodiments, the XRPD pattern further comprises a peak at 22.0±0.2 degrees 2-theta or a peak at 23.5±0.2 degrees 2-theta. In some embodiments, the XRPD pattern further comprises a peak at 11.3±0.2 degrees 2-theta or a peak at 19.1±0.2 degrees 2-theta.

In some embodiments, the compound of the invention is phentolamine mesylate that exhibits an XRPD pattern comprising a peak at 8.3±0.2 degrees 2-theta, a peak at 13.3±0.2 degrees 2-theta, a peak at 16.7±0.2 degrees 2-theta, a peak at 19.7±0.2 degrees 2-theta, and a peak at 20.3±0.2 degrees 2-theta. In some embodiments, the XRPD pattern further comprises a peak at 18.8±0.2 degrees 2-theta. In some embodiments, the XRPD pattern further comprises a peak at 18.9±0.2 degrees 2-theta. In some embodiments, the XRPD pattern further comprises a peak at 22.0±0.2 degrees 2-theta or a peak at 23.5±0.2 degrees 2-theta. In some embodiments, the XRPD pattern further comprises a peak at 11.3±0.2 degrees 2-theta or a peak at 19.1±0.2 degrees 2-theta.

In some embodiments, the compound of the invention is phentolamine mesylate that exhibits an XRPD pattern comprising a peak at 8.3±0.2 degrees 2-theta, a peak at 13.3±0.2 degrees 2-theta, a peak at 18.8±0.2 degrees 2-theta, and a peak at 19.7±0.2 degrees 2-theta. In some embodiments, the XRPD pattern further comprises a peak at 16.7±0.2 degrees 2-theta or a peak at 20.3±0.2 degrees 2-theta. In some embodiments, the XRPD pattern further comprises a peak at 18.9±0.2 degrees 2-theta. In some embodiments, the XRPD pattern further comprises a peak at 22.0±0.2 degrees 2-theta or a peak at 23.5±0.2 degrees 2-theta. In some embodiments, the XRPD pattern further comprises a peak at 11.3±0.2 degrees 2-theta or a peak at 19.1±0.2 degrees 2-theta.

In some embodiments, the compound of the invention is phentolamine mesylate that exhibits an XRPD pattern comprising a peak at 8.3±0.2 degrees 2-theta, a peak at 13.3±0.2 degrees 2-theta, a peak at 19.7±0.2 degrees 2-theta, a peak at 22.0±0.2 degrees 2-theta, and a peak at 23.5±0.2 degrees 2-theta. In some embodiments, the XRPD pattern further comprises a peak at 16.7±0.2 degrees 2-theta or a peak at 20.3±0.2 degrees 2-theta. In some embodiments, the XRPD pattern further comprises a peak at 18.8±0.2 degrees 2-theta. In some embodiments, the XRPD pattern further comprises a peak at 18.9±0.2 degrees 2-theta. In some embodiments, the XRPD pattern further comprises a peak at 11.3±0.2 degrees 2-theta or a peak at 19.1±0.2 degrees 2-theta.

In some embodiments, the compound of the invention is phentolamine mesylate that exhibits an XRPD pattern comprising a peak at 8.3±0.2 degrees 2-theta, a peak at 13.3±0.2 degrees 2-theta, a peak at 16.7±0.2 degrees 2-theta, a peak at 18.8±0.2 degrees 2-theta, a peak at 19.7±0.2 degrees 2-theta, and a peak at 20.3±0.2 degrees 2-theta. In some embodiments, the XRPD pattern further comprises a peak at 18.9±0.2 degrees 2-theta. In some embodiments, the XRPD pattern further comprises a peak at 22.0±0.2 degrees 2-theta or a peak at 23.5±0.2 degrees 2-theta. In some embodiments, the XRPD pattern further comprises a peak at 11.3±0.2 degrees 2-theta or a peak at 19.1±0.2 degrees 2-theta.

In some embodiments, the XRPD pattern comprising a peak at 8.3±0.2 degrees 2-theta, a peak at 13.3±0.2 degrees 2-theta and a peak at 19.7±0.2 degrees 2-theta does not comprise a peak at 6.9±0.2 degrees 2-theta or a peak at 11.6±0.2 degrees 2-theta. In some embodiments, the XRPD pattern comprising a peak at 8.3±0.2 degrees 2-theta, a peak at 13.3±0.2 degrees 2-theta and a peak at 19.7±0.2 degrees 2-theta does not comprise a peak at 6.9±0.2 degrees 2-theta and a peak at 11.6±0.2 degrees 2-theta.

In some embodiments, the compound of the invention is phentolamine mesylate that exhibits an XRPD pattern comprising a peak at a peak at 8.3±0.2 degrees 2-theta, a peak at 11.6±0.2 degrees 2-theta, a peak at 13.3±0.2 degrees 2-theta, a peak at 16.7±0.2 degrees 2-theta, and a peak at 19.7±0.2 degrees 2-theta. In some embodiments, the XRPD pattern further comprises a peak at 9.0±0.2 degrees 2-theta, a peak at 10.3±0.2 degrees 2-theta, a peak at 11.3±0.2 degrees 2-theta, a peak at 18.9±0.2 degrees 2-theta, a peak at 19.1±0.2 degrees 2-theta, a peak at 20.3±0.2 degrees 2-theta, a peak at 22.0±0.2 degrees 2-theta, or a peak at 23.5±0.2 degrees 2-theta. In some embodiments, the XRPD pattern further comprises a peak at 9.0±0.2 degrees 2-theta, a peak at 10.3±0.2 degrees 2-theta, a peak at 11.3±0.2 degrees 2-theta, a peak at 18.9±0.2 degrees 2-theta, a peak at 19.1±0.2 degrees 2-theta, a peak at 20.3±0.2 degrees 2-theta, a peak at 22.0±0.2 degrees 2-theta, and a peak at 23.5±0.2 degrees 2-theta.

In some embodiments, the compound of the invention is phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta, wherein the peak at 8.3±0.2 degrees 2-theta, the peak at 13.3±0.2 degrees 2-theta and the peak at 19.7±0.2 degrees 2-theta have a relative peak intensity (%) of greater than 40%. In some embodiments, the XRPD pattern further comprises a peak at 16.7±0.2 degrees 2-theta or a peak at 20.3±0.2 degrees 2-theta, wherein the peak at 16.7±0.2 degrees 2-theta or the peak at 20.3±0.2 degrees 2-theta has a relative peak intensity (%) of greater than 30%. In some embodiments, the XRPD pattern further comprises a peak at 18.8±0.2 degrees 2-theta, wherein the peak at 18.8±0.2 degrees 2-theta has a relative peak intensity (%) of greater than 30%. In some embodiments, the XRPD pattern further comprises a peak at 18.9±0.2 degrees 2-theta, wherein the peak at 18.9±0.2 degrees 2-theta has a relative peak intensity (%) of greater than 30%. In some embodiments, the XRPD pattern further comprises a peak at 22.0±0.2 degrees 2-theta or a peak at 23.5±0.2 degrees 2-theta, wherein the peak at 22.0±0.2 degrees 2-theta or the peak at 23.5±0.2 degrees 2-theta has a relative peak intensity (%) of greater than 10%. In some embodiments, the XRPD pattern further comprises a peak at 11.3±0.2 degrees 2-theta or a peak at 19.1±0.2 degrees 2-theta, wherein the peak at 11.3±0.2 degrees 2-theta or the peak at 19.1±0.2 degrees 2-theta has a relative peak intensity (%) of greater than 10%.

In some embodiments, the compound of the invention is phentolamine mesylate that exhibits an XRPD pattern comprising a peak at 8.3±0.2 degrees 2-theta and a peak at 19.7±0.2 degrees 2-theta, wherein the peak at 19.7±0.2 degrees 2-theta has a relative peak intensity (%) of greater than 30%. In some embodiments, the peak at 19.7±0.2 degrees 2-theta has a relative peak intensity (%) of greater than 40%.

In some embodiments, the compound of the invention is phentolamine mesylate that exhibits an XRPD pattern comprising a peak at 8.3±0.2 degrees 2-theta, wherein the peak at 8.3±0.2 degrees 2-theta has a relative peak intensity (%) of greater than 70%. In some embodiments, the peak at 8.3±0.2 degrees 2-theta has a relative peak intensity (%) of greater than 80%. In some embodiments, the peak at 8.3±0.2 degrees 2-theta is the XRPD pattern's most intense peak.

In some embodiments, the compound of the invention is phentolamine mesylate that exhibits an XRPD pattern comprising a peak at 8.3±0.2 degrees 2-theta and a peak at 13.3±0.2 degrees 2-theta, wherein the peak at 8.3±0.2 degrees 2-theta and the peak at 13.3±0.2 degrees 2-theta have a relative peak intensity (%) of greater than 55%. In some embodiments, the compound of the invention is phentolamine mesylate that exhibits an XRPD pattern comprising a peak at 8.3±0.2 degrees 2-theta and a peak at 13.3±0.2 degrees 2-theta, wherein the peak at 8.3±0.2 degrees 2-theta and the peak at 13.3±0.2 degrees 2-theta have a relative peak intensity (%) of greater than 65%.

In some embodiments, the compound of the invention is phentolamine mesylate that exhibits an XRPD pattern comprising a peak at 8.3±0.2 degrees 2-theta, a peak at 13.3±0.2 degrees 2-theta, a peak at 19.7±0.2 degrees 2-theta and 1 other peak, 2 other peaks, 3 other peaks, 4 other peaks, 5 other peaks, 6 other peaks, 7 other peaks, 8 other peaks, or 9 other peaks of Table 4. In some embodiments, the phentolamine mesylate exhibits an XRPD pattern comprising a peak at 8.3±0.2 degrees 2-theta, a peak at 13.3±0.2 degrees 2-theta, and a peak at 19.7±0.2 degrees 2-theta, and 1 peak, 2 peaks, 3 peaks, 4 peaks, 5 peaks, 6 peaks, 7 peaks, or 8 peaks of the following peaks: a peak at 11.3±0.2 degrees 2-theta, a peak at 16.7±0.2 degrees 2-theta, a peak at 18.8±0.2 degrees 2-theta, a peak at 18.9±0.2 degrees 2-theta, a peak at 19.1±0.2 degrees 2-theta, a peak at 20.3±0.2 degrees 2-theta, a peak at 22.0±0.2 degrees 2-theta, and a peak at 23.5±0.2 degrees 2-theta.

In some embodiments, the phentolamine mesylate exhibits an XRPD pattern comprising a Table 4 peak having a relative peak intensity (%) of greater than 50%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 20%. In some embodiments, the phentolamine mesylate exhibits an XRPD pattern comprising a Table 4 peak having a relative peak intensity (%) of greater than 15%. In some embodiments, the phentolamine mesylate exhibits an XRPD pattern comprising a Table 4 peak having a relative peak intensity (%) of greater than 10%.

Figure 3A:
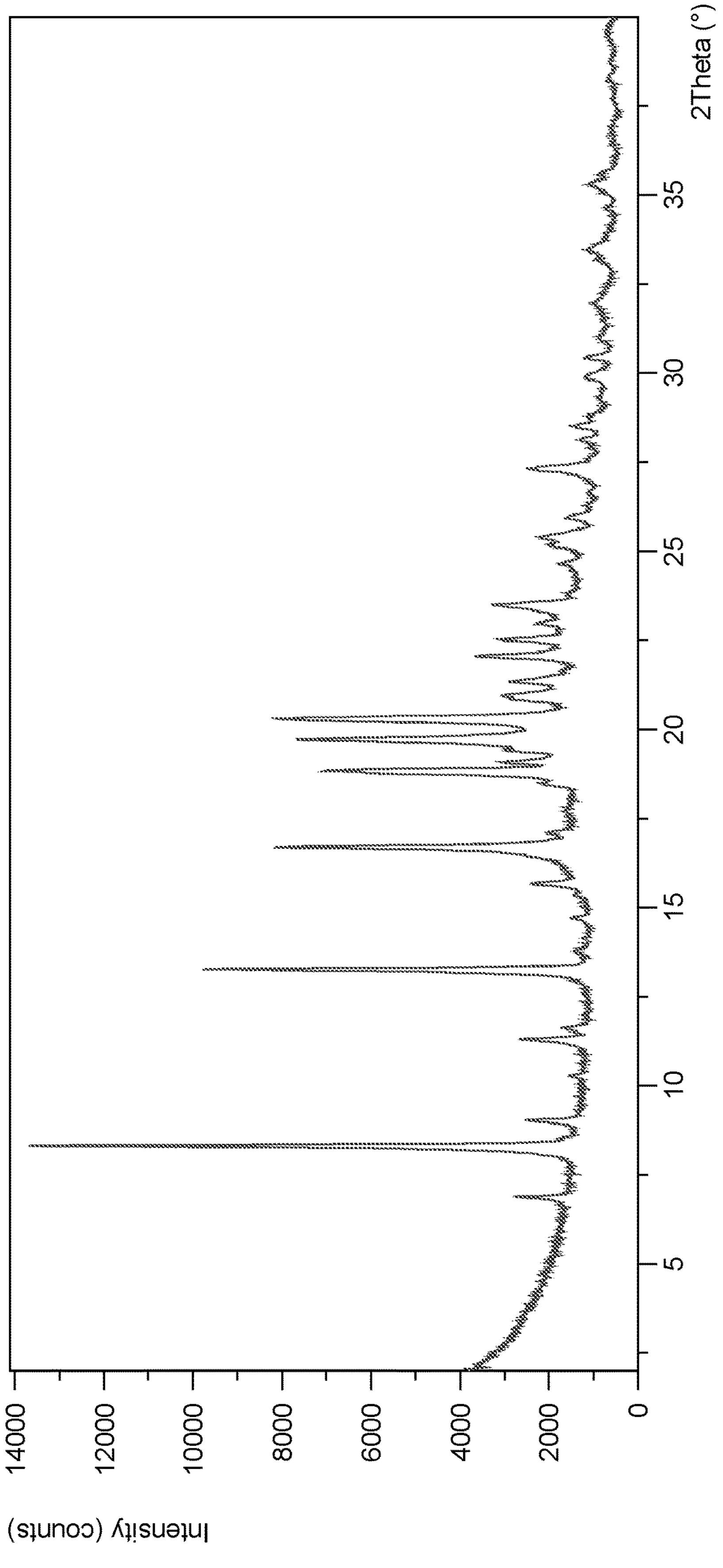
FIG. 3A shows an XRPD pattern of the phentolamine mesylate obtained as described in Example 2.

In some embodiments, the phentolamine mesylate exhibits an XRPD pattern that is substantially the same as that depicted in FIG. 3A.

In some embodiments, the phentolamine mesylate exhibits a DSC thermogram comprising an endothermic peak having a peak maximum at a temperature of from about 120° C. to about 140° C. In some embodiments, the phentolamine mesylate exhibits a DSC thermogram comprising an endothermic peak having a peak maximum at a temperature of from about 125° C. to about 135° C. In some embodiments, the phentolamine mesylate exhibits a DSC thermogram comprising an endothermic peak having a peak maximum at a temperature of about 133° C.

In some embodiments, the phentolamine mesylate exhibits a DSC thermogram comprising an exothermic peak having a peak maximum at a temperature of from about 130° C. to about 150° C. In some embodiments, the phentolamine mesylate exhibits a DSC thermogram comprising an exothermic peak having a peak maximum at a temperature of from about 135° C. to about 140° C. In some embodiments, the phentolamine mesylate exhibits a DSC thermogram comprising an exothermic peak having a peak maximum at a temperature of about 138° C.

In some embodiments, the phentolamine mesylate exhibits a DSC thermogram comprising an endothermic peak having a peak maximum at a temperature of from about 170° C. to about 190° C. In some embodiments, the phentolamine mesylate exhibits a DSC thermogram comprising an endothermic peak having a peak maximum at a temperature of from about 175° C. to about 185° C. In some embodiments, the phentolamine mesylate exhibits a DSC thermogram comprising an endothermic peak having a peak maximum at a temperature of about 180° C.

Figure 3B:
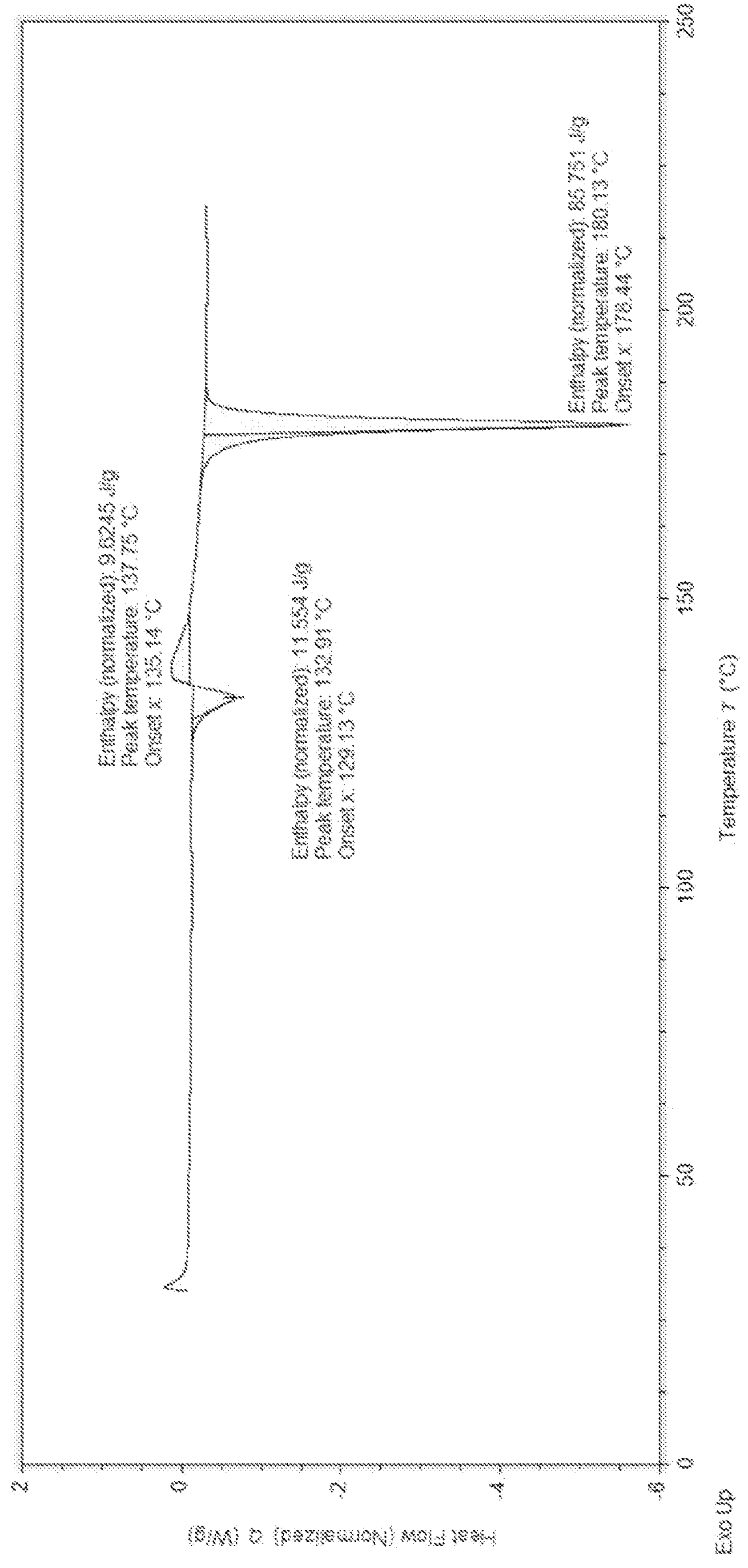
FIG. 3B shows a DSC thermogram of the phentolamine mesylate obtained as described in Example 2.

In some embodiments, the phentolamine mesylate exhibits a DSC thermogram that is substantially the same as that depicted in FIG. 3B.

In some embodiments, the compound of the invention is phentolamine mesylate obtained according to Example 2.

In some embodiments, the phentolamine mesylate obtained according to Example 2 is at least about 80% pure by weight. In some embodiments, the phentolamine mesylate obtained according to Example 2 is at least about 85% pure by weight. In some embodiments, the phentolamine mesylate obtained according to Example 2 is at least about 90% pure by weight. In some embodiments, the phentolamine mesylate obtained according to this Example 2 is at least about 95% pure by weight. In some embodiments, the phentolamine mesylate obtained according to Example 2 is at least about 98% pure by weight. In some embodiments, the phentolamine mesylate obtained according to Example 2 is at least about 99% pure by weight.

In some embodiments, the compound of the invention is phentolamine mesylate that exhibits an XRPD pattern comprising a peak at 7.1±0.2 degrees 2-theta, a peak at 8.9±0.2 degrees 2-theta, a peak at 13.0±0.2 degrees 2-theta, a peak at 15.1±0.2 degrees 2-theta, and a peak at 19.9±0.2 degrees 2-theta. In some embodiments, the XRPD pattern further comprises a peak at 11.8±0.2 degrees 2-theta, a peak at 17.8±0.2 degrees 2-theta, a peak at 19.0±0.2 degrees 2-theta, a peak at 20.2±0.2 degrees 2-theta, a peak at 21.0±0.2 degrees 2-theta, or a peak at 21.9±0.2 degrees 2-theta. In some embodiments, the XRPD pattern further comprises a peak at 11.8±0.2 degrees 2-theta, a peak at 17.8±0.2 degrees 2-theta, a peak at 19.0±0.2 degrees 2-theta, a peak at 20.2±0.2 degrees 2-theta, a peak at 21.0±0.2 degrees 2-theta, and a peak at 21.9±0.2 degrees 2-theta.

In some embodiments, the compound of the invention is phentolamine mesylate that exhibits an XRPD pattern comprising a peak at 15.1±0.2 degrees 2-theta and 1 other peak, 2 other peaks, 3 other peaks, 4 other peaks, 5 other peaks, 6 other peaks, 7 other peaks, 8 other peaks, or 9 other peaks of Table 5. In some embodiments, the phentolamine mesylate exhibits an XRPD pattern comprising a peak at 15.1±0.2 degrees 2-theta and 1 peak, 2 peaks, 3 peaks, 4 peaks, 5 peaks, 6 peaks, 7 peaks, 8 peaks, 9 peaks or 10 peaks of the following peaks: a peak at 7.1±0.2 degrees 2-theta, a peak at 8.9±0.2 degrees 2-theta, a peak at 11.8±0.2 degrees 2-theta, a peak at 13.0±0.2 degrees 2-theta, a peak at 17.8±0.2 degrees 2-theta, a peak at 19.0±0.2 degrees 2-theta, a peak at 19.9±0.2 degrees 2-theta, a peak at 20.2±0.2 degrees 2-theta, a peak at 21.0±0.2 degrees 2-theta, and a peak at 21.9±0.2 degrees 2-theta.

Figure 4A:
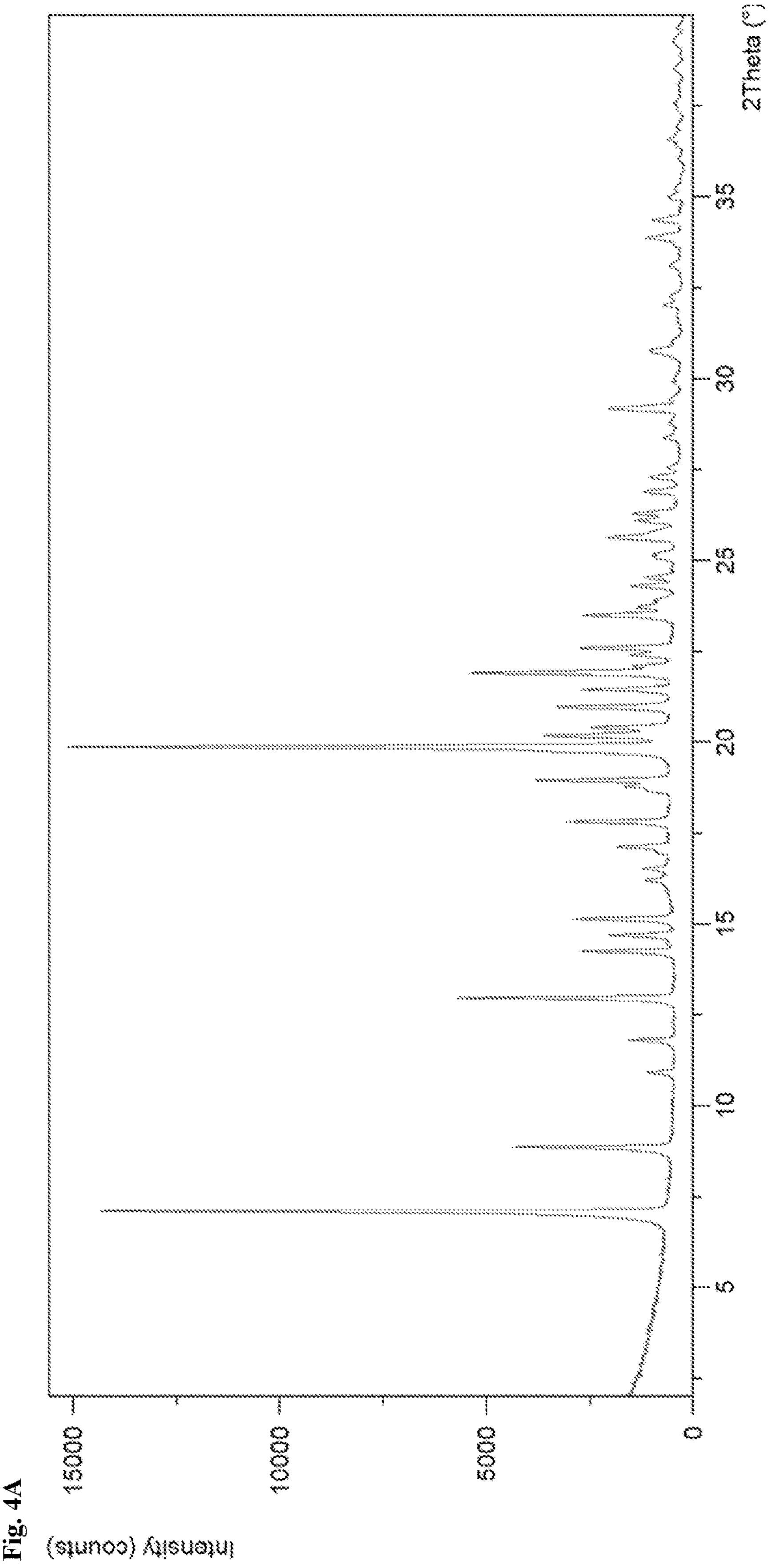
FIG. 4A shows an XRPD pattern of the phentolamine mesylate acetone solvate obtained as described in Example 3.

In some embodiments, the compound of the invention is phentolamine mesylate that exhibits an XRPD pattern that is substantially the same as that depicted in FIG. 4A.

In some embodiments, the phentolamine mesylate exhibits a DSC thermogram comprising an endothermic peak having a peak maximum at a temperature of from about 90° C. to about 110° C. In some embodiments, the phentolamine mesylate exhibits a DSC thermogram comprising an endothermic peak having a peak maximum at a temperature of from about 95° C. to about 105° C. In some embodiments, the phentolamine mesylate exhibits a DSC thermogram comprising an endothermic peak having a peak maximum at a temperature of about 100° C.

In some embodiments, the phentolamine mesylate exhibits a DSC thermogram comprising an endothermic peak having a peak maximum at a temperature of from about 170° C. to about 190° C. In some embodiments, the phentolamine mesylate exhibits a DSC thermogram comprising an endothermic peak having a peak maximum at a temperature of from about 175° C. to about 185° C. In some embodiments, the phentolamine mesylate exhibits a DSC thermogram comprising an endothermic peak having a peak maximum at a temperature of about 181° C.

Figure 4B:
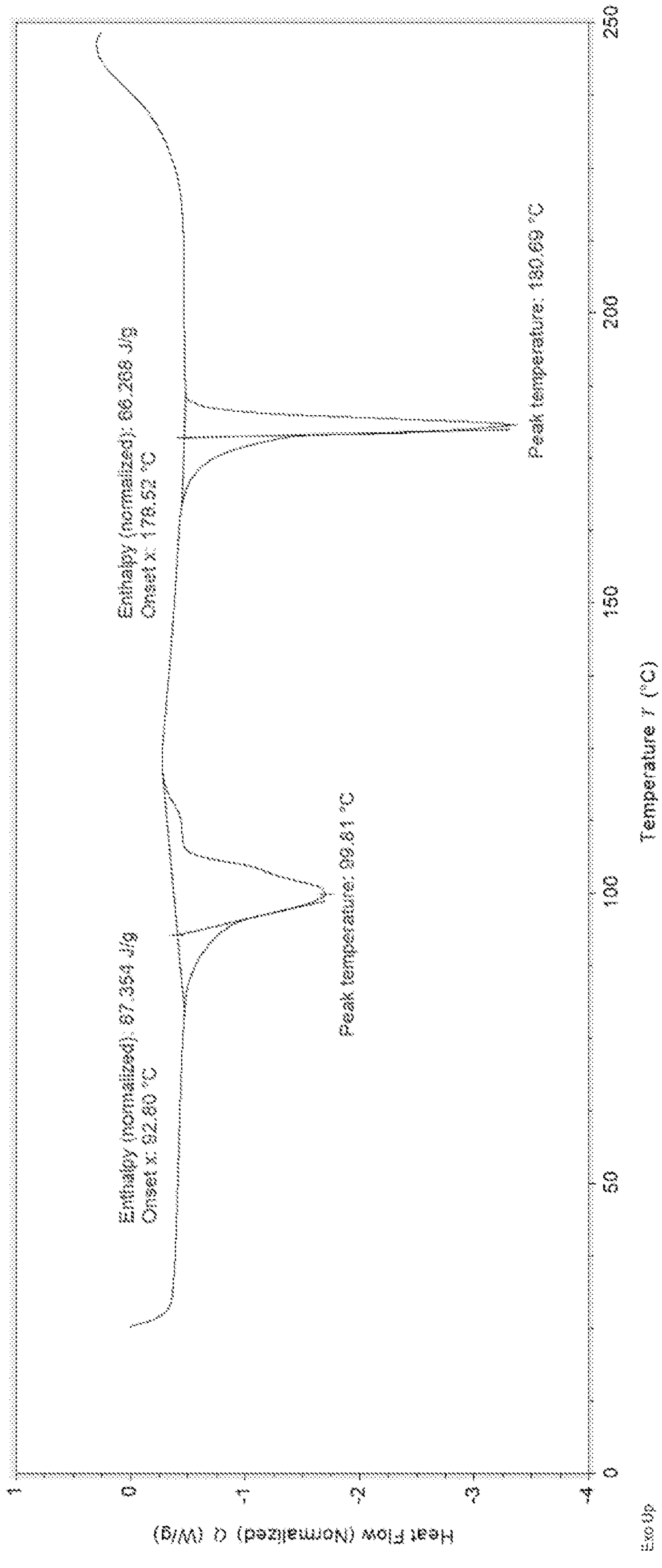
FIG. 4B shows a DSC thermogram of the phentolamine mesylate acetone solvate obtained as described in Example 3.

In some embodiments, the phentolamine mesylate exhibits a DSC thermogram that is substantially the same as that depicted in FIG. 4B.

Figure 4C:
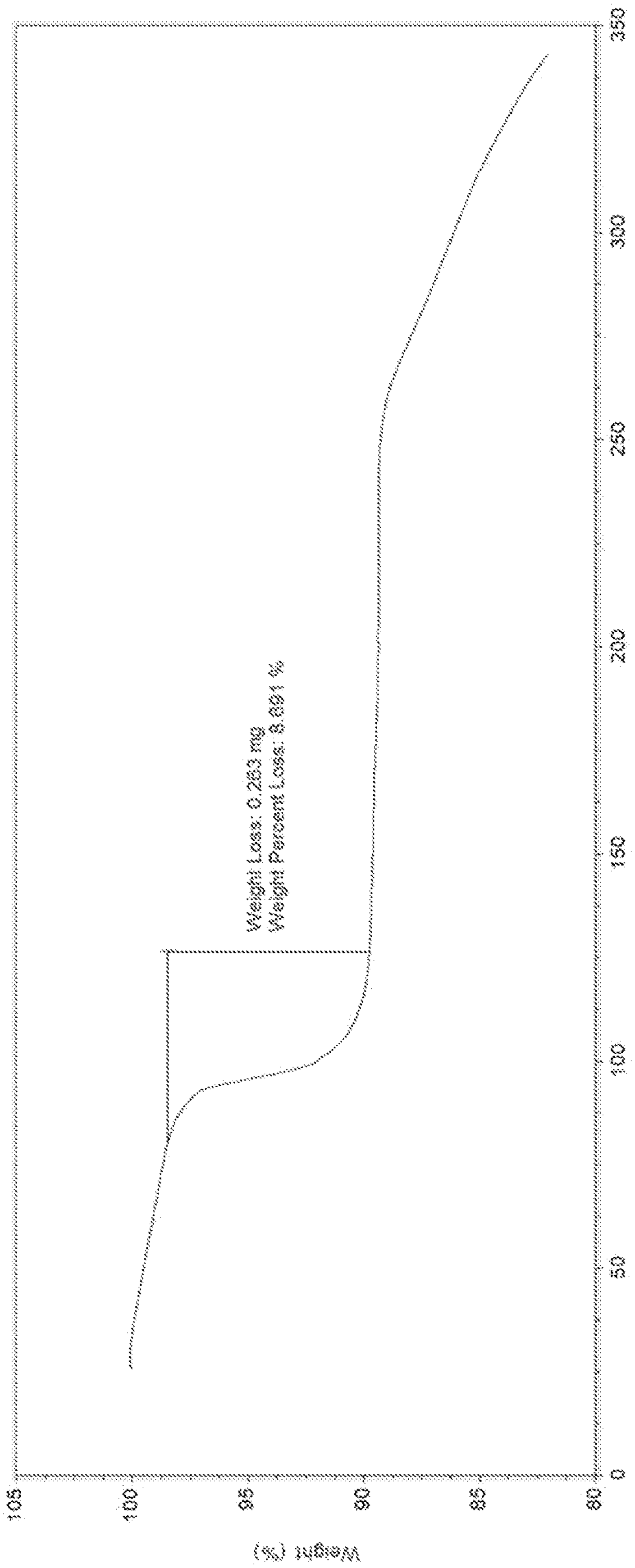
FIG. 4C shows a TG thermogram of the phentolamine mesylate acetone solvate obtained as described in Example 3.

In some embodiments, the phentolamine mesylate exhibits a TG curve that is substantially the same as that depicted in FIG. 4C.

Figure 4D:
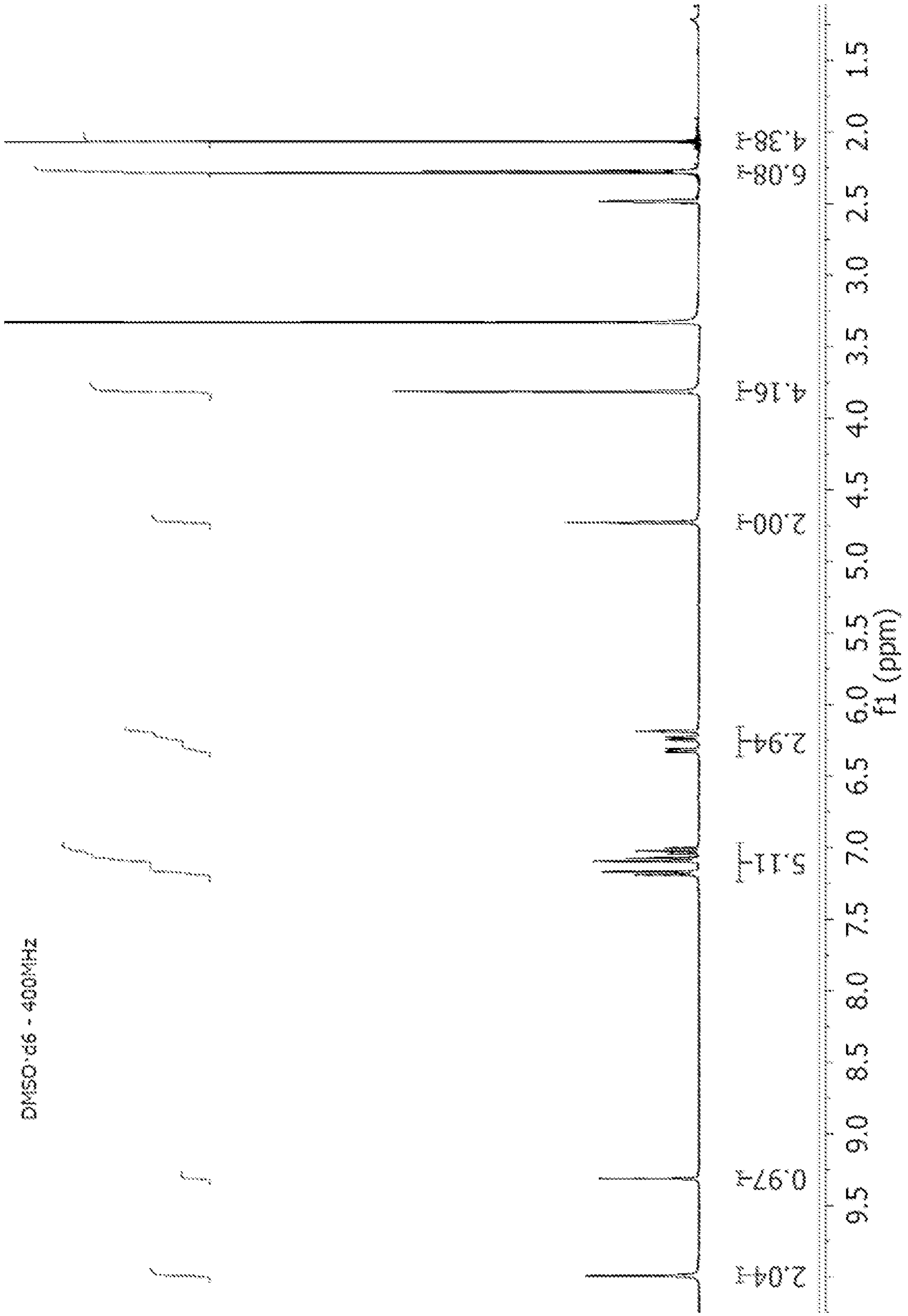
FIG. 4D shows a 1H NMR spectrum of the phentolamine mesylate acetone solvate obtained as described in Example 3.

In some embodiments, the phentolamine mesylate exhibits a $^{1}$H-NMR spectrum that is substantially the same as that depicted in FIG. 4D.

In some embodiments, the compound of the invention is phentolamine mesylate obtained according to Example 3.

Figure 5A:
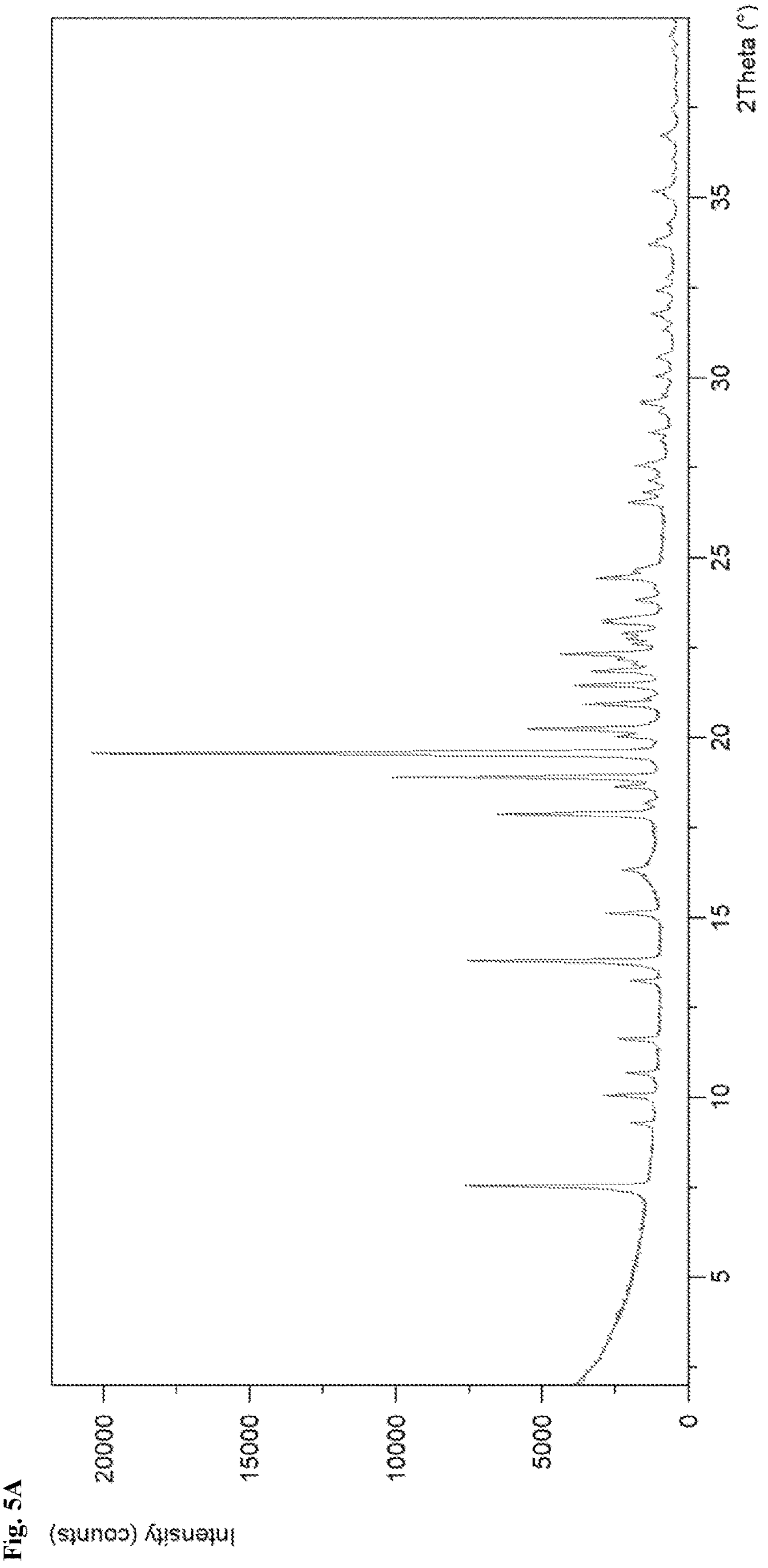
FIG. 5A shows an XRPD pattern of the phentolamine mesylate obtained as described in Example 4.

In some embodiments, the compound of the invention is phentolamine mesylate that exhibits an XRPD pattern that is substantially the same as that depicted in FIG. 5A.

In some embodiments, the phentolamine mesylate exhibits a DSC thermogram comprising an endothermic peak having a peak maximum at a temperature of from about 45° C. to about 50° C. In some embodiments, the phentolamine mesylate exhibits a DSC thermogram comprising an endothermic peak having a peak maximum at a temperature of about 52° C.

In some embodiments, the phentolamine mesylate exhibits a DSC thermogram comprising an endothermic peak having a peak maximum at a temperature of from about 90° C. to about 105° C. In some embodiments, the phentolamine mesylate exhibits a DSC thermogram comprising an endothermic peak having a peak maximum at a temperature of about 99° C.

In some embodiments, the phentolamine mesylate exhibits a DSC thermogram comprising an endothermic peak having a peak maximum at a temperature of from about 110° C. to about 120° C. In some embodiments, the phentolamine mesylate exhibits a DSC thermogram comprising an endothermic peak having a peak maximum at a temperature of about 114° C.

In some embodiments, the phentolamine mesylate exhibits a DSC thermogram comprising an exothermic peak having a peak maximum at a temperature of from about 125° C. to about 145° C. In some embodiments, the phentolamine mesylate exhibits a DSC thermogram comprising an exothermic peak having a peak maximum at a temperature of from about 130° C. to about 140° C. In some embodiments, the phentolamine mesylate exhibits a DSC thermogram comprising an exothermic peak having a peak maximum at a temperature of about 133° C.

In some embodiments, the phentolamine mesylate exhibits a DSC thermogram comprising an endothermic peak having a peak maximum at a temperature of from about 170° C. to about 190° C. In some embodiments, the phentolamine mesylate exhibits a DSC thermogram comprising an endothermic peak having a peak maximum at a temperature of from about 175° C. to about 185° C. In some embodiments, the phentolamine mesylate exhibits a DSC thermogram comprising an endothermic peak having a peak maximum at a temperature of about 180° C.

Figure 5B:
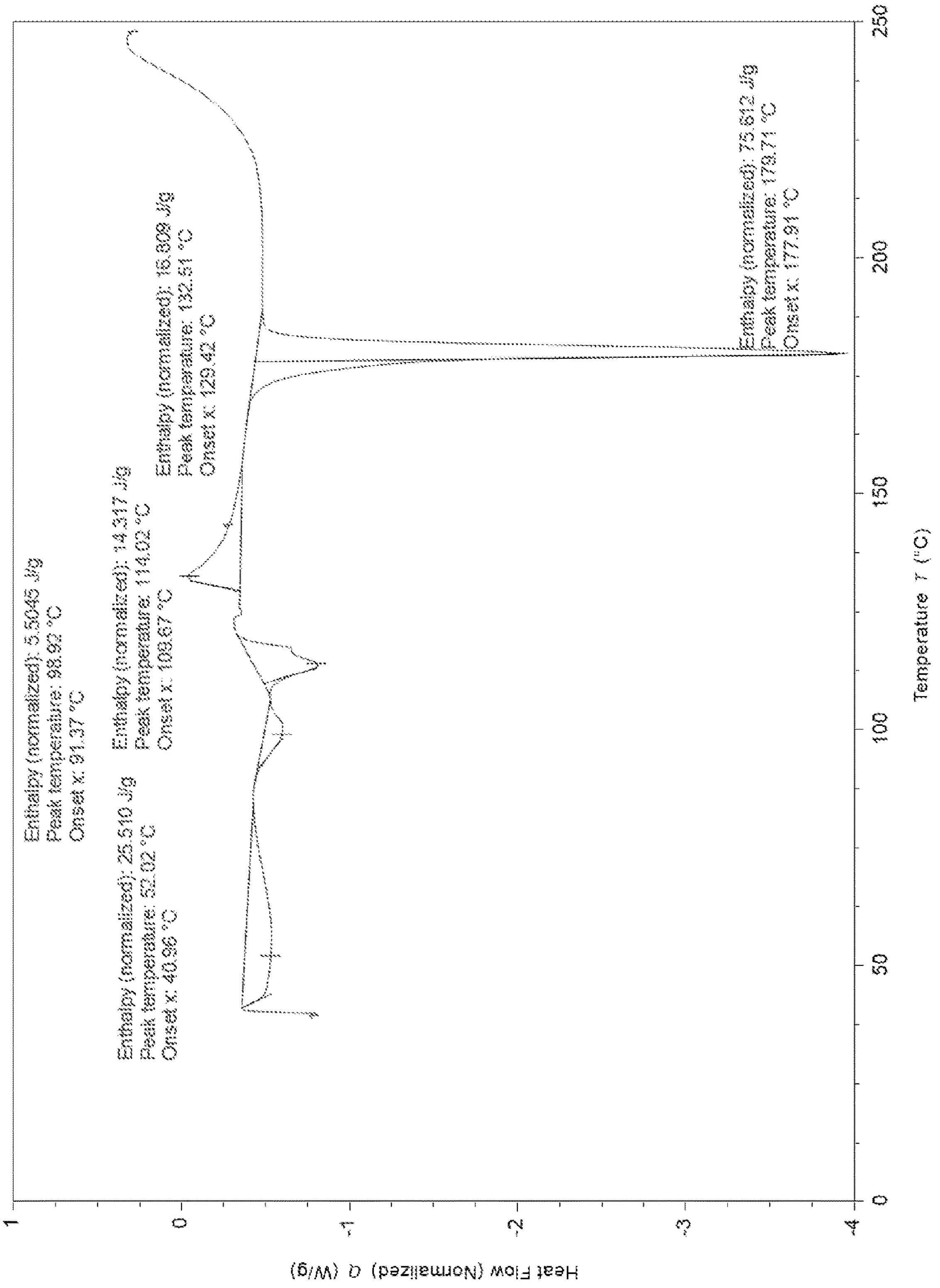
FIG. 5B shows a DSC thermogram of the phentolamine mesylate obtained as described in Example 4.

In some embodiments, the phentolamine mesylate exhibits a DSC thermogram that is substantially the same as that depicted in FIG. 5B.

Figure 5C:
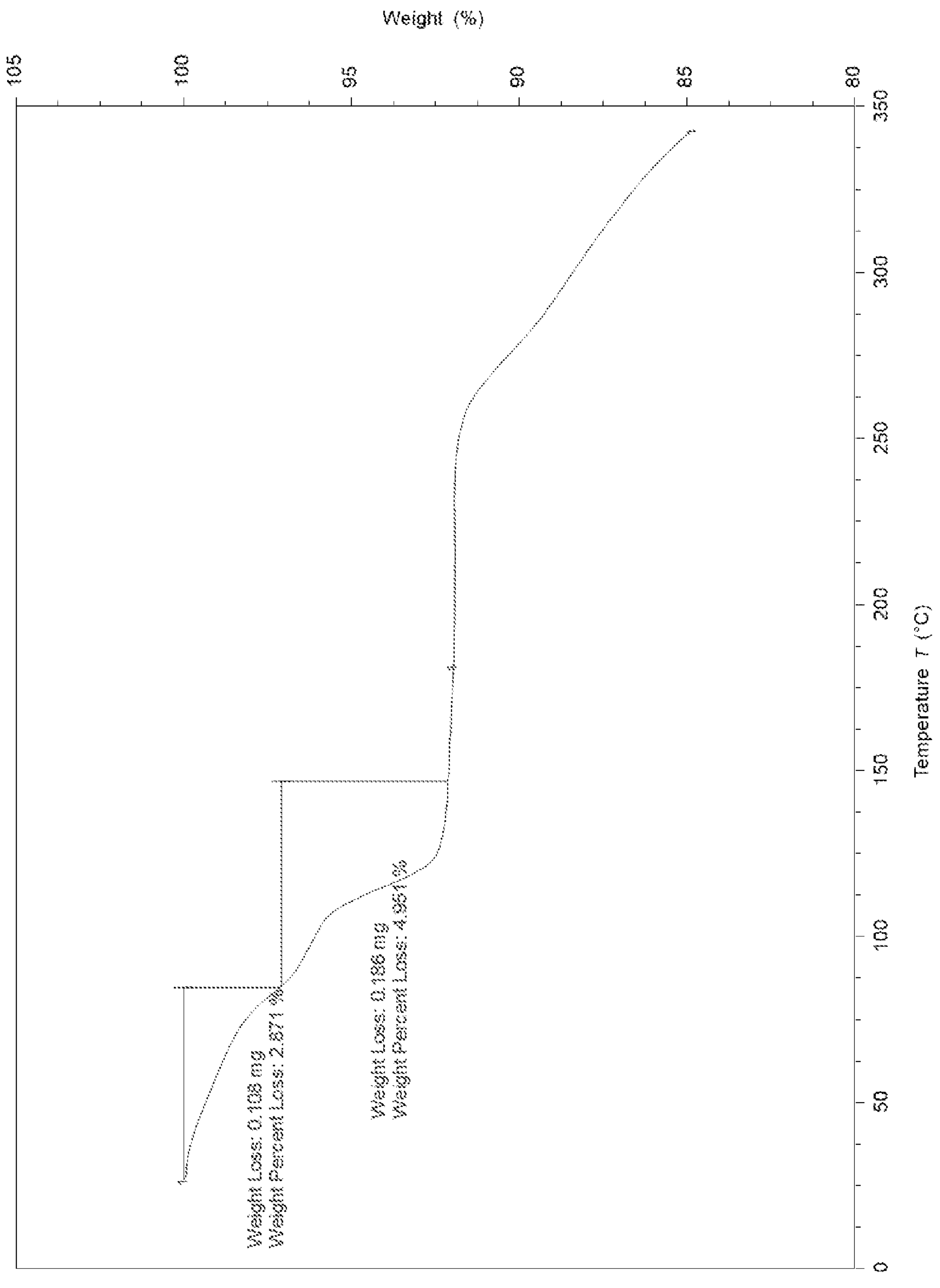
FIG. 5C shows a TG thermogram of the phentolamine mesylate obtained as described in Example 4.

In some embodiments, the phentolamine mesylate exhibits a TG curve that is substantially the same as that depicted in FIG. 5C.

In some embodiments, the compound of the invention is phentolamine mesylate obtained according to Example 4.

In some embodiments, the compound of the invention is phentolamine mesylate that exhibits an XRPD pattern comprising a peak at 7.4±0.2 degrees 2-theta, a peak at 13.1±0.2 degrees 2-theta, a peak at 19.8±0.2 degrees 2-theta, and a peak at 20.9±0.2 degrees 2-theta. In some embodiments, the XRPD pattern further comprises a peak at 9.2±0.2 degrees 2-theta, a peak at 10.8±0.2 degrees 2-theta, a peak at 14.7±0.2 degrees 2-theta, a peak at 15.8±0.2 degrees 2-theta, a peak at 18.4±0.2 degrees 2-theta, a peak at 19.5±0.2 degrees 2-theta, or a peak at 20.7±0.2 degrees 2-theta. In some embodiments, the XRPD pattern further comprises a peak at 9.2±0.2 degrees 2-theta, a peak at 10.8±0.2 degrees 2-theta, a peak at 14.7±0.2 degrees 2-theta, a peak at 15.8±0.2 degrees 2-theta, a peak at 18.4±0.2 degrees 2-theta, a peak at 19.5±0.2 degrees 2-theta, and a peak at 20.7±0.2 degrees 2-theta.

In some embodiments, the compound of the invention is phentolamine mesylate that exhibits an XRPD pattern comprising a peak at 7.4±0.2 degrees 2-theta and 1 other peak, 2 other peaks, 3 other peaks, 4 other peaks, 5 other peaks, 6 other peaks, 7 other peaks, 8 other peaks, or 9 other peaks of Table 6. In some embodiments, the phentolamine mesylate exhibits an XRPD pattern comprising a peak at 7.4±0.2 degrees 2-theta and 1 peak, 2 peaks, 3 peaks, 4 peaks, 5 peaks, 6 peaks, 7 peaks, 8 peaks, 9 peaks or 10 peaks of the following peaks: a peak at 9.2±0.2 degrees 2-theta, a peak at 10.8±0.2 degrees 2-theta, a peak at 13.1±0.2 degrees 2-theta, a peak at 14.7±0.2 degrees 2-theta, a peak at 15.8±0.2 degrees 2-theta, a peak at 18.4±0.2 degrees 2-theta, a peak at 19.5±0.2 degrees 2-theta, a peak at 19.8±0.2 degrees 2-theta, a peak at 20.7±0.2 degrees 2-theta, and a peak at 20.9±0.2 degrees 2-theta.

Figure 6A:
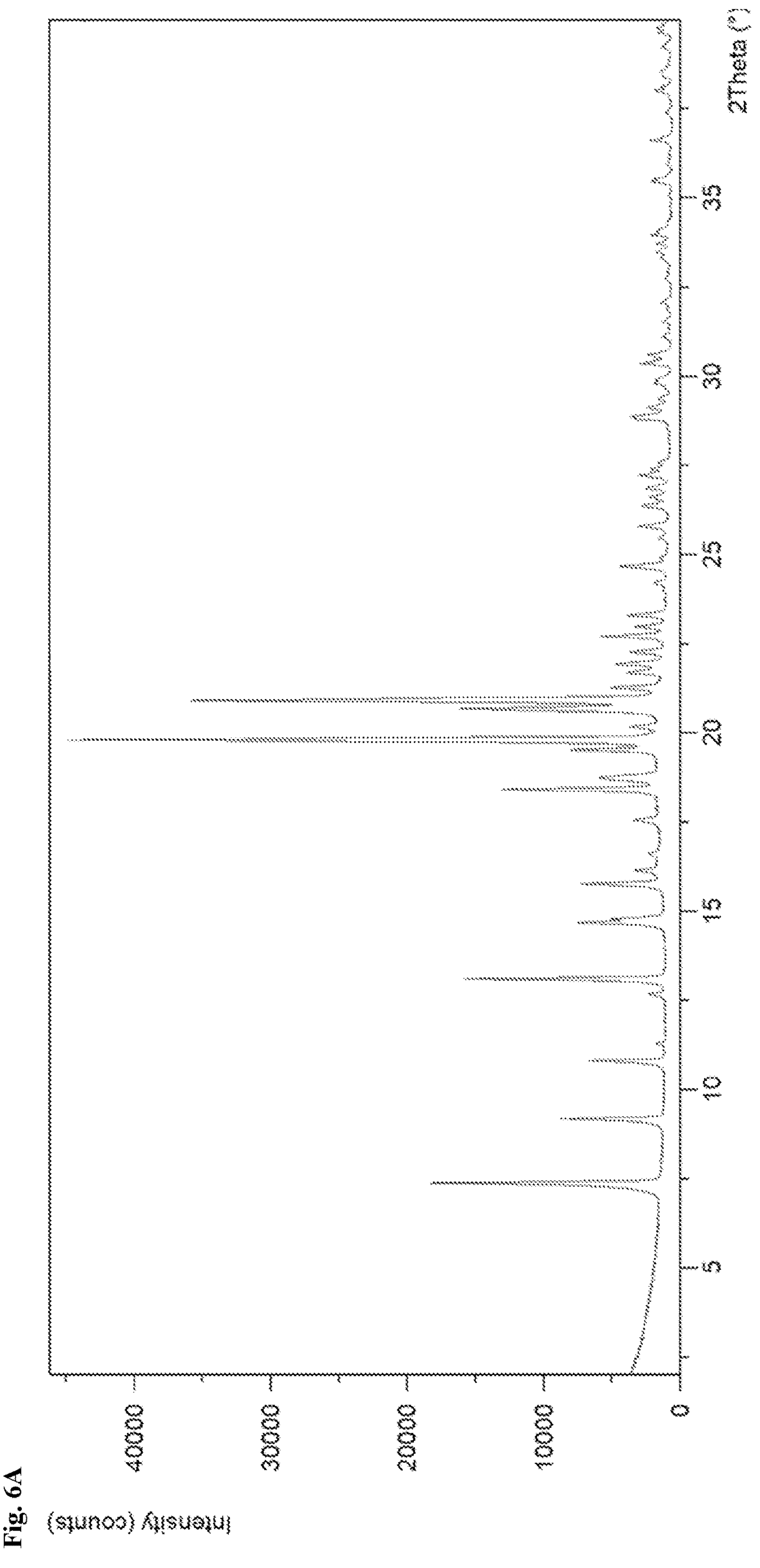
FIG. 6A shows an XRPD pattern of the phentolamine mesylate dioxane solvate obtained as described in Example 5.

In some embodiments, the compound of the invention is phentolamine mesylate that exhibits an XRPD pattern that is substantially the same as that depicted in FIG. 6A.

In some embodiments, the phentolamine mesylate exhibits a DSC thermogram comprising an endothermic peak having a peak maximum at a temperature of from about 130° C. to about 155° C. In some embodiments, the phentolamine mesylate exhibits a DSC thermogram comprising an endothermic peak having a peak maximum at a temperature of from about 140° C. to about 150° C. In some embodiments, the phentolamine mesylate exhibits a DSC thermogram comprising an endothermic peak having a peak maximum at a temperature of about 143° C.

Figure 6B:
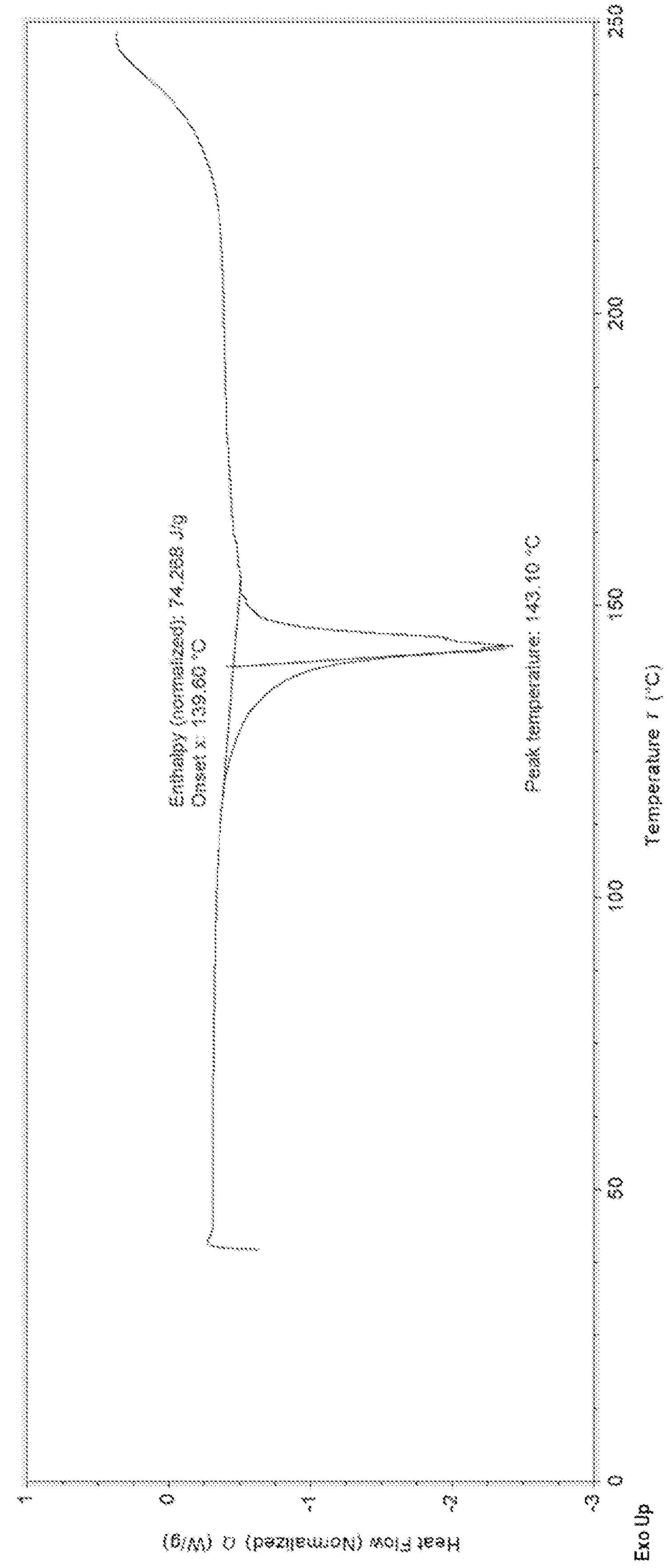
FIG. 6B shows a DSC thermogram of the phentolamine mesylate dioxane solvate obtained as described in Example 5.

In some embodiments, the phentolamine mesylate exhibits a DSC thermogram that is substantially the same as that depicted in FIG. 6B.

Figure 6C:
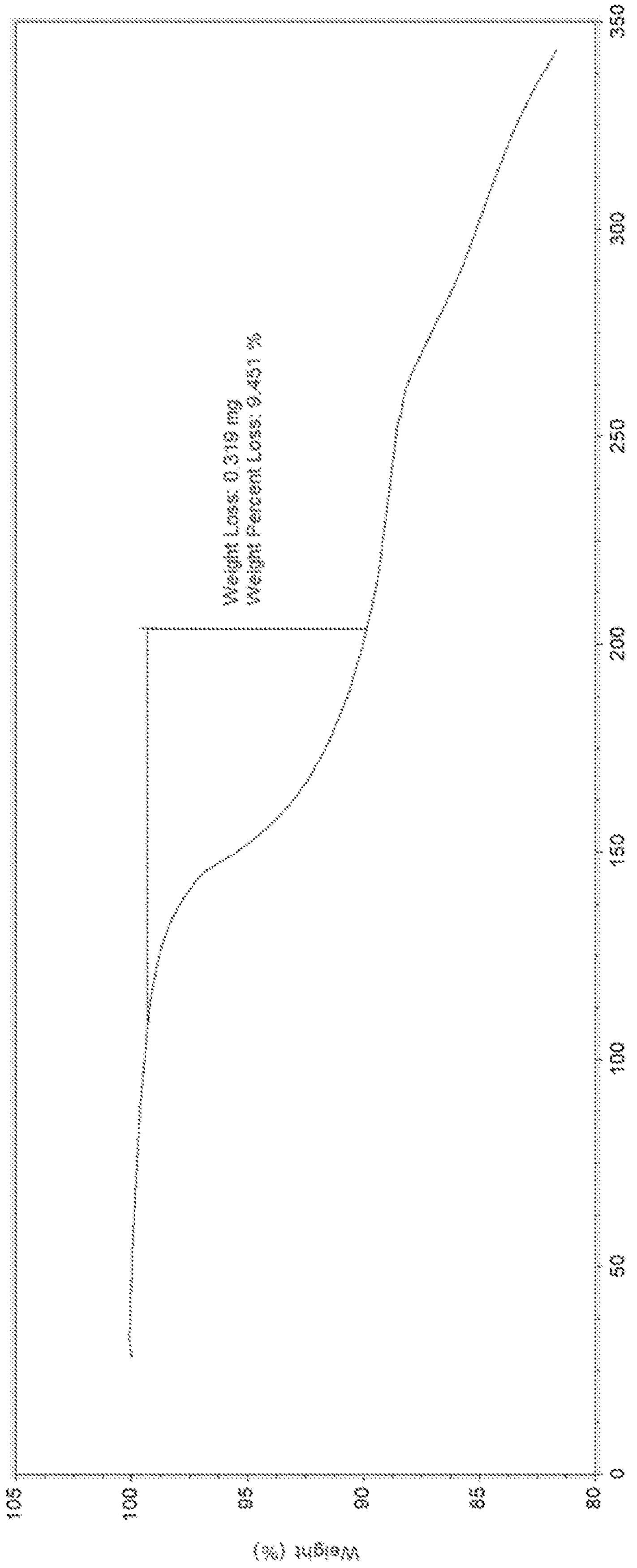
FIG. 6C shows a TG thermogram of the phentolamine mesylate dioxane solvate obtained as described in Example 5.

In some embodiments, the phentolamine mesylate exhibits a TG curve that is substantially the same as that depicted in FIG. 6C.

Figure 6D:
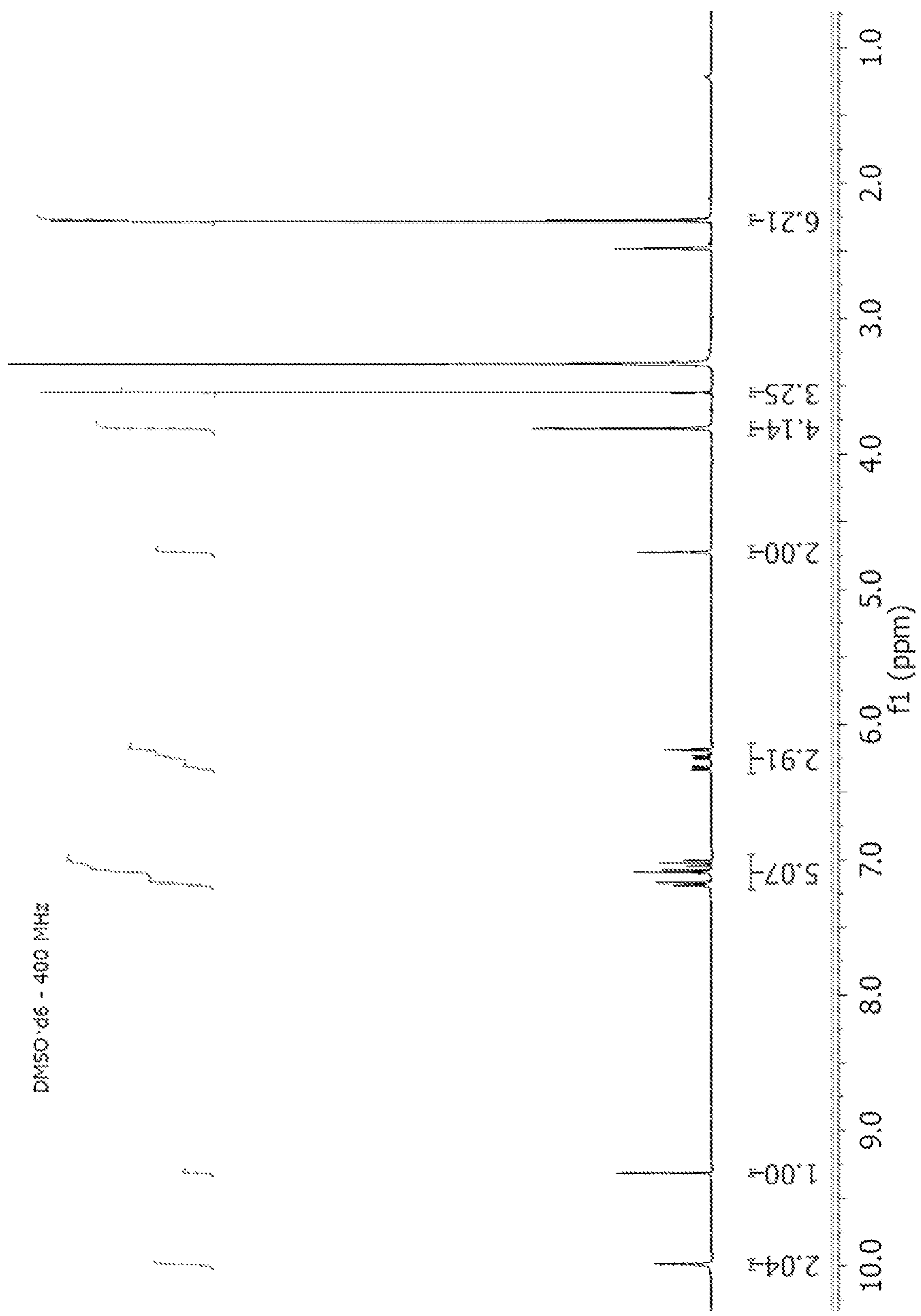
FIG. 6D shows a 1H NMR spectrum of the phentolamine mesylate dioxane solvate obtained as described in Example 5.

In some embodiments, the phentolamine mesylate exhibits a $^{1}$H-NMR spectrum that is substantially the same as that depicted in FIG. 6D.

In some embodiments, the compound of the invention is phentolamine mesylate obtained according to Example 5.

Figure 7:
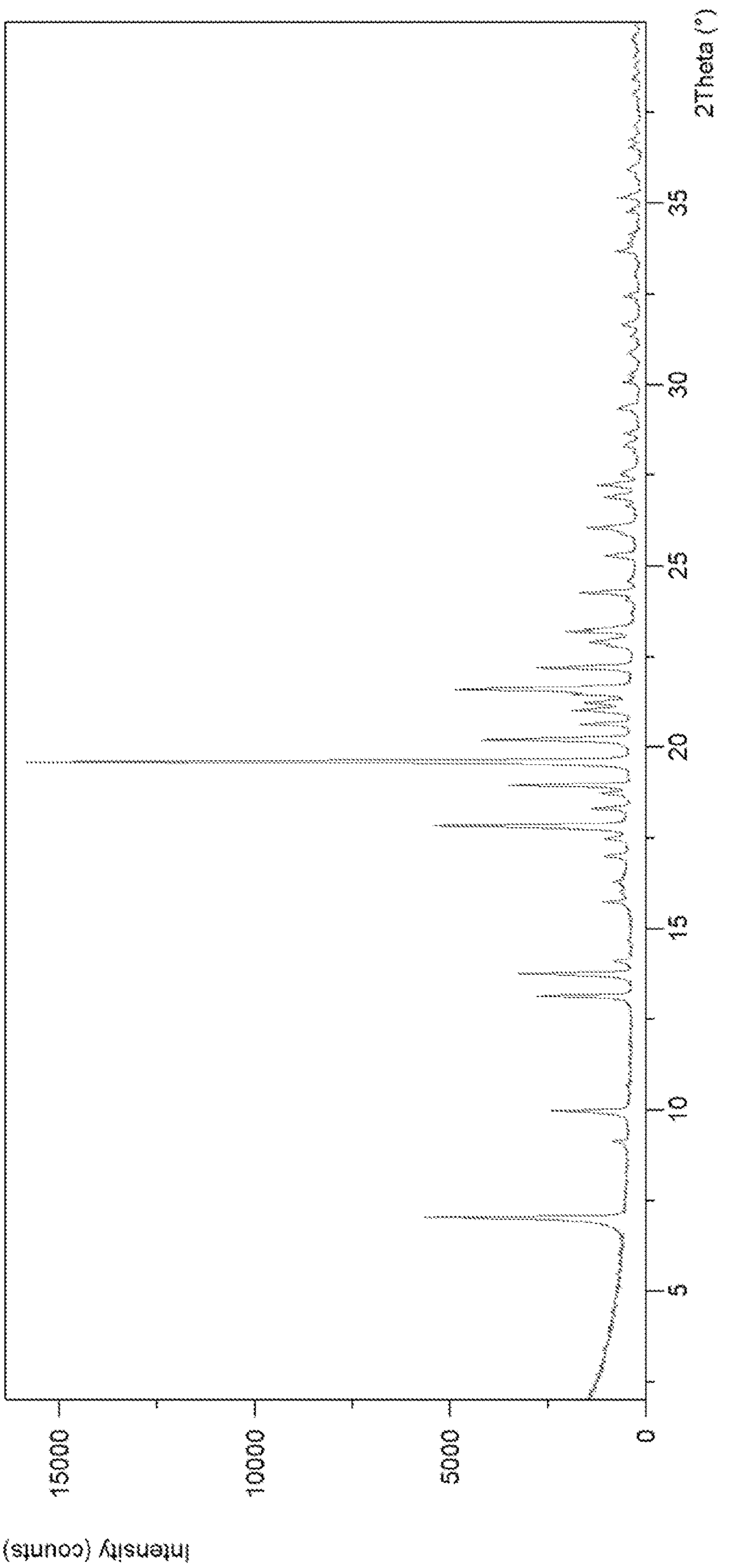
FIG. 7 shows an XRPD pattern of the phentolamine mesylate obtained as described in Example 6.

In some embodiments, the compound of the invention is phentolamine mesylate that exhibits an XRPD pattern that is substantially the same as that depicted in FIG. 7.

In some embodiments, the compound of the invention is phentolamine mesylate obtained according to Example 6.

Figure 8:
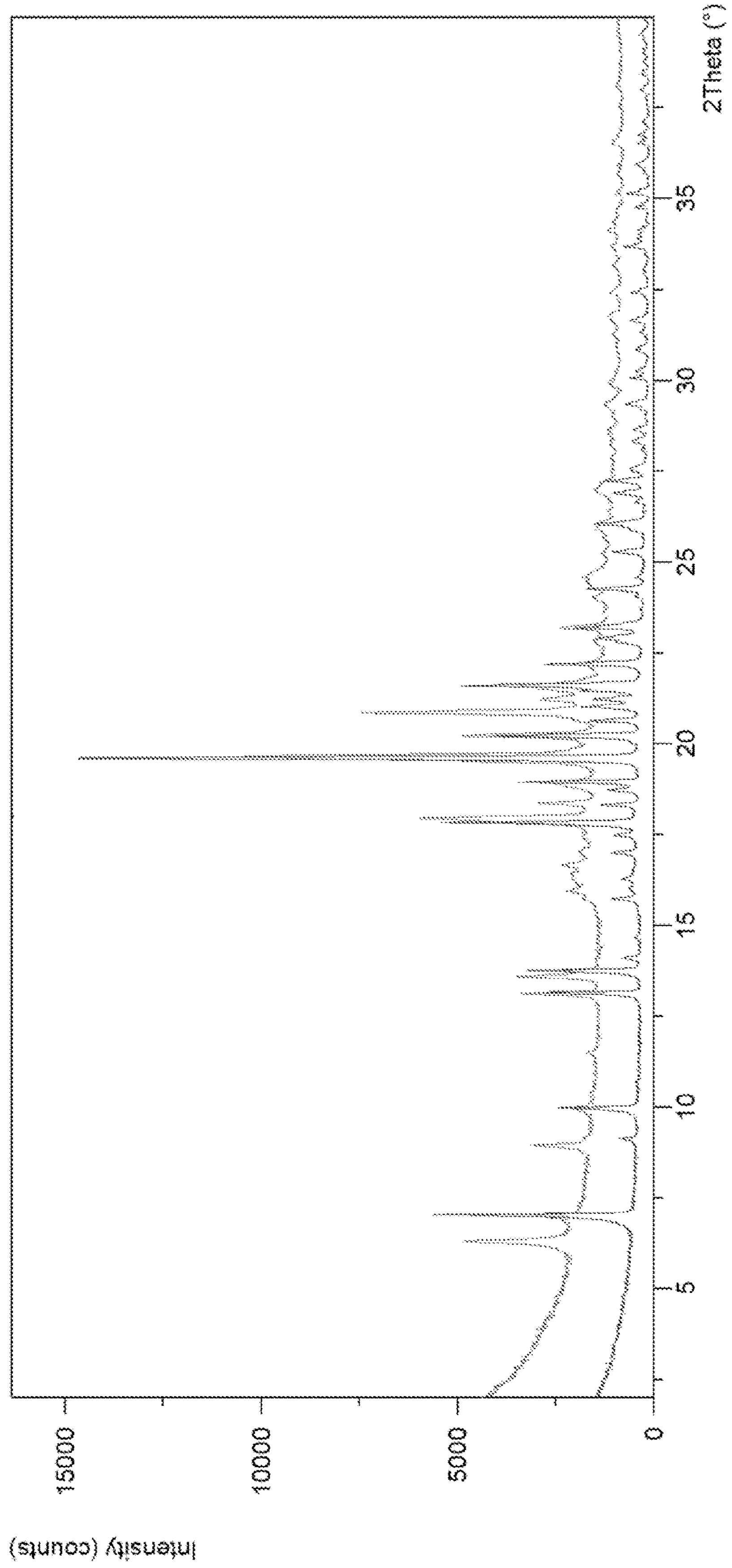
FIG. 8 shows an overlay of an XRPD pattern of the phentolamine mesylate obtained as described in Example 7 (top) and the XRPD pattern of the phentolamine mesylate of FIG. 7 (bottom).

In some embodiments, the compound of the invention is phentolamine mesylate that exhibits an XRPD pattern that is substantially the same as that depicted in FIG. 8.

In some embodiments, the compound of the invention is phentolamine mesylate obtained according to Example 7. In some embodiments, the phentolamine mesylate obtained according to Example 7 comprises the phentolamine mesylate obtained according to Example 6.

Figure 9:
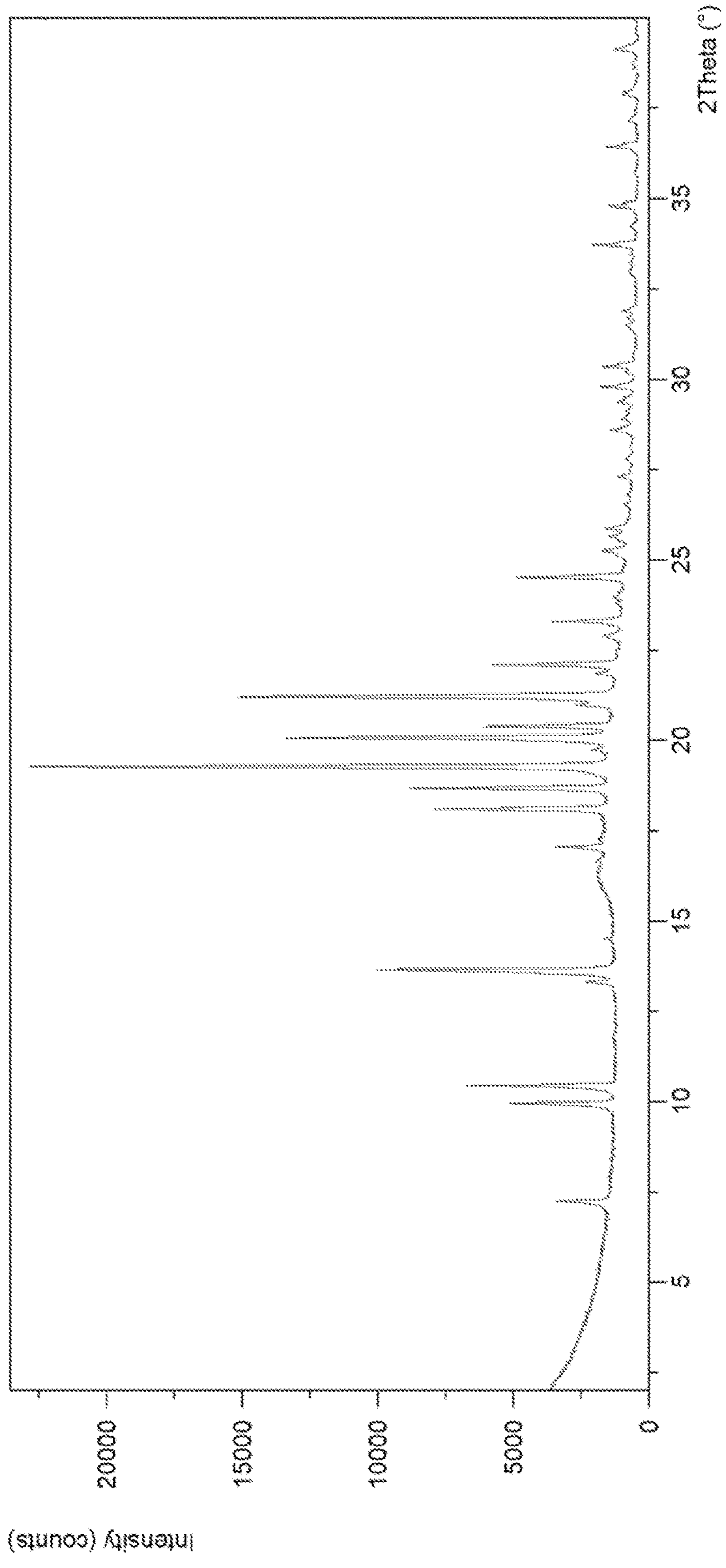
FIG. 9 shows an XRPD pattern of the phentolamine mesylate obtained as described in Example 8.

In some embodiments, the compound of the invention is phentolamine mesylate that exhibits an XRPD pattern that is substantially the same as that depicted in FIG. 9.

In some embodiments, the compound of the invention is phentolamine mesylate obtained according to Example 8.

Figure 10:
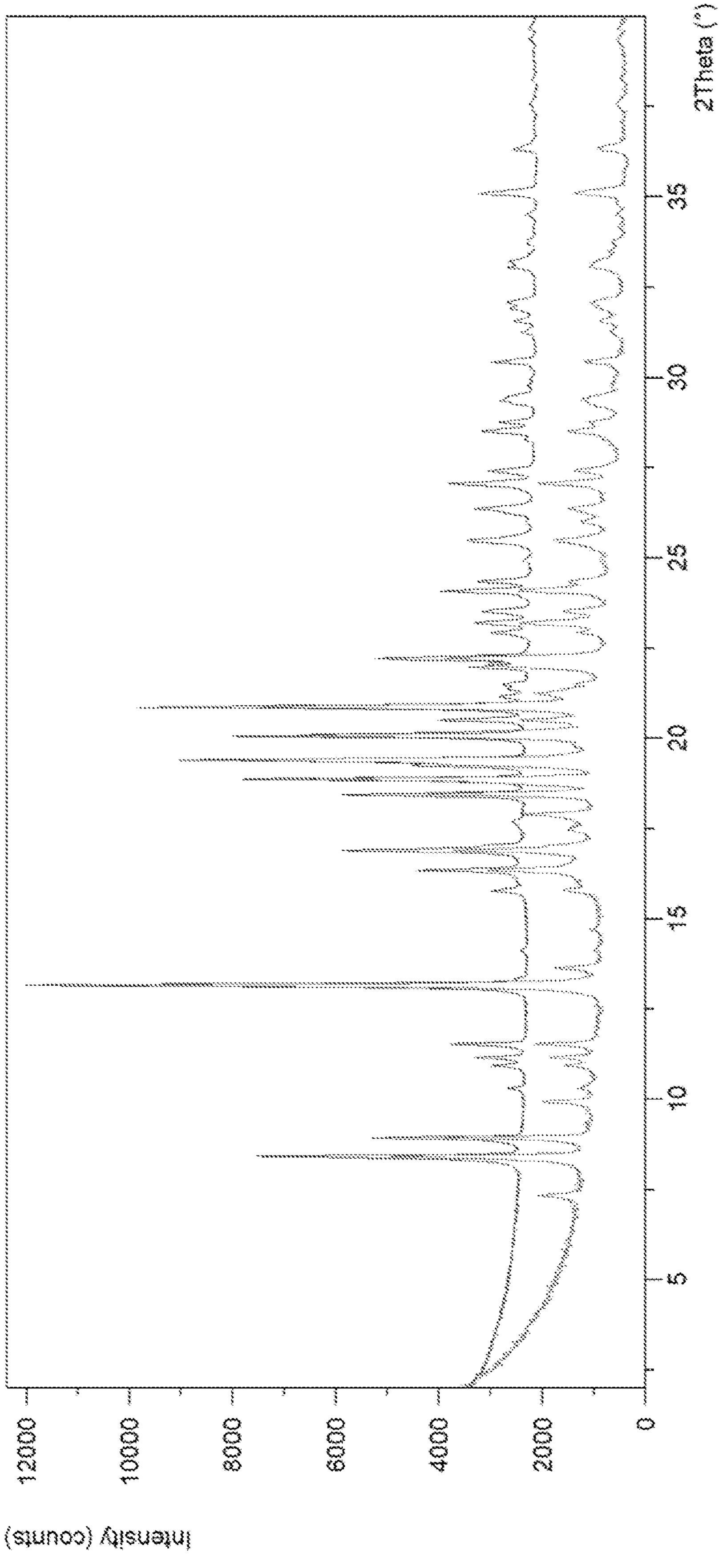
FIG. 10 shows an overlay of an XRPD pattern of the phentolamine mesylate obtained as described in Example 9 (bottom) and the XRPD pattern of the phentolamine mesylate of FIG. 2A (top).

In some embodiments, the compound of the invention is phentolamine mesylate that exhibits an XRPD pattern that is substantially the same as that depicted in FIG. 10.

In some embodiments, the compound of the invention is phentolamine mesylate obtained according to Example 9. In some embodiments, the phentolamine mesylate obtained according to Example 9 comprises the phentolamine mesylate obtained according to Example 1.

Figure 11:
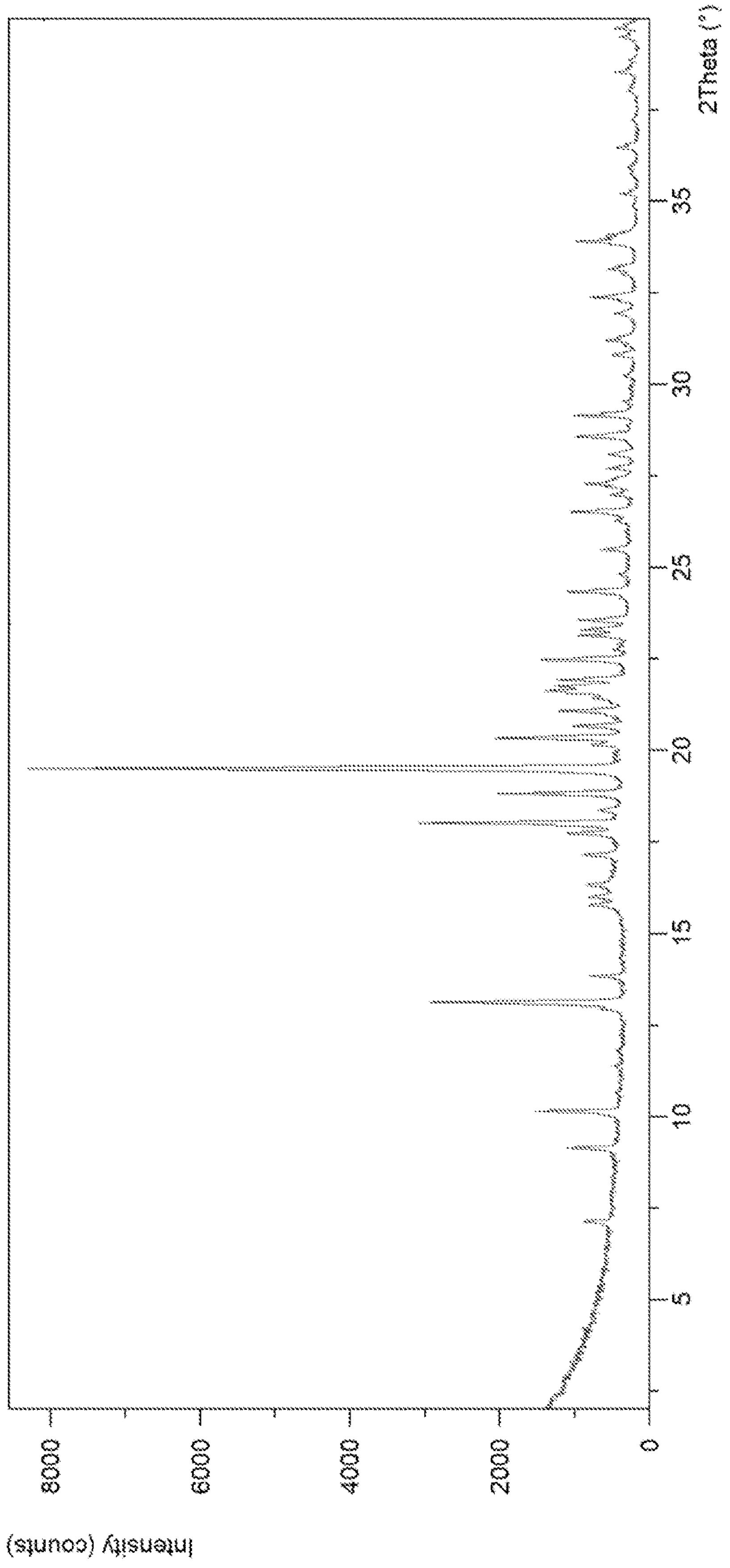
FIG. 11 shows an XRPD pattern of the phentolamine mesylate obtained as described in Example 10.

In some embodiments, the compound of the invention is phentolamine mesylate that exhibits an XRPD pattern that is substantially the same as that depicted in FIG. 11.

In some embodiments, the compound of the invention is phentolamine mesylate obtained according to Example 10.

Figure 12:
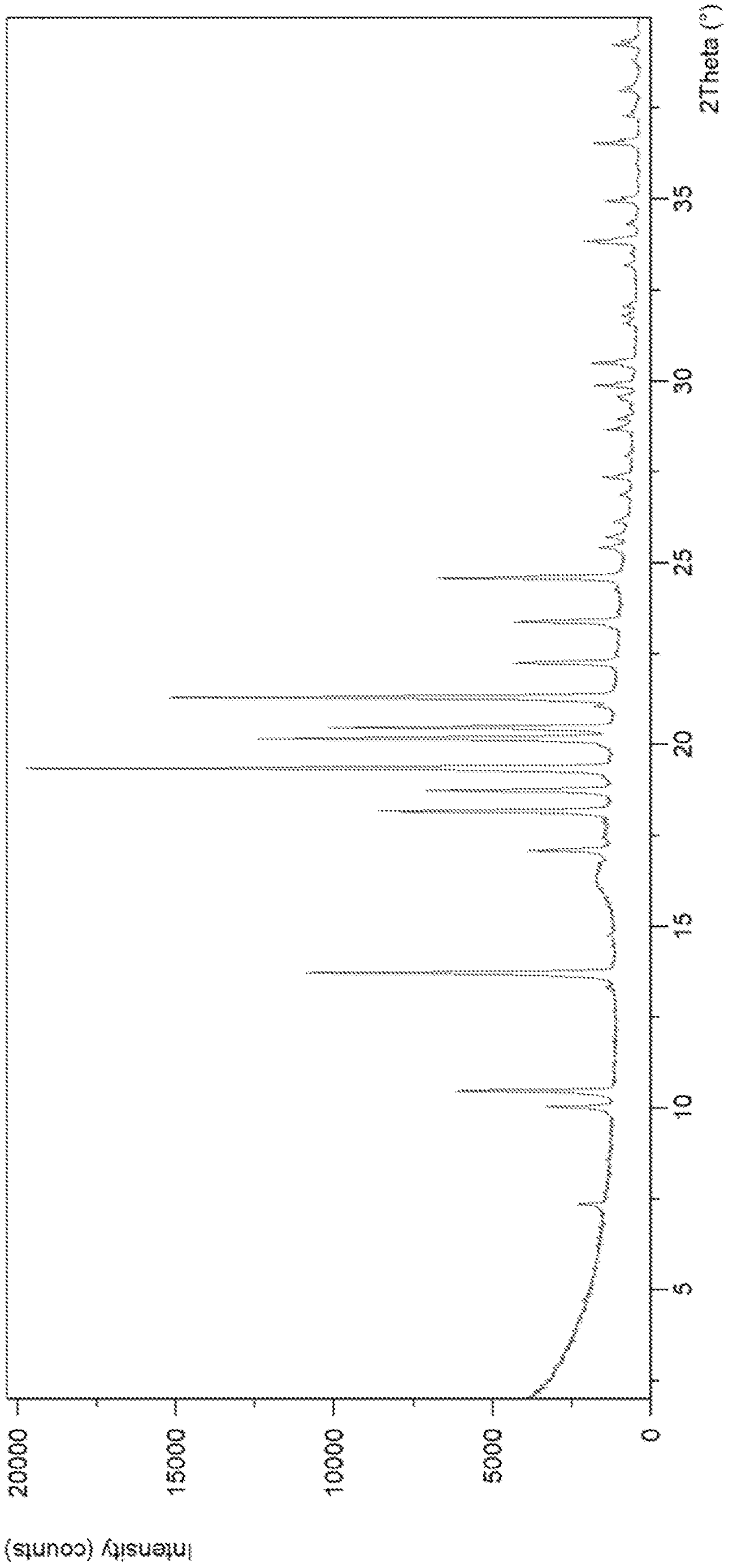
FIG. 12 shows an XRPD pattern of the phentolamine mesylate obtained as described in Example 11.

In some embodiments, the compound of the invention is phentolamine mesylate that exhibits an XRPD pattern that is substantially the same as that depicted in FIG. 12.

In some embodiments, the compound of the invention is phentolamine mesylate obtained according to Example 11.

Figure 13:
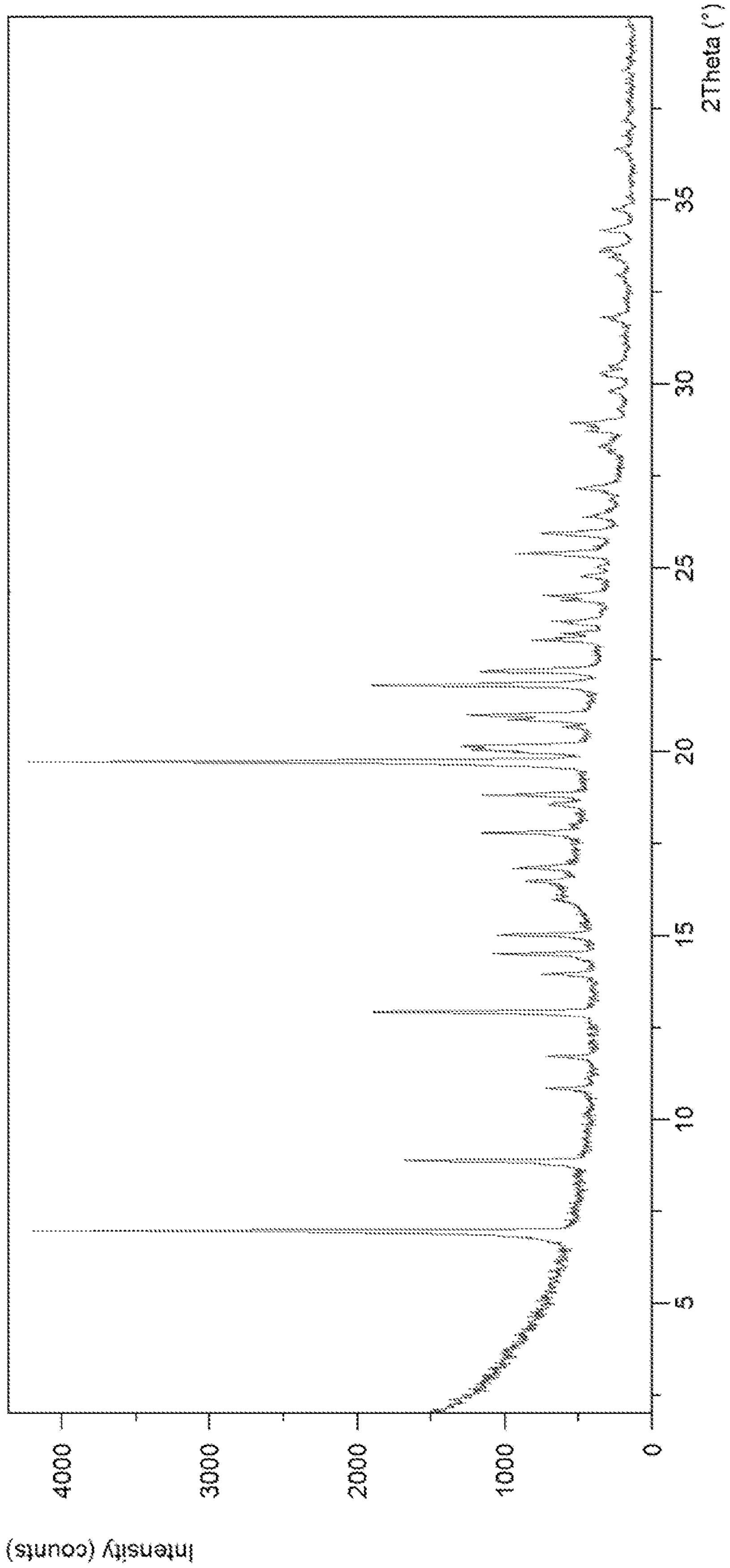
FIG. 13 shows an XRPD pattern of the phentolamine mesylate obtained as described in Example 12.

In some embodiments, the compound of the invention is phentolamine mesylate that exhibits an XRPD pattern that is substantially the same as that depicted in FIG. 13.

In some embodiments, the compound of the invention is phentolamine mesylate obtained according to Example 12.

In some embodiments, the phentolamine mesylate is at least about 98% pure by weight, and the phentolamine mesylate comprises no more than about 2% of an impurity by weight of the phentolamine mesylate. In some embodiments, the phentolamine mesylate is about 95.0% to 100% pure by weight, and the phentolamine mesylate comprises 0% to about 5% of an impurity by weight of the phentolamine mesylate. In some embodiments, the phentolamine mesylate is about 98% to 100% pure by weight, and the phentolamine mesylate comprises 0% to about 2% of an impurity by weight of the phentolamine mesylate. In some embodiments, the phentolamine mesylate is about 98%, about 98.5%, about 99%, about 99.5%, or 100% pure by weight, and the phentolamine mesylate comprises about 2%, about 1.5%, about 1%, about 0.5%, or 0%, respectively, of an impurity by weight of the phentolamine mesylate. In some embodiments, the phentolamine mesylate is about 99.5%, about 99.9%, or about 99.95% pure by weight, and the phentolamine mesylate comprises about 0.5%, about 0.1%, or about 0.05%, respectively, of an impurity by weight of the phentolamine mesylate. In some embodiments, the purity or the impurity are determined by high-performance liquid chromatography (HPLC). In some embodiments, the purity or impurity is determined by titration.

Figure 1B:
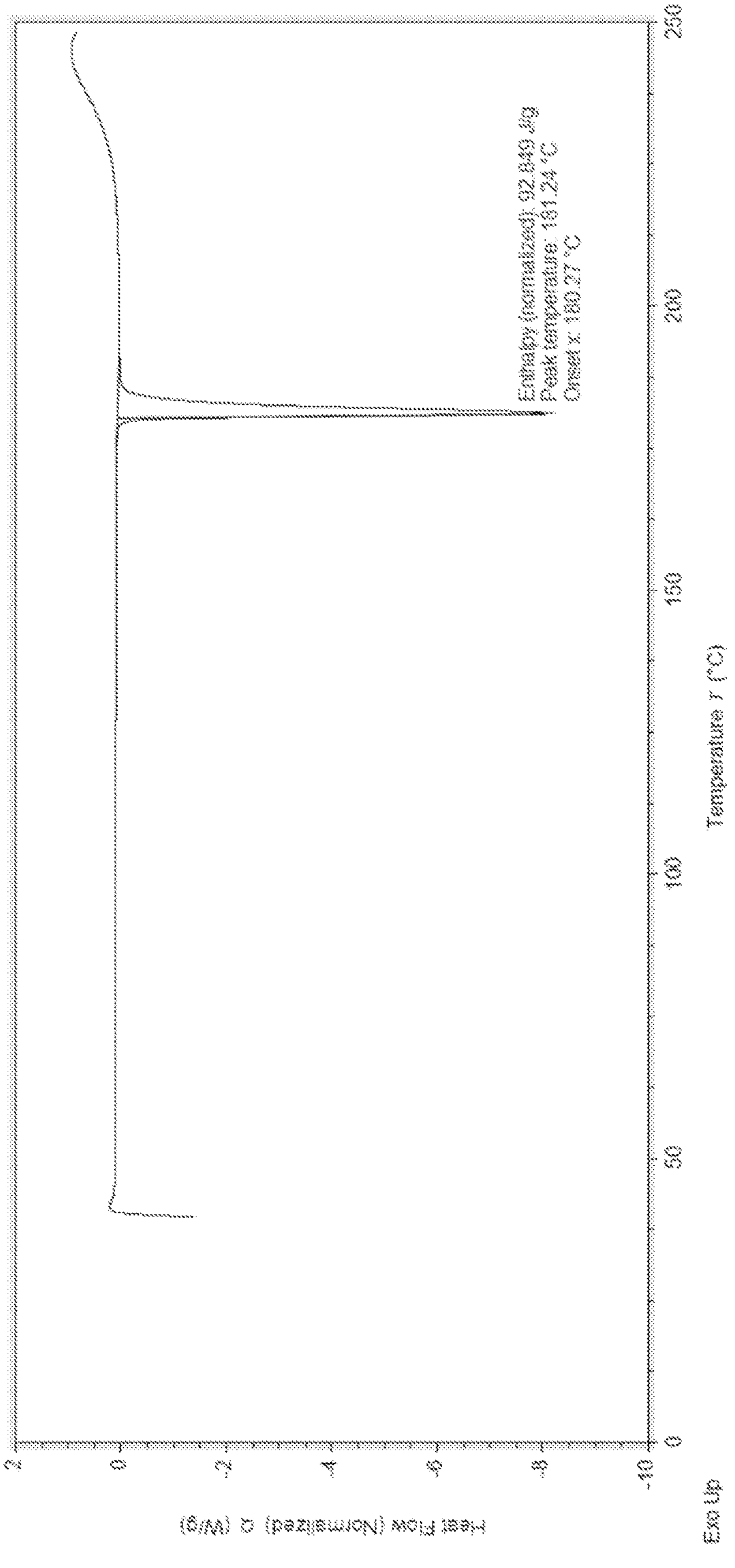
FIG. 1B shows a differential scanning calorimetry (DSC) thermogram of the Reference A.
Figure 1C:
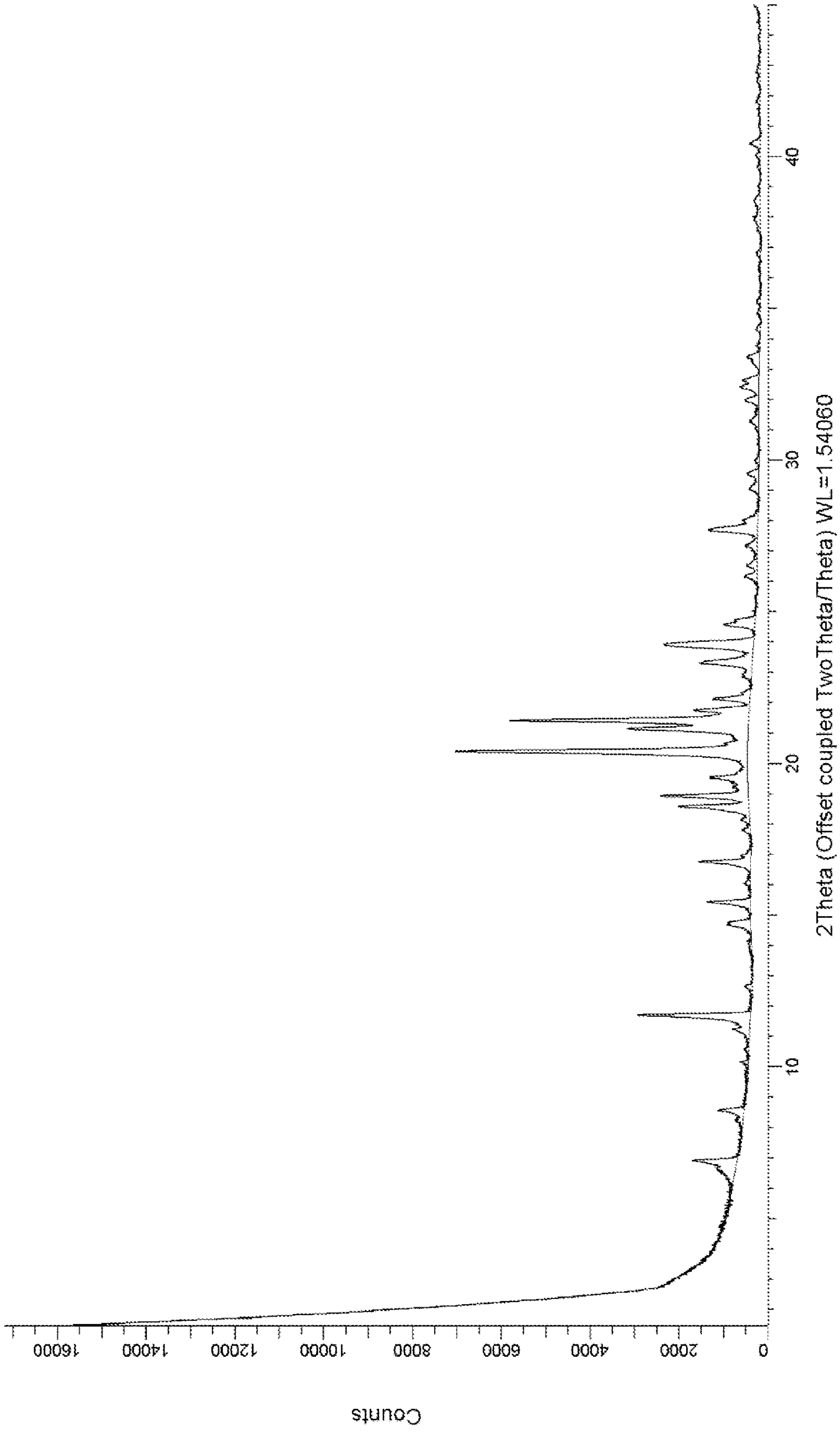
FIG. 1C depicts an XRPD pattern of phentolamine mesylate purchased from Chemo Iberica S.A. (Code 690001) ("Reference B").

In some embodiments, the phentolamine mesylate comprises less than 5% of phentolamine mesylate that exhibits an XRPD pattern that is substantially the same as that depicted in FIG. 1A or FIG. 1C. In some embodiments, the phentolamine mesylate comprises less than 3% of phentolamine mesylate that exhibits an XRPD pattern that is substantially the same as that depicted in FIG. 1A or FIG. 1C. In some embodiments, the phentolamine mesylate comprises less than 1% of phentolamine mesylate that exhibits an XRPD pattern that is substantially the same as that depicted in FIG. 1A or FIG. 1C.

In some embodiments, the phentolamine mesylate comprises less than 5% of phentolamine mesylate that exhibits an XRPD pattern that is substantially the same as that depicted in FIG. 1A. In some embodiments, the phentolamine mesylate comprises less than 3% of phentolamine mesylate that exhibits an XRPD pattern that is substantially the same as that depicted in FIG. 1A. In some embodiments, the phentolamine mesylate comprises less than 1% of phentolamine mesylate that exhibits an XRPD pattern that is substantially the same as that depicted in FIG. 1A.

In some embodiments, the phentolamine mesylate comprises less than 5% of phentolamine mesylate that exhibits an XRPD pattern that is substantially the same as that depicted in FIG. 1C. In some embodiments, the phentolamine mesylate comprises less than 3% of phentolamine mesylate that exhibits an XRPD pattern that is substantially the same as that depicted in FIG. 1C. In some embodiments, the phentolamine mesylate comprises less than 1% of phentolamine mesylate that exhibits an XRPD pattern that is substantially the same as that depicted in FIG. 1C.

In some embodiments, the phentolamine mesylate comprises less than 5% of phentolamine mesylate that exhibits an XRPD pattern substantially the same as that of Reference A. In some embodiments, the phentolamine mesylate comprises less than 3% of phentolamine mesylate that exhibits an XRPD pattern substantially the same as that of Reference A. In some embodiments, the phentolamine mesylate comprises less than 1% of phentolamine mesylate that exhibits an XRPD pattern substantially the same as that of Reference A.

In some embodiments, the phentolamine mesylate comprises less than 5% of phentolamine mesylate that exhibits an XRPD pattern substantially the same as that of Reference B. In some embodiments, the phentolamine mesylate comprises less than 3% of phentolamine mesylate that exhibits an XRPD pattern substantially the same as that of Reference B. In some embodiments, the phentolamine mesylate comprises less than 1% of phentolamine mesylate that exhibits an XRPD pattern substantially the same as that of Reference B.

In some embodiments, the compound of invention is dried.

In some embodiments, the compound of invention is purified.

In some embodiments, the compound of invention is isolated.

In some embodiments, the compound of invention is isolated and purified.

The compounds of the invention are useful in the ocular methods of the invention.

Synthesis Methods of the Invention

The present invention provides methods of making phentolamine mesylate that exhibits a particular XRPD pattern or exhibits one or more particular XRPD peaks.

The present invention further provides isolating the phentolamine mesylate prepared according to any one of the synthesis methods of the invention.

The present invention provides a method of making phentolamine mesylate according to Example 1. In some embodiments, phentolamine mesylate that exhibits an XRPD pattern comprising a peak at 8.4±0.2 degrees 2-theta and a peak at 16.3±0.2 degrees 2-theta is made according to Example 1. In some embodiments, the method further comprises isolating the phentolamine mesylate that exhibits an XRPD pattern comprising a peak at 8.4±0.2 degrees 2-theta and a peak at 16.3±0.2 degrees 2-theta.

In some embodiments, a method for making phentolamine mesylate that exhibits an XRPD pattern comprising a peak at 8.4±0.2 degrees 2-theta and a peak at 16.3±0.2 degrees 2-theta comprises: (a) heating a mixture comprising phentolamine mesylate comprising an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta; methane sulfonic acid; acetone;

and water at about 45° C. for about thirty minutes to provide a heated mixture; (b) allowing the heated mixture to cool to room temperature to provide a cooled mixture; (c) diluting the cooled mixture with t-butyl methyl ether to provide a t-butyl methyl ether mixture; and (d) cooling the t-butyl methyl ether mixture to about −20° C. to precipitate the phentolamine mesylate that exhibits an XRPD pattern comprising a peak at 8.4±0.2 degrees 2-theta and a peak at 16.3±0.2 degrees 2-theta. In some embodiments, the method further comprises (e) isolating the phentolamine mesylate that exhibits an XRPD pattern comprising a peak at 8.4±0.2 degrees 2-theta and a peak at 16.3±0.2 degrees 2-theta.

In some embodiments, a method for making phentolamine mesylate that exhibits an XRPD pattern comprising a peak at 8.4±0.2 degrees 2-theta and a peak at 16.3±0.2 degrees 2-theta comprises: (a) heating a mixture comprising phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta and dichloromethane at about 50° C. for about two hours to provide a heated mixture; (b) allowing the heated mixture to cool at about 25° C. for about two hours to provide cooled phentolamine mesylate; and (c) repeating steps (a) and (b) for up to about three days to provide the phentolamine mesylate that exhibits an XRPD pattern comprising a peak at 8.4±0.2 degrees 2-theta and a peak at 16.3±0.2 degrees 2-theta. In some embodiments, the method further comprises (d) isolating the phentolamine mesylate that exhibits an XRPD pattern comprising a peak at 8.4±0.2 degrees 2-theta and a peak at 16.3±0.2 degrees 2-theta. In some embodiments, the heating in step (a) is at 1° C./min. In some embodiments, the cooling in step (b) is at 1° C./min.

In some embodiments, a method for making phentolamine mesylate that exhibits an XRPD pattern comprising a peak at 8.4±0.2 degrees 2-theta and a peak at 16.3±0.2 degrees 2-theta comprises: (a) dissolving phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta in a mixture comprising methyl ethyl ketone and water at about 80° C. to provide a solution; (b) cooling the solution to about 45° C. and adding seeds of phentolamine mesylate that exhibits an XRPD pattern comprising a peak at 8.4±0.2 degrees 2-theta and a peak at 16.3±0.2 degrees 2-theta to provide a seeded mixture; (c) cooling the seeded mixture at 10° C. for about thirty minutes to provide a cooled mixture; (d) heating the cooled mixture at 35° C. under vacuum to reduce the volume of the mixture by about 33% and provide a reduced mixture; and (e) cooling the reduced mixture at 10° C. for about forty minutes to provide the phentolamine mesylate that exhibits an XRPD pattern comprising a peak at 8.4±0.2 degrees 2-theta and a peak at 16.3±0.2 degrees 2-theta. In some embodiments, the method further comprises (f) isolating the phentolamine mesylate that exhibits an XRPD pattern comprising a peak at 8.4±0.2 degrees 2-theta and a peak at 16.3±0.2 degrees 2-theta. In some embodiments, the mixture of methyl ethyl ketone and water in step (a) is 96:4 w/w. In some embodiments, the cooling in step (b) is at 0.5° C./min.

In some embodiments, a method for making phentolamine mesylate that exhibits an XRPD pattern comprising a peak at 8.4±0.2 degrees 2-theta and a peak at 16.3±0.2 degrees 2-theta comprises: (a) heating a mixture comprising phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta, methyl ethyl ketone, and water to about 77° C. to provide a heated mixture; (b) cooling the heated mixture to 10° C. to provide a cooled mixture; and (c) repeating steps (a) and (b) twice to provide the phentolamine mesylate that exhibits an XRPD pattern comprising a peak at 8.4±0.2 degrees 2-theta and a peak at 16.3±0.2 degrees 2-theta. In some embodiments, the method further comprises (d) isolating the phentolamine mesylate that exhibits an XRPD pattern comprising a peak at 8.4±0.2 degrees 2-theta and a peak at 16.3±0.2 degrees 2-theta. In some embodiments, the ratio of methyl ethyl ketone and water in step (a) is 96:4 w/w. In some embodiments, the heating in step (a) is at 0.5° C./min. In some embodiments, the cooling in step (b) is at 0.5° C./min.

The present invention provides a method of making phentolamine mesylate according to this Example 2. In some embodiments, phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is made according to this Example 2. In some embodiments, the method further comprises isolating the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta.

In some embodiments, a method for making phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta comprises: (a) heating phentolamine mesylate that exhibits an XRPD pattern comprising a peak at 8.4±0.2 degrees 2-theta and a peak at 16.3±0.2 degrees 2-theta to about 126° C. to provide heated phentolamine mesylate; and (b) allowing the heated phentolamine mesylate to cool to room temperature to provide the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the method further comprises (c) isolating the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the heating in step (a) is at a rate of about 10° C./min.

The present invention provides a method of making phentolamine mesylate according to Example 3. In some embodiments, phentolamine mesylate that exhibits an XRPD pattern that is substantially the same as that depicted in FIG. 4A is made according to Example 3. In some embodiments, the method further comprises isolating the phentolamine mesylate that exhibits an XRPD pattern that is substantially the same as that depicted in FIG. 4A.

In some embodiments, a method for making phentolamine mesylate that exhibits an XRPD pattern that is substantially the same as that depicted in FIG. 4A, comprises: (a) heating a mixture comprising phentolamine mesylate that exhibits an XRPD pattern that is substantially the same as that depicted in FIG. 1A or FIG. 1C, and acetone at about 50° C. for about two hours to provide a heated mixture; (b) allowing the heated mixture to cool at about 25° C. for about two hours to provide cooled phentolamine mesylate; and (c) repeating steps (a) and (b) for up to about three days to provide the phentolamine mesylate that exhibits an XRPD pattern that is substantially the same as that depicted in FIG. 4A. In some embodiments, the method further comprises (c) isolating the phentolamine mesylate that exhibits an XRPD pattern that is substantially the same as that depicted in FIG. 4A. In some embodiments, the heating in step (a) is at a rate of about 1° C./min. In some embodiments, the cooling in step (b) is at a rate of about 1° C./min. In some embodiments, the phentolamine mesylate in step (a) exhibits an XRPD pattern that is substantially the same as that depicted in FIG. 1A. In some embodiments, the phentolamine mesylate in step (a) exhibits an XRPD pattern that is substantially the same as that depicted in FIG. 1C.

The present invention provides a method of making phentolamine mesylate according to Example 4. In some embodiments, phentolamine mesylate that exhibits an XRPD pattern that is substantially the same as that depicted in FIG. 5A is made according to Example 4. In some embodiments, the method further comprises isolating the phentolamine mesylate that exhibits an XRPD pattern that is substantially the same as that depicted in FIG. 5A.

The present invention provides a method of making phentolamine mesylate according to Example 5. In some embodiments, phentolamine mesylate that exhibits an XRPD pattern that is substantially the same as that depicted in FIG. 6A is made according to Example 5. In some embodiments, the method further comprises isolating the phentolamine mesylate that exhibits an XRPD pattern that is substantially the same as that depicted in FIG. 6A.

In some embodiments, a method for making phentolamine mesylate that exhibits an XRPD pattern that is substantially the same as that depicted in FIG. 6A comprises: (a) pulverizing phentolamine mesylate that exhibits an XRPD pattern that is substantially the same as that depicted in FIG. 1A or FIG. 1C in the presence of an excess of 1,4-dioxane solvent to provide a pulverized mixture; and (b) removing the 1,4-dioxane solvent from the pulverized mixture to provide the phentolamine mesylate that exhibits an XRPD pattern that is substantially the same as that depicted in FIG. 6A. In some embodiments, the method further comprises (c) isolating the phentolamine mesylate that exhibits an XRPD pattern that is substantially the same as that depicted in FIG. 6A. In some embodiments, the pulverizing in step (a) is with stainless steel balls. In some embodiments, the pulverizing in step (a) is at about 400 rpm. In some embodiments, the phentolamine mesylate in step (a) exhibits an XRPD pattern that is substantially the same as that depicted in FIG. 1A. In some embodiments, the phentolamine mesylate in step (a) exhibits an XRPD pattern that is substantially the same as that depicted in FIG. 1C.

The present invention provides a method of making phentolamine mesylate according to Example 6. In some embodiments, phentolamine mesylate that exhibits an XRPD pattern that is substantially the same as that depicted in FIG. 7 is made according to Example 6. In some embodiments, the method further comprises isolating the phentolamine mesylate that exhibits an XRPD pattern that is substantially the same as that depicted in FIG. 7.

The present invention provides a method of making phentolamine mesylate according to Example 7. In some embodiments, phentolamine mesylate that exhibits an XRPD pattern that is substantially the same as that depicted in FIG. 8 is made according to Example 7. In some embodiments, the method further comprises isolating the phentolamine mesylate that exhibits an XRPD pattern that is substantially the same as that depicted in FIG. 8.

The present invention provides a method of making phentolamine mesylate according to Example 8. In some embodiments, phentolamine mesylate that exhibits an XRPD pattern that is substantially the same as that depicted in FIG. 9 is made according to Example 8. In some embodiments, the method further comprises isolating the phentolamine mesylate that exhibits an XRPD pattern that is substantially the same as that depicted in FIG. 9.

The present invention provides a method of making phentolamine mesylate according to Example 9. In some embodiments, phentolamine mesylate that exhibits an XRPD pattern that is substantially the same as that depicted in FIG. 10 is made according to Example 9. In some embodiments, the method further comprises isolating the phentolamine mesylate that exhibits an XRPD pattern that is substantially the same as that depicted in FIG. 10.

The present invention provides a method of making phentolamine mesylate according to Example 10. In some embodiments, phentolamine mesylate that exhibits an XRPD pattern that is substantially the same as that depicted in FIG. 11 is made according to Example 10. In some embodiments, the method further comprises isolating the phentolamine mesylate that exhibits an XRPD pattern that is substantially the same as that depicted in FIG. 11.

The present invention provides a method of making phentolamine mesylate according to Example 11. In some embodiments, phentolamine mesylate that exhibits an XRPD pattern that is substantially the same as that depicted in FIG. 12 is made according to Example 11. In some embodiments, the method further comprises isolating the phentolamine mesylate that exhibits an XRPD pattern that is substantially the same as that depicted in FIG. 12.

The present invention provides a method of making phentolamine mesylate according to Example 12. In some embodiments, phentolamine mesylate that exhibits an XRPD pattern that is substantially the same as that depicted in FIG. 13 is made according to Example 12. In some embodiments, the method further comprises isolating the phentolamine mesylate that exhibits an XRPD pattern that is substantially the same as that depicted in FIG. 13.

Other Compounds Useful in the Ocular Methods of the Invention

In some embodiments, a compound useful in the ocular methods of the invention is Reference A. In some embodiments, a compound useful in the ocular methods of the invention exhibits an XRPD pattern substantially the same as that of Reference A.

In some embodiments, a compound useful in the ocular methods of the invention is Reference B. In some embodiments, a compound useful in the ocular methods of the invention exhibits an XRPD pattern substantially the same as that of Reference B.

In some embodiments, a compound useful in the ocular methods of the invention is phentolamine mesylate that exhibits an XRPD pattern that is substantially the same as that depicted in FIG. 1A or FIG. 1C. In some embodiments, a compound useful in the ocular methods of the invention is phentolamine mesylate that exhibits an XRPD pattern that is substantially the same as that depicted in FIG. 1A. In some embodiments, a compound useful in the ocular methods of the invention is phentolamine mesylate that exhibits an XRPD pattern that is substantially the same as that depicted in FIG. 1C.

In some embodiments, a compound useful in the ocular methods of the invention is phentolamine mesylate that exhibits an XRPD pattern comprising a peak at 20.3±0.2 degrees 2-theta and a peak at 21.1±0.2 degrees 2-theta, wherein the peak at 20.3±0.2 degrees 2-theta has a relative intensity of greater than 80%. In some embodiments, the XRPD pattern further comprises a peak at 6.9±0.2 degrees 2-theta, a peak at 11.6±0.2 degrees 2-theta, or a peak at 15.6±0.2 degrees 2-theta.

In some embodiments, a compound useful in the ocular methods of the invention is phentolamine mesylate that exhibits an XRPD pattern comprising a peak at 6.9±0.2 degrees 2-theta, a peak at 11.6±0.2 degrees 2-theta, a peak at 15.4±0.2 degrees 2-theta, a peak at 20.3±0.2 degrees 2-theta, and a peak at 21.7±0.2 degrees 2-theta. %. In some embodiments, the XRPD pattern further comprises a peak at 8.5±0.2 degrees 2-theta, a peak at 10.1±0.2 degrees 2-theta, a peak at 18.5±0.2 degrees 2-theta, a peak at 21.3±0.2 degrees 2-theta, a peak at 23.8±0.2 degrees 2-theta, or a peak at 23.9±0.2 degrees 2-theta. In some embodiments, the XRPD pattern further comprises a peak at 8.5±0.2 degrees 2-theta, a peak at 10.1±0.2 degrees 2-theta, a peak at 18.5±0.2 degrees 2-theta, a peak at 21.3±0.2 degrees 2-theta, a peak at 23.8±0.2 degrees 2-theta, and a peak at 23.9±0.2 degrees 2-theta.

In some embodiments, a compound useful in the ocular methods of the invention is phentolamine mesylate that exhibits an XRPD pattern that is substantially the same as that depicted in FIG. 1A.

In some embodiments, a compound useful in the ocular methods of the invention is phentolamine mesylate that exhibits an XRPD pattern comprising the peaks of Table 1 having at least 30% relative intensity. In some embodiments, a compound useful in the ocular methods of the invention is phentolamine mesylate that exhibits an XRPD pattern comprising the peaks of Table 1 having at least 20% relative intensity. In some embodiments, a compound useful in the ocular methods of the invention is phentolamine mesylate that exhibits an XRPD pattern comprising the peaks of Table 1 having at least 15% relative intensity. In some embodiments, a compound useful in the ocular methods of the invention is phentolamine mesylate that exhibits an XRPD pattern comprising the peaks of Table 1 having at least 10% relative intensity.

In some embodiments, a compound useful in the ocular methods of the invention is phentolamine mesylate that exhibits an XRPD pattern that is substantially the same as that depicted in FIG. 1C.

In some embodiments, a compound useful in the ocular methods of the invention is phentolamine mesylate that exhibits an XRPD pattern comprising the peaks of Table 2 having at least 30% relative intensity. In some embodiments, a compound useful in the ocular methods of the invention is phentolamine mesylate that exhibits an XRPD pattern comprising the peaks of Table 2 having at least 20% relative intensity. In some embodiments, a compound useful in the ocular methods of the invention is phentolamine mesylate that exhibits an XRPD pattern comprising the peaks of Table 2 having at least 15% relative intensity. In some embodiments, a compound useful in the ocular methods of the invention is phentolamine mesylate that exhibits an XRPD pattern comprising the peaks of Table 2 having at least 10% relative intensity.

In some embodiments, a compound useful in the ocular methods of the invention is phentolamine mesylate that exhibits an XRPD pattern comprising a peak at 20.3±0.3 degrees 2-theta, wherein the peak at 20.3±0.3 degrees 2-theta has a relative peak intensity (%) of greater than 85%. In some embodiments, the phentolamine mesylate exhibits an XRPD pattern comprising a peak at 20.3±0.3 degrees 2-theta, wherein the peak at 20.3±0.3 degrees 2-theta has a relative peak intensity (%) of greater than 90%. In some embodiments, the phentolamine mesylate exhibits an XRPD pattern comprising a peak at 20.3±0.3 degrees 2-theta, wherein the peak at 20.3±0.3 degrees 2-theta is the XRPD pattern's most intense peak.

In some embodiments, a compound useful in the ocular methods of the invention is phentolamine mesylate that exhibits an XRPD pattern comprising a peak at 20.3±0.2 degrees 2-theta, wherein the peak at 20.3±0.2 degrees 2-theta has a relative peak intensity (%) of greater than 85%. In some embodiments, the phentolamine mesylate exhibits an XRPD pattern comprising a peak at 20.3±0.2 degrees 2-theta, wherein the peak at 20.3±0.2 degrees 2-theta has a relative peak intensity (%) of greater than 90%. In some embodiments, the phentolamine mesylate exhibits an XRPD pattern comprising a peak at 20.3±0.2 degrees 2-theta, wherein the peak at 20.3±0.2 degrees 2-theta is the XRPD pattern's most intense peak.

In some embodiments, a compound useful in the ocular methods of the invention is phentolamine mesylate that exhibits an XRPD pattern comprising a peak at 21.1±0.2 degrees 2-theta, wherein the peak at 21.1±0.2 degrees 2-theta has a relative peak intensity (%) of greater than 30%.

In some embodiments, a compound useful in the ocular methods of the invention is phentolamine mesylate that exhibits an XRPD pattern comprising a peak at 11.6±0.2 degrees 2-theta, wherein the peak at 11.6±0.2 degrees 2-theta has a relative peak intensity (%) of greater than 30%.

In some embodiments, a compound useful in the ocular methods of the invention is phentolamine mesylate that exhibits an XRPD pattern comprising a peak at 20.3±0.2 degrees 2-theta, a peak at 21.1±0.2 degrees 2-theta, and a peak at 21.1±0.2 degrees 2-theta, wherein the peak at 20.3±0.2 degrees 2-theta has a relative peak intensity (%) of greater than 80% and the peak at 21.1±0.2 degrees 2-theta and the peak at 21.1±0.2 degrees 2-theta each has a relative peak intensity (%) of greater than 30%.

Ocular Methods of the Invention

In some embodiments, the compound of the invention is useful for treating or reversing pharmacologically induced mydriasis. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

Accordingly, the invention further provides methods for treating or reversing pharmacologically induced mydriasis, comprising administering to a subject in need thereof an effective amount of a compound of the invention or a composition of the invention. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis produced by an adrenergic agonist, comprising administering to a subject in need thereof an effective amount of phentolamine mesylate that exhibits an XRPD pattern that is substantially the same as that depicted in FIG. 1A or FIG. 1C or a composition comprising (i) phentolamine mesylate that exhibits an XRPD pattern that is substantially the same as that depicted in FIG. 1A or FIG. 1C and (ii) a pharmaceutically acceptable carrier or vehicle. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the adrenergic agonist is phenylephrine. In some embodiments, the administering is topically instilling into one or both eyes of the subject.

The invention further provides methods for treating or reversing pharmacologically induced mydriasis produced by a parasympatholytic agent, comprising administering to a subject in need thereof an effective amount of phentolamine mesylate that exhibits an XRPD pattern that is substantially the same as that depicted in FIG. 1A or FIG. 1C or a composition comprising (i) phentolamine that exhibits an XRPD pattern that is substantially the same as that depicted in FIG. 1A or FIG. 1C and (ii) a pharmaceutically acceptable carrier or vehicle. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern comprising a peak at 8.4±0.2 degrees 2-theta and a peak at 16.3±0.2 degrees 2-theta. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern that is substantially the same as that depicted in FIG. 2A. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern that is substantially the same as that depicted in FIG. 3A. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern comprising a peak at 8.4±0.2 degrees 2-theta and a peak at 16.3±0.2 degrees 2-theta and (ii) a pharmaceutically acceptable carrier or vehicle. In some embodiments, the pharmacologically induced mydriasis is produced by an adrenergic agonist. In some embodiments, the adrenergic agonist is phenylephrine.

In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern that is substantially the same as that depicted in FIG. 2A and (ii) a pharmaceutically acceptable carrier or vehicle. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern comprising a Table 3 peak having a relative peak intensity (%) of greater than 30% and (ii) a pharmaceutically acceptable carrier or vehicle. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta and (ii) a pharmaceutically acceptable carrier or vehicle. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern that is substantially the same as that depicted in FIG. 3A and (ii) a pharmaceutically acceptable carrier or vehicle. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide.

The invention further provides methods for treating or reversing pharmacologically induced mydriasis, comprising administering to a subject in need thereof an effective amount of a composition comprising (i) phentolamine mesylate that exhibits an XRPD pattern comprising a Table 4 peak having a relative peak intensity (%) of greater than 30% and (ii) a pharmaceutically acceptable carrier or vehicle. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13. In some embodiments, the pharmacologically induced mydriasis produced by an adrenergic agonist. In some embodiments, the adrenergic agonist is phenylephrine. In some embodiments, the pharmacologically induced mydriasis produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of a composition comprising (i) phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (ii) a pharmaceutically acceptable carrier or vehicle. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which a compound of the invention is dissolved. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern comprising a peak at 8.4±0.2 degrees 2-theta and a peak at 16.3±0.2 degrees 2-theta is dissolved. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern that is substantially the same as that depicted in FIG. 2A is dissolved. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern comprising a Table 3 peak having a relative peak intensity (%) of greater than 30% is dissolved. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern that is substantially the same as that depicted in FIG. 3A is dissolved. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern comprising a Table 4 peak having a relative peak intensity (%) of greater than 30% is dissolved. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis, comprising administering to a subject in need thereof an effective amount of an ophthalmic solution in which phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved. In some embodiments, the pharmacologically induced mydriasis produced by an adrenergic agonist. In some embodiments, the adrenergic agonist is phenylephrine. In some embodiments, the pharmacologically induced mydriasis produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle a compound of the invention to provide an ophthalmic solution in which the compound of the invention is dissolved and (b) administering to the subject the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing in a subject in need thereof pharmacologically induced mydriasis produced by an adrenergic agonist, comprising (a) dissolving in a pharmaceutically acceptable aqueous carrier or vehicle phentolamine mesylate that exhibits an XRPD pattern that is substantially the same as that depicted in FIG. 1A or FIG. 1C to provide an ophthalmic solution in which the phentolamine mesylate that exhibits an XRPD pattern that is substantially the same as that depicted in FIG. 1A or FIG. 1C is dissolved and (b) administering to the subject an effective amount of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the adrenergic agonist is phenylephrine. In some embodiments, the administering is topically instilling into one or both eyes of the subject.

The invention further provides methods for treating or reversing in a subject in need thereof pharmacologically induced mydriasis produced by a parasympatholytic agent, comprising (a) dissolving in a pharmaceutically acceptable aqueous carrier or vehicle phentolamine mesylate that exhibits an XRPD pattern that is substantially the same as that depicted in FIG. 1A or FIG. 1C to provide an ophthalmic solution in which the phentolamine mesylate that exhibits an XRPD pattern that is substantially the same as that depicted in FIG. 1A or FIG. 1C is dissolved and (b) administering to the subject an effective amount of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern comprising a peak at 8.4±0.2 degrees 2-theta and a peak at 16.3±0.2 degrees 2-theta to provide an ophthalmic solution in which the phentolamine mesylate that exhibits an XRPD pattern comprising a peak at 8.4±0.2 degrees 2-theta and a peak at 16.3±0.2 degrees 2-theta is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern that is substantially the same as that depicted in FIG. 2A to provide an ophthalmic solution in which the phentolamine mesylate that exhibits an XRPD pattern that is substantially the same as that depicted in FIG. 2A is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern comprising a Table 3 peak having a relative peak intensity (%) of greater than 30% to provide an ophthalmic solution in which the phentolamine mesylate that exhibits an XRPD pattern comprising a Table 3 peak having a relative peak intensity (%) of greater than 30% is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta to provide an ophthalmic solution in which the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern that is substantially the same as that depicted in FIG. 3A to provide an ophthalmic solution in which the phentolamine mesylate that exhibits an XRPD pattern that is substantially the same as that depicted in FIG. 3A is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern comprising a Table 4 peak having a relative peak intensity (%) of greater than 30% to provide an ophthalmic solution in which the phentolamine mesylate that exhibits an XRPD pattern comprising a Table 4 peak having a relative peak intensity (%) of greater than 30% is dissolved and (b) administering to the subject an effective amount of the ophthalmic solution. In some embodiments, the pharmacologically induced mydriasis is produced by an adrenergic agonist. In some embodiments, the adrenergic agonist is phenylephrine. In some embodiments, the pharmacologically induced mydriasis is produced by a parasympatholytic agent. In some embodiments, the parasympatholytic agent is tropicamide. In some embodiments, the administering is topically instilling into one or both eyes of the subject.

The invention further provides methods for treating or reversing pharmacologically induced mydriasis in a subject in need thereof, comprising (a) dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (b) administering to the subject an effective amount of the ophthalmic solution. In some embodiments, the pharmacologically induced mydriasis produced by an adrenergic agonist. In some embodiments, the adrenergic agonist is phenylephrine. In some embodiments, the pharmacologically induced mydriasis produced by a parasympatholytic agent. In some embodiments, the parasympatholytic agent is tropicamide. In some embodiments, the administering is topically instilling into one or both eyes of the subject.

In some embodiments, adrenergic agonist is an alpha-1 adrenergic agonist. In some embodiments, adrenergic agonist is 6-fluoronorepinephrine, amidephrine, buspirone, cirazoline, corbadrine, deoxyepinephrine, desglymidodrine, dexisometheptene, dipivefrine, dopamine, droxidopa (L-DOPS), epinephrine, etilefrine, etilevodopa, ethylnorepinephrine, ibopamine, indanidine, isometheptene, levodopa, L-phenylalanine, L-tyrosine, melevodopa, metaraminol, methoxamine, methyldopa, midodrine, naphazoline, norepinephrine, octopamine, oxymetazoline, phenylephrine, phenylpropanolamine, synephrine, tetryzoline, tiamenidine, XP21279, or xylometazoline. In some embodiments, the adrenergic agonist is phenylephrine, methoxamine, midodrine, or oxymetazoline. In some embodiments, the adrenergic agonist is phenylephrine.

In some embodiments, the adrenergic agonist is an alpha-2 adrenergic agonist. In some embodiments, the adrenergic agonist is (R)-3-nitrobiphenyline, (S)-naphthylmedetomidine, 6-fluoronorepinephrine, amitraz, apraclonidine, brimonidine, clonidine, corbadrine, deoxyepinephrine, detomidine, dexmedetomidine, dihydroergotamine, dipivefrine, dopamine, droxidopa (L-DOPS), etilevodopa, ergotamine, epinephrine, etilefrine, ethylnorepinephrine, guanabenz, guanfacine, guanoxabenz, ibopamine, levodopa, L-phenylalanine, L-tyrosine, lofexidine, medetomidine, melevodopa, methyldopa, mivazerol, moxonidine, naphazoline, norepinephrine, oxymetazoline, phenylpropanolamine, piperoxan, N-(pyridin-4-yl)-7-chloronaphthalen-1-amine, rezatomidine, rilmenidine, romifidine, talipexole, tasipimidine, tetryzoline, tiamenidine, tizanidine, tolonidine, urapidil, vatinoxan, XP21279, xylazine, or xylometazoline. In some embodiments, the adrenergic agonist is α-methyldopa, clonidine, brimonidine, or dexmedetomidine.

In some embodiments, the adrenergic agonist is a selective agonist. In some embodiments, the adrenergic agonist is a non-selective agonist. In some embodiments, the adrenergic agonist is adrenaline, noradrenaline, or dopamine.

In some embodiments, the parasympatholytic agent is atropine, cyclopentolate, homatropine, scopolamine or tropicamide.

In some embodiments, the compound of the invention is useful for treating or preventing an ocular disease or condition.

Accordingly, the invention further provides methods for treating or preventing an ocular disease or condition, comprising administering to a subject in need thereof an effective amount of a compound of the invention or a composition of the invention. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern comprising a peak at 8.4±0.2 degrees 2-theta and a peak at 16.3±0.2 degrees 2-theta. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern that is substantially the same as that depicted in FIG. 2A. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta.

The invention further provides methods for treating or preventing an ocular disease or condition, comprising administering to a subject in need thereof an effective amount of phentolamine mesylate that exhibits an XRPD pattern that is substantially the same as that depicted in FIG. 3A. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of a composition of the invention. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern comprising a peak at 8.4±0.2 degrees 2-theta and a peak at 16.3±0.2 degrees 2-theta and (ii) a pharmaceutically acceptable carrier or vehicle. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern that is substantially the same as that depicted in FIG. 2A and (ii) a pharmaceutically acceptable carrier or vehicle. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern comprising a Table 3 peak having a relative peak intensity (%) of greater than 30% and (ii) a pharmaceutically acceptable carrier or vehicle. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta and (ii) a pharmaceutically acceptable carrier or vehicle. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern that is substantially the same as that depicted in FIG. 3A and (ii) a pharmaceutically acceptable carrier or vehicle. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern comprising a Table 4 peak having a relative peak intensity (%) of greater than 30% and (ii) a pharmaceutically acceptable carrier or vehicle. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13. In some embodiments, the administering is topically instilling into one or both eyes of the subject.

The invention further provides methods for treating or preventing an ocular disease or condition, comprising administering to a subject in need thereof an effective amount of a composition comprising (i) phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (ii) a pharmaceutically acceptable carrier or vehicle.

The invention further provides methods for treating or preventing an ocular disease or condition, comprising administering to a subject in need thereof an effective amount of an ophthalmic solution in which a compound of the invention is dissolved. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern comprising a peak at 8.4±0.2 degrees 2-theta and a peak at 16.3±0.2 degrees 2-theta is dissolved. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern that is substantially the same as that depicted in FIG. 2A is dissolved. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern comprising a Table 3 peak having a relative peak intensity (%) of greater than 30% is dissolved. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern that is substantially the same as that depicted in FIG. 3A is dissolved. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern comprising a Table 4 peak having a relative peak intensity (%) of greater than 30% is dissolved. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for treating or preventing an ocular disease or condition, comprising administering to a subject in need thereof an effective amount of an ophthalmic solution in which phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle a compound of the invention to provide an ophthalmic solution in which the compound of the invention is dissolved and (b) administering to the subject the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern comprising a peak at 8.4±0.2 degrees 2-theta and a peak at 16.3±0.2 degrees 2-theta to provide an ophthalmic solution in which the phentolamine mesylate that exhibits an XRPD pattern comprising a peak at 8.4±0.2 degrees 2-theta and a peak at 16.3±0.2 degrees 2-theta is dissolved and (b) administering to the subject an effective amount of the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern that is substantially the same as that depicted in FIG. 2A to provide an ophthalmic solution in which the phentolamine mesylate that exhibits an XRPD pattern that is substantially the same as that depicted in FIG. 2A is dissolved and (b) administering to the subject an effective amount of the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern comprising a Table 3 peak having a relative peak intensity (%) of greater than 30% to provide an ophthalmic solution in which the phentolamine mesylate that exhibits an XRPD pattern comprising a Table 3 peak having a relative peak intensity (%) of greater than 30% is dissolved and (b) administering to the subject an effective amount of the ophthalmic solution. In some embodiments, the administering is topically instilling into one or both eyes of the subject.

The invention further provides for treating or preventing an ocular disease or condition in a subject in need thereof, comprising (a) dissolving in a pharmaceutically acceptable aqueous carrier or vehicle phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta to provide an ophthalmic solution in which the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved and (b) administering to the subject an effective amount of the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern that is substantially the same as that depicted in FIG. 3A to provide an ophthalmic solution in which the phentolamine mesylate that exhibits an XRPD pattern that is substantially the same as that depicted in FIG. 3A is dissolved and (b) administering to the subject an effective amount of the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern comprising a Table 4 peak having a relative peak intensity (%) of greater than 30% to provide an ophthalmic solution in which the phentolamine mesylate that exhibits an XRPD pattern comprising a Table 4 peak having a relative peak intensity (%) of greater than 30% is dissolved and (b) administering to the subject an effective amount of the ophthalmic solution. In some embodiments, the administering is topically instilling into one or both eyes of the subject.

The invention further provides methods for treating or preventing an ocular disease or condition in a subject in need thereof, comprising (a) dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (b) administering to the subject an effective amount of the ophthalmic solution. In some embodiments, the administering is topically instilling into one or both eyes of the subject.

In some embodiments, the ocular disease or condition is a dim or night vision disturbance.

In some embodiments, the ocular disease or condition is presbyopia. In some embodiments, the ocular disease or condition is presbyopia, and the methods for treating or preventing presbyopia further comprise administering to the subject an effective amount of pilocarpine or a pharmaceutically acceptable salt thereof. In some embodiments, the pharmaceutically acceptable salt of pilocarpine is pilocarpine hydrochloride. In some embodiments, the composition of the invention comprises a compound of the invention and pilocarpine or a pharmaceutically acceptable salt thereof. In some embodiments, the compound of the invention is administered separately from pilocarpine or a pharmaceutically acceptable salt thereof.

In some embodiments, the ocular disease or condition is diabetic retinal disease. In some embodiments, diabetic retinal disease is diabetic retinopathy (DR) or diabetic macular edema (DME). In some embodiments, the DR is moderately severe non-proliferative DR or mild proliferative DR. In some embodiments, the DME is DME without loss of central vision.

In some embodiments, the ocular disease or condition is retinopathy of prematurity, DR, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, or sickle cell retinopathy. In some embodiments, the ocular disease or condition is DR, and the DR is proliferative diabetic retinopathy. In some embodiments, the ocular disease or condition is macular degeneration, and the macular degeneration is advanced macular degeneration. In some embodiments, the macular degeneration is wet age-related macular degeneration. In some embodiments, the macular degeneration is dry age-related macular degeneration. In some embodiments, the ocular disease or condition is ocular neovascularization, and the ocular neovascularization is corneal neovascularization or retinal neovascularization. In some embodiments, retinal vein occlusion is central retinal vein occlusion or branch retinal vein occlusion.

In some embodiments, the ocular disease or condition is geographic atrophy, choroidal neovascularization, or corneal graft rejection.

In some embodiments, the ocular disease or condition is glaucoma. In some embodiments, the glaucoma is congenital glaucoma. In some embodiments, the glaucoma is open-angle glaucoma. In some embodiments, the glaucoma is closed-angle glaucoma. In some embodiments, the glaucoma is primary glaucoma. In some embodiments, the glaucoma is secondary glaucoma. In some embodiments, the glaucoma is pigmentary glaucoma, pseudoexfoliative glaucoma, traumatic glaucoma, neovascular glaucoma, uveitic glaucoma, or glaucoma due to irido comeal endothelial syndrome. In some embodiments, the glaucoma is normal tension glaucoma.

In some embodiments, the ocular disease or condition is ocular hypertension. In some embodiments, the ocular hypertension is ocular hypertension after ocular surgery.

In some embodiments, the ocular disease or condition is keratoconus.

In some embodiments, the ocular disease or condition is non-arteritic anterior ischemic optic neuropathy.

In some embodiments, the subject's eye has an intraocular pressure of from about 12 mmHg to about 22 mmHg. In some embodiments, the subject's eye has an intraocular pressure of from about 15 mmHg to about 22 mmHg. In some embodiments, the subject's eye has an intraocular pressure of from about 18 mmHg to about 22 mmHg. In some embodiments, the subject's eye has an intraocular pressure of from about 10 mmHg to about 12 mmHg, from about 12 mmHg to about 14 mmHg, from about 14 mmHg to about 16 mmHg, from about 16 mmHg to about 18 mmHg, from about 18 mmHg to about 20 mmHg, or from about 20 mmHg to about 22 mmHg. In some embodiments, the subject's eye has an intraocular pressure of less than about 15 mmHg, less than about 17 mmHg, less than about 19 mmHg, less than about 21 mmHg or less than about 22 mmHg.

In some embodiments, the subject's eye has an intraocular pressure of from about 12 mmHg to about 26 mmHg. In some embodiments, the subject's eye has an intraocular pressure of from about 12 mmHg to about 24 mmHg.

In some embodiments, the subject's eye has an intraocular pressure of from about 17 mmHg to about 36 mmHg, from about 17 mmHg to about 32 mmHg, from about 17 mmHg to about 28 mmHg, from about 17 mmHg to about 26 mmHg, from about 17 mmHg to about 24 mmHg, or from about 17 mmHg to about 22 mmHg. In some embodiments, the subject's eye has an intraocular pressure of from about 20 mmHg to about 36 mmHg, from about 20 mmHg to about 32 mmHg, from about 20 mmHg to about 28 mmHg, from about 20 mmHg to about 26 mmHg, from about 20 mmHg to about 24 mmHg, or from about 20 mmHg to about 22 mmHg. In some embodiments, the subject's eye has an intraocular pressure of from about 20 mmHg to about 26 mmHg, from about 20 mmHg to about 25 mmHg, from about 20 mmHg to about 24 mmHg, from about 20 mmHg to about 23 mmHg, or from about 20 mmHg to about 22 mmHg. In some embodiments, the subject's eye has an intraocular pressure of less than about 23 mmHg, less than about 24 mmHg, less than about 25 mmHg, or less than about 26 mmHg.

The invention further provides methods for treating or preventing diabetic retinal disease, retinopathy of prematurity, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, sickle cell retinopathy, geographic atrophy, choroidal neovascularization, or corneal graft rejection, comprising administering to a subject in need thereof an effective amount of: a compound of the invention; a composition of the invention; phentolamine mesylate that exhibits an XRPD pattern that is substantially the same as that depicted in FIG. 1A or FIG. 1C; a composition comprising (i) phentolamine mesylate that exhibits an XRPD pattern that is substantially the same as that depicted in FIG. 1A or FIG. 1C and (ii) a pharmaceutically acceptable carrier or vehicle; or a composition comprising a pharmaceutically acceptable aqueous carrier or vehicle in which phentolamine mesylate that exhibits an XRPD pattern that is substantially the same as that depicted in FIG. 1A or FIG. 1C is dissolved. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, diabetic retinal disease is diabetic retinopathy (DR) or diabetic macular edema (DME). In some embodiments, the DR is moderately severe non-proliferative DR or mild proliferative DR. In some embodiments, the DME is DME without loss of central vision. In some embodiments, the administering is topically instilling into one or both eyes of the subject.

The invention further provides methods for treating or preventing diabetic retinal disease, retinopathy of prematurity, pathological myopia, hypertensive retinopathy, occlusive vasculitis, polypoidal choroidal vasculopathy, diabetic macular edema, uveitic macular edema, retinal vein occlusion, ocular neovascularization, ocular histoplasmosis, neovascular glaucoma, retinoblastoma, macular degeneration, retrolental fibroplasias, retinal angiomatous proliferation, dry eye disease, uveitis, thyroid eye disease, sickle cell retinopathy, geographic atrophy, choroidal neovascularization, or corneal graft rejection in a subject in need thereof, comprising (a) dissolving in a pharmaceutically acceptable aqueous carrier or vehicle phentolamine mesylate that exhibits an XRPD pattern that is substantially the same as that depicted in FIG. 1A or FIG. 1C to provide an ophthalmic solution in which the phentolamine mesylate that exhibits an XRPD pattern that is substantially the same as that depicted in FIG. 1A or FIG. 1C is dissolved and (b) administering to the subject an effective amount of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, diabetic retinal disease is diabetic retinopathy (DR) or diabetic macular edema (DME). In some embodiments, the DR is moderately severe non-proliferative DR or mild proliferative DR. In some embodiments, the DME is DME without loss of central vision. In some embodiments, the administering is topically instilling into one or both eyes of the subject.

In some embodiments, the compound of the invention is useful for inhibiting the contraction of smooth muscle of the iris.

Accordingly, the invention further provides methods for inhibiting the contraction of smooth muscle of the iris, comprising administering to a subject in need thereof an effective amount of a compound of the invention or a composition of the invention. In some embodiments, the administering is topically instilling into one or both eyes of the subject.

The invention further provides methods for inhibiting the contraction of smooth muscle of the iris, comprising administering to a subject in need thereof an effective amount of phentolamine mesylate that exhibits an XRPD pattern comprising a peak at 8.4±0.2 degrees 2-theta and a peak at 16.3±0.2 degrees 2-theta.

The invention further provides methods for inhibiting the contraction of smooth muscle of the iris, comprising administering to a subject in need thereof an effective amount of phentolamine mesylate that exhibits an XRPD pattern that is substantially the same as that depicted in FIG. 2A. In some embodiments, the administering is topically instilling into one or both eyes of the subject.

The invention further provides methods for inhibiting the contraction of smooth muscle of the iris, comprising administering to a subject in need thereof an effective amount of phentolamine mesylate that exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta.

The invention further provides methods for inhibiting the contraction of smooth muscle of the iris, comprising administering to a subject in need thereof an effective amount of phentolamine mesylate that exhibits an XRPD pattern that is substantially the same as that depicted in FIG. 3A. In some embodiments, the administering is topically instilling into one or both eyes of the subject.

The invention further provides methods for inhibiting the contraction of smooth muscle of the iris, comprising administering to a subject in need thereof an effective amount of phentolamine mesylate that exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of a composition of the invention. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern comprising a peak at 8.4±0.2 degrees 2-theta and a peak at 16.3±0.2 degrees 2-theta and (ii) a pharmaceutically acceptable carrier or vehicle. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern that is substantially the same as that depicted in FIG. 2A and (ii) a pharmaceutically acceptable carrier or vehicle. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern comprising a Table 3 peak having a relative peak intensity (%) of greater than 30% and (ii) a pharmaceutically acceptable carrier or vehicle. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta and (ii) a pharmaceutically acceptable carrier or vehicle. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern that is substantially the same as that depicted in FIG. 3A and (ii) a pharmaceutically acceptable carrier or vehicle. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern comprising a Table 4 peak having a relative peak intensity (%) of greater than 30% and (ii) a pharmaceutically acceptable carrier or vehicle. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13. In some embodiments, the administering is topically instilling into one or both eyes of the subject.

The invention further provides methods for inhibiting the contraction of smooth muscle of the iris, comprising administering to a subject in need thereof an effective amount of a composition comprising (i) phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (ii) a pharmaceutically acceptable carrier or vehicle. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which a compound of the invention is dissolved. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern comprising a peak at 8.4±0.2 degrees 2-theta and a peak at 16.3±0.2 degrees 2-theta is dissolved. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern that is substantially the same as that depicted in FIG. 2A is dissolved. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern comprising a Table 3 peak having a relative peak intensity (%) of greater than 30% is dissolved. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern that is substantially the same as that depicted in FIG. 3A is dissolved. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern comprising a Table 4 peak having a relative peak intensity (%) of greater than 30% is dissolved. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for inhibiting the contraction of smooth muscle of the iris, comprising administering to a subject in need thereof an effective amount of an ophthalmic solution in which phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle a compound of the invention to provide an ophthalmic solution in which the compound of the invention is dissolved and (b) administering to the subject the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern comprising a peak at 8.4±0.2 degrees 2-theta and a peak at 16.3±0.2 degrees 2-theta to provide an ophthalmic solution in which the phentolamine mesylate that exhibits an XRPD pattern comprising a peak at 8.4±0.2 degrees 2-theta and a peak at 16.3±0.2 degrees 2-theta is dissolved and (b) administering to the subject an effective amount of the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern that is substantially the same as that depicted in FIG. 2A to provide an ophthalmic solution in which the phentolamine mesylate that exhibits an XRPD pattern that is substantially the same as that depicted in FIG. 2A is dissolved and (b) administering to the subject an effective amount of the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern comprising a Table 3 peak having a relative peak intensity (%) of greater than 30% to provide an ophthalmic solution in which the phentolamine mesylate that exhibits an XRPD pattern comprising a Table 3 peak having a relative peak intensity (%) of greater than 30% is dissolved and (b) administering to the subject an effective amount of the ophthalmic solution. In some embodiments, the administering is topically instilling into one or both eyes of the subject.

The invention further provides for inhibiting the contraction of smooth muscle of the iris in a subject in need thereof, comprising (a) dissolving in a pharmaceutically acceptable aqueous carrier or vehicle phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta to provide an ophthalmic solution in which the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved and (b) administering to the subject an effective amount of the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern that is substantially the same as that depicted in FIG. 3A to provide an ophthalmic solution in which the phentolamine mesylate that exhibits an XRPD pattern that is substantially the same as that depicted in FIG. 3A is dissolved and (b) administering to the subject an effective amount of the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern comprising a Table 4 peak having a relative peak intensity (%) of greater than 30% to provide an ophthalmic solution in which the phentolamine mesylate that exhibits an XRPD pattern comprising a Table 4 peak having a relative peak intensity (%) of greater than 30% is dissolved and (b) administering to the subject an effective amount of the ophthalmic solution. In some embodiments, the administering is topically instilling into one or both eyes of the subject.

The invention further provides methods for inhibiting the contraction of smooth muscle of the iris in a subject in need thereof, comprising (a) dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (b) administering to the subject an effective amount of the ophthalmic solution. In some embodiments, the administering is topically instilling into one or both eyes of the subject.

In some embodiments, the compound of the invention is useful for reducing pupil diameter.

Accordingly, the invention further provides methods for reducing pupil diameter, comprising administering to a subject in need thereof an effective amount of a compound of the invention or a composition of the invention. In some embodiments, the administering is topically instilling into one or both eyes of the subject.

The invention further provides methods for reducing pupil diameter, comprising administering to a subject in need thereof an effective amount of phentolamine mesylate that exhibits an XRPD pattern comprising a peak at 8.4±0.2 degrees 2-theta and a peak at 16.3±0.2 degrees 2-theta. In some embodiments, the administering is topically instilling into one or both eyes of the subject.

The invention further provides methods for reducing pupil diameter, comprising administering to a subject in need thereof an effective amount of phentolamine mesylate that exhibits an XRPD pattern that is substantially the same as that depicted in FIG. 2A.

The invention further provides methods reducing pupil diameter, comprising administering to a subject in need thereof an effective amount of phentolamine mesylate that exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the administering is topically instilling into one or both eyes of the subject.

The invention further provides methods for reducing pupil diameter, comprising administering to a subject in need thereof an effective amount of phentolamine mesylate that exhibits an XRPD pattern that is substantially the same as that depicted in FIG. 3A.

The invention further provides methods for reducing pupil diameter, comprising administering to a subject in need thereof an effective amount of phentolamine mesylate that exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of a composition of the invention. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern comprising a peak at 8.4±0.2 degrees 2-theta and a peak at 16.3±0.2 degrees 2-theta and (ii) a pharmaceutically acceptable carrier or vehicle. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern that is substantially the same as that depicted in FIG. 2A and (ii) a pharmaceutically acceptable carrier or vehicle. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern comprising a Table 3 peak having a relative peak intensity (%) of greater than 30% and (ii) a pharmaceutically acceptable carrier or vehicle. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta and (ii) a pharmaceutically acceptable carrier or vehicle. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern that is substantially the same as that depicted in FIG. 3A and (ii) a pharmaceutically acceptable carrier or vehicle. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern comprising a Table 4 peak having a relative peak intensity (%) of greater than 30% and (ii) a pharmaceutically acceptable carrier or vehicle. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13. In some embodiments, the administering is topically instilling into one or both eyes of the subject.

The invention further provides methods for reducing pupil diameter, comprising administering to a subject in need thereof an effective amount of a composition comprising (i) phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (ii) a pharmaceutically acceptable carrier or vehicle. In some embodiments, the administering is topically instilling into one or both eyes of the subject.

The invention further provides methods for reducing pupil diameter, comprising administering to a subject in need thereof an effective amount of an ophthalmic solution in which a compound of the invention is dissolved. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern comprising a peak at 8.4±0.2 degrees 2-theta and a peak at 16.3±0.2 degrees 2-theta is dissolved. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern that is substantially the same as that depicted in FIG. 2A is dissolved. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern comprising a Table 3 peak having a relative peak intensity (%) of greater than 30% is dissolved. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern that is substantially the same as that depicted in FIG. 3A is dissolved. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern comprising a Table 4 peak having a relative peak intensity (%) of greater than 30% is dissolved. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for reducing pupil diameter, comprising administering to a subject in need thereof an effective amount of an ophthalmic solution in which phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle a compound of the invention to provide an ophthalmic solution in which the compound of the invention is dissolved and (b) administering to the subject the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern comprising a peak at 8.4±0.2 degrees 2-theta and a peak at 16.3±0.2 degrees 2-theta to provide an ophthalmic solution in which the phentolamine mesylate that exhibits an XRPD pattern comprising a peak at 8.4±0.2 degrees 2-theta and a peak at 16.3±0.2 degrees 2-theta is dissolved and (b) administering to the subject an effective amount of the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern that is substantially the same as that depicted in FIG. 2A to provide an ophthalmic solution in which the phentolamine mesylate that exhibits an XRPD pattern that is substantially the same as that depicted in FIG. 2A is dissolved and (b) administering to the subject an effective amount of the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern comprising a Table 3 peak having a relative peak intensity (%) of greater than 30% to provide an ophthalmic solution in which the phentolamine mesylate that exhibits an XRPD pattern comprising a Table 3 peak having a relative peak intensity (%) of greater than 30% is dissolved and (b) administering to the subject an effective amount of the ophthalmic solution. In some embodiments, the administering is topically instilling into one or both eyes of the subject.

The invention further provides for reducing pupil diameter in a subject in need thereof, comprising (a) dissolving in a pharmaceutically acceptable aqueous carrier or vehicle phentolamine mesylate that exhibits XRPD pattern comprising a peak at 8.3±0.2 degrees 2-theta, a peak at 13.3±0.2 degrees 2-theta and a peak at 19.7±0.2 degrees 2-theta to provide an ophthalmic solution in which the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved and (b) administering to the subject an effective amount of the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern that is substantially the same as that depicted in FIG. 3A to provide an ophthalmic solution in which the phentolamine mesylate that exhibits an XRPD pattern that is substantially the same as that depicted in FIG. 3A is dissolved and (b) administering to the subject an effective amount of the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern comprising a Table 4 peak having a relative peak intensity (%) of greater than 30% to provide an ophthalmic solution in which the phentolamine mesylate that exhibits an XRPD pattern comprising a Table 4 peak having a relative peak intensity (%) of greater than 30% is dissolved and (b) administering to the subject an effective amount of the ophthalmic solution. In some embodiments, the administering is topically instilling into one or both eyes of the subject.

The invention further provides methods for reducing pupil diameter in a subject in need thereof, comprising (a) dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (b) administering to the subject an effective amount of the ophthalmic solution. In some embodiments, the administering is topically instilling into one or both eyes of the subject.

In some embodiments, the compound of the invention is useful for improving visual contrast sensitivity or visual acuity.

Accordingly, the invention further provides methods for improving visual contrast sensitivity or visual acuity, comprising administering to a subject in need thereof an effective amount of a compound of the invention or a composition of the invention. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern comprising a peak at 8.4±0.2 degrees 2-theta and a peak at 16.3±0.2 degrees 2-theta. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern that is substantially the same as that depicted in FIG. 2A. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern comprising a Table 3 peak having a relative peak intensity (%) of greater than 30%. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern that is substantially the same as that depicted in FIG. 3A. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern comprising a Table 4 peak having a relative peak intensity (%) of greater than 30%. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of a composition of the invention. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern comprising a peak at 8.4±0.2 degrees 2-theta and a peak at 16.3±0.2 degrees 2-theta and (ii) a pharmaceutically acceptable carrier or vehicle. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern that is substantially the same as that depicted in FIG. 2A and (ii) a pharmaceutically acceptable carrier or vehicle. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern comprising a Table 3 peak having a relative peak intensity (%) of greater than 30% and (ii) a pharmaceutically acceptable carrier or vehicle. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta and (ii) a pharmaceutically acceptable carrier or vehicle. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern that is substantially the same as that depicted in FIG. 3A and (ii) a pharmaceutically acceptable carrier or vehicle. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern comprising a Table 4 peak having a relative peak intensity (%) of greater than 30% and (ii) a pharmaceutically acceptable carrier or vehicle. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13. In some embodiments, the administering is topically instilling into one or both eyes of the subject.

The invention further provides methods for improving visual contrast sensitivity or visual acuity, comprising administering to a subject in need thereof an effective amount of a composition comprising (i) phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13, and (ii) a pharmaceutically acceptable carrier or vehicle.

The invention further provides methods for improving visual contrast sensitivity or visual acuity, comprising administering to a subject in need thereof an effective amount of an ophthalmic solution in which a compound of the invention is dissolved. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern comprising a peak at 8.4±0.2 degrees 2-theta and a peak at 16.3±0.2 degrees 2-theta is dissolved. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern that is substantially the same as that depicted in FIG. 2A is dissolved. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern comprising a Table 3 peak having a relative peak intensity (%) of greater than 30% is dissolved. In some embodiments, the phentolamine mesylate exhibits an XRPD pattern comprising a Table 3 peak having a relative peak intensity (%) of greater than 40%. In some embodiments, the phentolamine mesylate exhibits an XRPD pattern comprising a Table 3 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern that is substantially the same as that depicted in FIG. 3A is dissolved. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern comprising a Table 4 peak having a relative peak intensity (%) of greater than 30% is dissolved. In some embodiments, the phentolamine mesylate exhibits an XRPD pattern comprising a Table 4 peak having a relative peak intensity (%) of greater than 40%. In some embodiments, the phentolamine mesylate exhibits an XRPD pattern comprising a Table 4 peak having a relative peak intensity (%) of greater than 50%. In some embodiments, the administering is topically instilling into one or both eyes of the subject.

The invention further provides methods for improving visual contrast sensitivity or visual acuity, comprising administering to a subject in need thereof an effective amount of an ophthalmic solution in which phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle a compound of the invention to provide an ophthalmic solution in which the compound of the invention is dissolved and (b) administering to the subject the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern comprising a peak at 8.4±0.2 degrees 2-theta and a peak at 16.3±0.2 degrees 2-theta to provide an ophthalmic solution in which the phentolamine mesylate that exhibits an XRPD pattern comprising a peak at 8.4±0.2 degrees 2-theta and a peak at 16.3±0.2 degrees 2-theta is dissolved and (b) administering to the subject an effective amount of the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern that is substantially the same as that depicted in FIG. 2A to provide an ophthalmic solution in which the phentolamine mesylate that exhibits an XRPD pattern that is substantially the same as that depicted in FIG. 2A is dissolved and (b) administering to the subject an effective amount of the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern comprising a Table 3 peak having a relative peak intensity (%) of greater than 30% to provide an ophthalmic solution in which the phentolamine mesylate that exhibits an XRPD pattern comprising a Table 3 peak having a relative peak intensity (%) of greater than 30% is dissolved and (b) administering to the subject an effective amount of the ophthalmic solution. In some embodiments, the administering is topically instilling into one or both eyes of the subject.

The invention further provides for improving visual contrast sensitivity or visual acuity in a subject in need thereof, comprising (a) dissolving in a pharmaceutically acceptable aqueous carrier or vehicle phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta to provide an ophthalmic solution in which the phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta is dissolved and (b) administering to the subject an effective amount of the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern that is substantially the same as that depicted in FIG. 3A to provide an ophthalmic solution in which the phentolamine mesylate that exhibits an XRPD pattern that is substantially the same as that depicted in FIG. 3A is dissolved and (b) administering to the subject an effective amount of the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern comprising a Table 4 peak having a relative peak intensity (%) of greater than 30% to provide an ophthalmic solution in which the phentolamine mesylate that exhibits an XRPD pattern comprising a Table 4 peak having a relative peak intensity (%) of greater than 30% is dissolved and (b) administering to the subject an effective amount of the ophthalmic solution. In some embodiments, the administering is topically instilling into one or both eyes of the subject.

The invention further provides methods for improving visual contrast sensitivity or visual acuity in a subject in need thereof, comprising (a) dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 to provide an ophthalmic solution in which the phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13 is dissolved and (b) administering to the subject an effective amount of the ophthalmic solution. In some embodiments, the administering is topically instilling into one or both eyes of the subject.

In some embodiments, administering an ophthalmic solution in which phentolamine mesylate described herein is dissolved is topically instilling the ophthalmic solution into one or both eyes of the subject.

In some embodiments, the administering is topically instilling into one or both eyes of the subject once a day an ophthalmic solution in which phentolamine mesylate described herein is dissolved. In some embodiments, the administering is topically instilling into one or both eyes of the subject twice a day an ophthalmic solution in which phentolamine mesylate described herein is dissolved. In some embodiments, the administering is topically instilling into one or both eyes of the subject more than twice per day an ophthalmic solution in which phentolamine mesylate described herein is dissolved.

In some embodiments, the administering is topically instilling one or two drops of an ophthalmic solution in which phentolamine mesylate described herein is dissolved daily into one or both eyes of the subject. In some embodiments, the administering is topically instilling one drop of an ophthalmic solution in which phentolamine mesylate described herein is dissolved daily into one or both eyes of the subject. In some embodiments, the administering is topically instilling two drops of an ophthalmic solution in which phentolamine mesylate described herein is dissolved daily into one or both eyes of the subject. In some embodiments, the administering is topically instilling one drop of an ophthalmic solution in which phentolamine mesylate described herein is dissolved daily in each eye of the subject. In some embodiments, the administering is topically instilling two drops of an ophthalmic solution in which phentolamine mesylate described herein is dissolved daily in each eye of the subject. In some embodiments, the administering is before bedtime. In some embodiments, the administering is in the evening. In some embodiments, the administering is between 8 p.m. to 10 p.m.

In some embodiments, the administering is topically instilling one or two drops of an ophthalmic solution in which phentolamine mesylate described herein is dissolved twice daily into one or both eyes of the subject. In some embodiments, the administering is topically instilling one drop of an ophthalmic solution in which phentolamine mesylate described herein is dissolved twice daily into one or both eyes of the subject. In some embodiments, the administering is topically instilling two drops of an ophthalmic solution in which phentolamine mesylate described herein is dissolved twice daily into one or both eyes of the subject.

In some embodiments, the effective amount of the phentolamine mesylate is about 0.01 mg to about 100 mg. In some embodiments, the effective amount of the phentolamine mesylate is about 0.05 mg to about 50 mg. In some embodiments, the effective amount of the phentolamine mesylate is about 0.1 mg to about 100 mg. In some embodiments, the effective amount of the phentolamine mesylate is about 1 mg to about 25 mg. In some embodiments, the effective amount of the phentolamine mesylate is about 5 mg to about 10 mg. In some embodiments, the effective amount of the phentolamine mesylate is a daily amount.

In some embodiments, the effective amount of the phentolamine mesylate is about 0.1 mg to about 2.0 mg, about 0.2 mg to about 0.7 mg, about 0.4 mg to about 0.6 mg, or about 0.8 mg to about 1.2 mg. In some embodiments, the effective amount of the phentolamine mesylate is about 0.5 mg or about 1 mg. In some embodiments, the effective amount of the phentolamine mesylate is a daily amount.

In some embodiments, the effective amount of the phentolamine mesylate is about 0.1 mg to about 2.0 mg. In some embodiments, the effective amount of the phentolamine mesylate is about 0.1 mg to about 1.0 mg. In some embodiments, the effective amount of the phentolamine mesylate is about 0.2 mg to about 0.7 mg. In some embodiments, the effective amount of the phentolamine mesylate is about 0.4 mg to about 0.6 mg. In some embodiments, the effective amount of the phentolamine mesylate is about 0.25 mg, about 0.5 mg or about 1.0 mg. In some embodiments, the effective amount of the phentolamine mesylate is about 0.5 mg. In some embodiments, the effective amount of the phentolamine mesylate is a daily amount.

In some embodiments, the effective amount of the phentolamine mesylate is about 0.1 mg/day to about 20 mg/day. In some embodiments, the effective amount of the phentolamine mesylate is about 0.1 mg/day to about 10 mg/day. In some embodiments, the effective amount of the phentolamine mesylate is about 0.1 mg/day to about 5 mg/day. In some embodiments, the effective amount of the phentolamine mesylate is about 0.1 mg/day to about 2.0 mg/day. In some embodiments, the effective amount of the phentolamine mesylate is about 0.1 mg/day, about 0.2 mg/day, about 0.3 mg/day, about 0.4 mg/day, about 0.5 mg/day, about 0.6 mg/day, about 0.7 mg/day, about 0.8 mg/day, about 0.9 mg/day, about 1.0 mg/day, about 1.1 mg/day, about 1.2 mg/day, about 1.3 mg/day, about 1.4 mg/day, about 1.5 mg/day, about 1.6 mg/day, about 1.7 mg/day, about 1.8 mg/day, about 1.9 mg/day, or about 2.0 mg/day.

In some embodiments, the effective amount of the phentolamine mesylate is the effective amount of a compound of the invention or phentolamine mesylate that exhibits an XRPD pattern that is substantially the same as that depicted in FIG. 1A or FIG. 1C.

In some embodiments, the effective amount is one drop per eye of an ophthalmic solution which comprises about 0.35% to about 1% of a compound of the invention or phentolamine mesylate that exhibits an XRPD pattern that is substantially the same as that depicted in FIG. 1A or FIG. 1C, by weight or volume of the ophthalmic solution. In some embodiments, the effective amount is one drop per eye of an ophthalmic solution which comprises about 0.5%, 0.75%, or about 1% of a compound of the invention or phentolamine mesylate that exhibits an XRPD pattern that is substantially the same as that depicted in FIG. 1A or FIG. 1C, by weight or volume of the ophthalmic solution.

In some embodiments, the effective amount is two drops per eye of an ophthalmic solution which comprises about 0.35% to about 1% of a compound of the invention or phentolamine mesylate that exhibits an XRPD pattern that is substantially the same as that depicted in FIG. 1A or FIG. 1C, by weight or volume of the ophthalmic solution. In some embodiments, the effective amount is two drops per eye of an ophthalmic solution which comprises about 0.5%, 0.75%, or about 1% of a compound of the invention or phentolamine mesylate that exhibits an XRPD pattern that is substantially the same as that depicted in FIG. 1A or FIG. 1C, by weight or volume of the ophthalmic solution.

In some embodiments, one drop of an ophthalmic solution is about 0.03 mL to about 0.05 mL of the ophthalmic solution.

In some embodiments, the effective amount of a compound of the invention or phentolamine mesylate that exhibits an XRPD pattern that is substantially the same as that depicted in FIG. 1A or FIG. 1C is administered to the subject for at least three consecutive days, at least five consecutive days, or at least 14 consecutive days. In some embodiments, the effective amount of a compound of the invention or phentolamine mesylate that exhibits an XRPD pattern that is substantially the same as that depicted in FIG. 1A or FIG. 1C is administered to the subject for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days.

In some embodiments, an ophthalmic solution in which phentolamine mesylate described herein is dissolved is a first ophthalmic solution.

In some embodiments, the present methods further comprise administering to the subject an effective amount of pilocarpine or a pharmaceutically acceptable salt thereof. In some embodiments, the present methods further comprise administering to the subject an effective amount of a second ophthalmic solution in which pilocarpine or a pharmaceutically acceptable salt thereof is dissolved.

In some embodiments, administering the second ophthalmic solution is topically instilling the second ophthalmic solution into one or both eyes of the subject.

In some embodiments, the administering is topically instilling into one or both eyes of the subject once a day the second ophthalmic solution. In some embodiments, the administering is topically instilling into one or both eyes of the subject twice a day the second ophthalmic solution. In some embodiments, the administering is topically instilling into one or both eyes of the subject more than twice per day the second ophthalmic solution.

In some embodiments, the administering is topically instilling one or two drops daily into one or both eyes of the subject the second ophthalmic solution. In some embodiments, the administering is topically instilling one drop daily into one or both eyes of the subject the second ophthalmic solution. In some embodiments, the administering is topically instilling two drops daily into one or both eyes of the subject the second ophthalmic solution. In some embodiments, the administering is topically instilling one drop daily in each eye of the subject the second ophthalmic solution. In some embodiments, the administering is topically instilling two drops daily in each eye of the subject the second ophthalmic solution. In some embodiments, the administering is before bedtime. In some embodiments, the administering is in the evening. In some embodiments, the administering is between 8 p.m. to 10 p.m.

In some embodiments, the administering is topically instilling one or two drops twice daily into one or both eyes of the subject the second ophthalmic solution. In some embodiments, the administering is topically instilling one drop twice daily into one or both eyes of the subject the second ophthalmic solution. In some embodiments, the administering is topically instilling two drops twice daily into one or both eyes of the subject the second ophthalmic solution.

In some embodiments, the effective amount of pilocarpine, or a pharmaceutically acceptable salt thereof, is about 0.1 mg to about 2.0 mg, about 0.2 mg to about 0.7 mg, about 0.4 mg to about 0.6 mg, or about 0.8 mg to about 1.2 mg. In some embodiments, the effective amount is about 0.1 mg or about 1 mg. In some embodiments, the effective amount is about 0.1 mg or about 0.3 mg. In some embodiments, the effective amount is about 0.3 mg or about 0.6 mg. In some embodiments, the effective amount of pilocarpine, or a pharmaceutically acceptable salt thereof, is a daily amount.

In some embodiments, the effective amount of pilocarpine, or a pharmaceutically acceptable salt thereof, is about 0.1 mg, about 0.2 mg, about 0.3 mg, about 0.4 mg, about 0.5 mg, about 0.6 mg, about 0.7 mg, about 0.8 mg, about 0.9 mg, or about 1.0 mg. In some embodiments, the effective amount pilocarpine, or a pharmaceutically acceptable salt thereof, is a daily amount.

In some embodiments, the effective amount is one drop per eye of an ophthalmic solution that comprises about 0.1% to about 3% of pilocarpine, or a pharmaceutically acceptable salt thereof, by weight or volume of the ophthalmic solution. In some embodiments, the effective amount is one drop per eye of an ophthalmic solution that comprises about 0.1% w/w to about 3% w/w of pilocarpine, or a pharmaceutically acceptable salt thereof.

In some embodiments, the effective amount is one drop per eye of an ophthalmic solution that comprises about 0.2% to about 0.4% of pilocarpine, or a pharmaceutically acceptable salt thereof, by weight or volume of the ophthalmic solution. In some embodiments, the effective amount is one drop per eye of an ophthalmic solution that comprises about 0.2% w/w to about 0.4% w/w of pilocarpine, or a pharmaceutically acceptable salt thereof.

In some embodiments, the effective amount is one drop per eye of an ophthalmic solution that comprises about 0.1% to about 3% of pilocarpine, or a pharmaceutically acceptable salt thereof, by weight or volume of the ophthalmic solution. In some embodiments, the effective amount is one drop per eye of an ophthalmic solution that comprises about 1% w/w to about 2% w/w of pilocarpine, or a pharmaceutically acceptable salt thereof.

In some embodiments, the effective amount is one drop per eye of an ophthalmic solution that comprises about 0.01%, about 0.25%, about 0.5%, about 1%, about 2%, or about 4% of pilocarpine, or a pharmaceutically acceptable salt thereof, by weight or volume of the ophthalmic solution. In some embodiments, the effective amount is one drop per eye of an ophthalmic solution that comprises about 0.01% w/w, about 0.25% w/w, about 0.4% w/w, about 0.5% w/w, about 1% w/w, about 2% w/w, or about 4% w/w of pilocarpine, or a pharmaceutically acceptable salt thereof.

In some embodiments, an ophthalmic solution comprises (i) a compound of the invention or phentolamine mesylate that exhibits an XRPD pattern that is substantially the same as that depicted in FIG. 1A or FIG. 1C and (ii) pilocarpine, or a pharmaceutically acceptable salt thereof. In some embodiments, an ophthalmic solution comprising a compound of the invention or phentolamine mesylate that exhibits an XRPD pattern that is substantially the same as that depicted in FIG. 1A or FIG. 1C does not comprise pilocarpine, or a pharmaceutically acceptable salt thereof.

Compositions

In some embodiments, the composition of the invention or the composition comprising (i) phentolamine mesylate that exhibits an XRPD pattern that is substantially the same as that depicted in FIG. 1A or FIG. 1C, and (ii) a pharmaceutically acceptable carrier or vehicle, is an ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the ophthalmic solution is suitable for topical, e.g., ocular instillation; subconjunctival; intravitreal; retrobulbar; intracameral; or systemic administration.

In some embodiments, a composition of the invention or a composition comprising (i) phentolamine mesylate that exhibits an XRPD pattern that is substantially the same as that depicted in FIG. 1A or FIG. 1C, and (ii) a pharmaceutically acceptable carrier or vehicle, is an ophthalmic solution, or is coated on or incorporated in an ophthalmic drug delivery device. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, a compound of the invention or phentolamine mesylate that exhibits an XRPD pattern that is substantially the same as that depicted in FIG. 1A or FIG. 1C is dissolved in a pharmaceutically acceptable aqueous carrier or vehicle. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, the compositions disclosed herein are in the form of an ophthalmic solution. In some embodiments, the compound of the invention or phentolamine mesylate that exhibits an XRPD pattern that is substantially the same as that depicted in FIG. 1A or FIG. 1C is dissolved in the ophthalmic solution in an amount of about 0.5% to about 2% by weight of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount that is molar equivalent to about 0.5% to about 5% of phentolamine mesylate by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount that is molar equivalent to about 0.35% or about 1% of phentolamine mesylate by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount that is molar equivalent to about 0.37% or about 0.5% of phentolamine mesylate by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount of about 0.35% or about 0.75% by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount of about 0.75% by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount of about 0.75% by weight the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the compound of the invention or phentolamine mesylate that exhibits an XRPD pattern that is substantially the same as that depicted in FIG. 1A or FIG. 1C is dissolved in the ophthalmic solution in an amount of about 0.75% by volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, the composition comprises about 1% of a compound of the invention or phentolamine mesylate that exhibits an XRPD pattern that is substantially the same as that depicted in FIG. 1A or FIG. 1C by weight of the composition. In some same as that depicted in FIG. 1A. In some embodiments, the phentolamine mesylate exhibits an XRPD pattern that is substantially the same as that depicted in FIG. 1C. In some embodiments, the composition comprises about 1% of a compound of the invention or phentolamine mesylate that exhibits an XRPD pattern that is substantially the same as that depicted in FIG. 1A or FIG. 1C by volume of the composition. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution.

In some embodiments, the composition comprises about 0.5% of a compound of the invention or phentolamine mesylate that exhibits an XRPD pattern that is substantially the same as that depicted in FIG. 1A or FIG. 1C by weight of the composition. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition comprises about 0.5% of a compound of the invention or phentolamine mesylate that exhibits an XRPD pattern that is substantially the same as that depicted in FIG. 1A or FIG. 1C by volume of the composition. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution.

In some embodiments, the composition is an ophthalmic solution in which a compound of the invention or phentolamine that exhibits an XRPD pattern that is substantially the same as that depicted in FIG. 1A or FIG. 1C is dissolved in an amount of about 0.5% to about 2% by weight of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount that is molar equivalent to about 0.5% to about 5% of phentolamine mesylate by weight or volume of the ophthalmic solution. In some same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount that is molar equivalent to about 0.35% or about 1% of phentolamine mesylate by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount that is molar equivalent to about 0.37% or about 0.5% of phentolamine mesylate by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount of about 0.35% or about 0.75% by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount of about 0.75% by weight or volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine that exhibits an XRPD pattern that is substantially the same as that depicted in FIG. 1A or FIG. 1C is dissolved in an amount of about 0.75% by weight the ophthalmic solution. In some same as that depicted in FIG. 1A. In some embodiments, the phentolamine mesylate exhibits an XRPD pattern that is substantially the same as that depicted in FIG. 1C. In some embodiments, the composition is an ophthalmic solution in which a compound of the invention or phentolamine mesylate that exhibits an XRPD pattern that is substantially the same as that depicted in FIG. 1A or FIG. 1C is dissolved in an amount of about 0.75% by volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, the composition is an ophthalmic solution in which about 1% of a compound of the invention or phentolamine mesylate that exhibits an XRPD pattern that is substantially the same as that depicted in FIG. 1A or FIG. 1C is dissolved by weight of the composition. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the composition is an ophthalmic solution in which about 1% of a compound of the invention or phentolamine mesylate that exhibits an XRPD pattern that is substantially the same as that depicted in FIG. 1A or FIG. 1C by volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, the composition is an ophthalmic solution in which about 0.5% of a compound of the invention or phentolamine mesylate that exhibits an XRPD pattern that is substantially the same as that depicted in FIG. 1A or FIG. 1C is dissolved by weight of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

In some embodiments, the composition is an ophthalmic solution in which about 0.5% of a compound of the invention or phentolamine mesylate that exhibits an XRPD pattern that is substantially the same as that depicted in FIG. 1A or FIG. 1C is dissolved by volume of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

The present invention further provides methods for making an ophthalmic solution, comprising dissolving in a pharmaceutically acceptable aqueous carrier or vehicle: a compound of the invention; phentolamine mesylate that exhibits an XRPD pattern that is substantially the same as that depicted in FIG. 1A or FIG. 1C; phentolamine mesylate that exhibits an XRPD pattern comprising a peak at 8.4±0.2 degrees 2-theta and a peak at 16.3±0.2 degrees 2-theta; phentolamine mesylate that exhibits an XRPD pattern that is substantially the same as that depicted in FIG. 2A; phentolamine mesylate that exhibits an XRPD pattern comprising a Table 3 peak having a relative peak intensity (%) of greater than 30%; phentolamine mesylate that exhibits an XRPD pattern comprising a peak at 8.3±0.2 degrees 2-theta, a peak at 13.3±0.2 degrees 2-theta and a peak at 19.7±0.2 degrees 2-theta; phentolamine mesylate that exhibits an XRPD pattern that is substantially the same as that depicted in FIG. 3A; or phentolamine mesylate that exhibits an XRPD pattern comprising a Table 4 peak having a relative peak intensity (%) of greater than 30%. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C.

The present invention further provides methods for making an ophthalmic solution, comprising dissolving in a pharmaceutically acceptable aqueous carrier or vehicle phentolamine mesylate that exhibits an XRPD pattern that is substantially the same as that depicted in FIG. 4A, FIG. 5A, FIG. 6A, FIG. 7, FIG. 8, FIG. 9, FIG. 10, FIG. 11, FIG. 12, or FIG. 13.

In some embodiments, the ophthalmic solution is suitable for ocular administration or ophthalmic use. In some embodiments, the ophthalmic solution is suitable for topical, subconjunctival, intravitreal, retrobulbar, intracameral or systemic administration.

In some embodiments, an ophthalmic solution in which a compound of the invention is dissolved comprises water, and the compound of the invention is present in the ophthalmic solution at a concentration of about 1% w/v of the ophthalmic solution. In some embodiments, the ophthalmic solution further comprises mannitol, and the mannitol is present in the ophthalmic solution at a concentration of about 4% w/v of the ophthalmic solution. In some embodiments, the ophthalmic solution further comprises sodium acetate trihydrate, and the sodium acetate trihydrate is present in the ophthalmic solution at a concentration of about 0.041% w/v of the ophthalmic solution. In some embodiments, the ophthalmic solution has a pH ranging from about 4.5 to about 5.3.

In some embodiments, an ophthalmic solution in which phentolamine mesylate that exhibits an XRPD pattern that is substantially the same as that depicted in FIG. 1A or FIG. 1C is dissolved comprises water, and the phentolamine is present in the ophthalmic solution at a concentration of about 1% w/v of the ophthalmic solution. In some embodiments, the phentolamine mesylate exhibits an XRPD pattern that is substantially the same as that depicted in FIG. 1A. In some embodiments, the phentolamine mesylate exhibits an XRPD pattern that is substantially the same as that depicted in FIG. 1C. In some embodiments, the ophthalmic solution further comprises mannitol, and the mannitol is present in the ophthalmic solution at a concentration of about 4% w/v of the ophthalmic solution. In some embodiments, the ophthalmic solution further comprises sodium acetate trihydrate, and the sodium acetate trihydrate is present in the ophthalmic solution at a concentration of about 0.041% w/v of the ophthalmic solution. In some embodiments, the ophthalmic solution has a pH ranging from about 4.5 to about 5.3.

In some embodiments, the pharmaceutically acceptable carrier or vehicle is a stabilizer, binder, filler, diluent, disintegrant, wetting agent, lubricant, glidant, coloring agent, dye-migration inhibitor, sweetening agent, flavoring agent, viscosity modifying agent, pH adjusting agent, buffer, osmotic agent, chelating agent, surfactants, or co-solvent.

In some embodiments, a viscosity modifying agent is polyvinyl alcohol, poloxamers, hyaluronic acid, carbomers, and polysaccharides, that is, cellulose derivatives, gellan gum, or xanthan gum.

In some embodiments, the pharmaceutically acceptable aqueous carrier or vehicle is sterile water, sterile buffer solution, or sterile saline.

In some embodiments, the pharmaceutically acceptable carrier or vehicle comprises or is mannitol or sodium acetate.

In some embodiments, the compositions disclosed herein comprise a preservative. In some embodiments, the preservative is benzalkonium chloride, cetrimide, polyquaternium-1, thimerosal, sodium perborate, stabilized oxychloro complex, stabilized chlorite peroxide, chlorhexidine, chlorobutanol, phenylethanol or methylparaben.

In some embodiments, the compositions disclosed herein do not comprise a preservative. In some embodiments, the compositions are preservative free.

In some embodiments, the compositions disclosed herein are sterile.

In some embodiments, the compositions disclosed herein have a pH in the range of about 4 to about 6. In some embodiments, the compositions of the invention have a pH in the range of about 4.5 to about 5.3. In some embodiments, the compositions have a pH of about 4.5, about 4.6, about 4.7, about 4.8, about 4.9, about 5.0, about 5.1, about 5.2, or about 5.3.

In some embodiments, a compound or composition disclosed herein is contained in a sealed container. In some embodiments, the sealed container further contains an inert gas. In some embodiments, the inert gas is argon or nitrogen.

EXAMPLES

General Procedures:

Unless otherwise noted, XRPD data was collected using a PANanalytical EMPYREAN vs. 8.2 20201404 diffractometer with a Cu-Kα radiation (λ=1.541874 Å) source operating at 45 kV and 40 mA in transmission theta-theta configuration. Samples were scanned from 2° to 40° 2-theta with a step size of 0.013° 2-theta and a time per step of 78.795 sec. Data collection was performed with DATA COLLECTOR vs. 7.1 and processed with Data Viewer vs. 2.1 and Profex 5.2.4 software.

Unless otherwise noted, DSC analyses were performed using a Thermal Analysis (TA) Discovery instrument model DSC 25. The samples, typically weighing 1-3 mg, were heated in a sealed standard Tzero aluminum pan at a heating rate of 10° C./min under a nitrogen glass flow of 50 mL/min. A sealed empty Tzero aluminum pan was used as a reference. Data collection was performed with TRIOS software and processed with TRIOS vs. 5.5 software.

Unless otherwise noted, thermogravimetric analysis (TGA) was conducted in a Thermal Analysis (TA) Discovery instrument model TGA 550 using a nitrogen atmosphere with a gas flow of 60 mL/min and a heating rate of 10° C./min. Approximately 1 to 5 mg of sample was used. Data collection was performed with TRIOS software and processed with TRIOS vs. 5.5 software.

Unless otherwise noted, proton nuclear magnetic resonance (1H NMR) analyses were performed using an Agilent Mercury400 NMR Spectrometer. Between 5-15 mg of the sample were dissolved in 0.5 mL-0-7 mL deuterated DMSO.

Unless otherwise noted, temperature-controlled experiments were performed with a Polar Bear Plus heating and cooling platform from Cambridge Reactor Design.

Reference Example A

FIG. 1A shows an XRPD pattern of Reference A, and Table 1 lists XRPD peaks represented in FIG. 1A. FIG. 1B shows a DSC thermogram of Reference A.

TABLE 1

| XRPD Data for Reference A | | | |
|---|---|---|---|
| 2-theta Angle (°) | d Value (Å) | Height (Counts) | Rel. Intensity (%) |
| 6.9 | 12.8 | 4569.7 | 13.0 |
| 8.5 | 10.4 | 1462.4 | 4.2 |
| 10.1 | 8.7 | 796.6 | 2.3 |
| 11.6 | 7.6 | 13570.5 | 38.5 |

TABLE 1-continued

| XRPD Data for Reference A | | | |
|---|---|---|---|
| 2-theta Angle (°) | d Value (Å) | Height (Counts) | Rel. Intensity (%) |
| 12.6 | 7.0 | 631.6 | 1.8 |
| 14.6 | 6.1 | 1336.8 | 3.8 |
| 14.7 | 6.0 | 1391.1 | 4.0 |
| 15.4 | 5.8 | 3872.7 | 11.0 |
| 16.7 | 5.3 | 3218.9 | 9.1 |
| 16.9 | 5.2 | 526.2 | 1.5 |
| 18.5 | 4.8 | 8810.6 | 25.0 |
| 18.9 | 4.7 | 3519.3 | 10.0 |
| 19.1 | 4.6 | 823.6 | 2.3 |
| 19.4 | 4.6 | 258.0 | 0.7 |
| 20.3 | 4.4 | 35229.3 | 100.0 |
| 20.6 | 4.3 | 442.9 | 1.3 |
| 21.1 | 4.2 | 11928.3 | 33.9 |
| 21.3 | 4.2 | 8730.1 | 24.8 |
| 21.7 | 4.1 | 6250.9 | 17.7 |
| 22.1 | 4.0 | 1805.9 | 5.1 |
| 23.2 | 3.8 | 2572.0 | 7.3 |
| 23.3 | 3.8 | 2066.8 | 5.9 |
| 23.8 | 3.7 | 4070.9 | 11.6 |
| 23.9 | 3.7 | 4369.4 | 12.4 |
| 24.5 | 3.6 | 2569.7 | 7.3 |
| 24.6 | 3.6 | 983.7 | 2.8 |
| 25.4 | 3.5 | 93.0 | 0.3 |
| 26.1 | 3.4 | 1376.5 | 3.9 |
| 26.4 | 3.4 | 384.1 | 1.1 |
| 27.1 | 3.3 | 453.7 | 1.3 |
| 27.6 | 3.2 | 3268.4 | 9.3 |
| 27.9 | 3.2 | 995.8 | 2.8 |
| 28.9 | 3.1 | 899.9 | 2.6 |
| 29.5 | 3.0 | 1543.0 | 4.4 |
| 29.9 | 3.0 | 186.9 | 0.5 |

Reference Example B

Figure 1D:
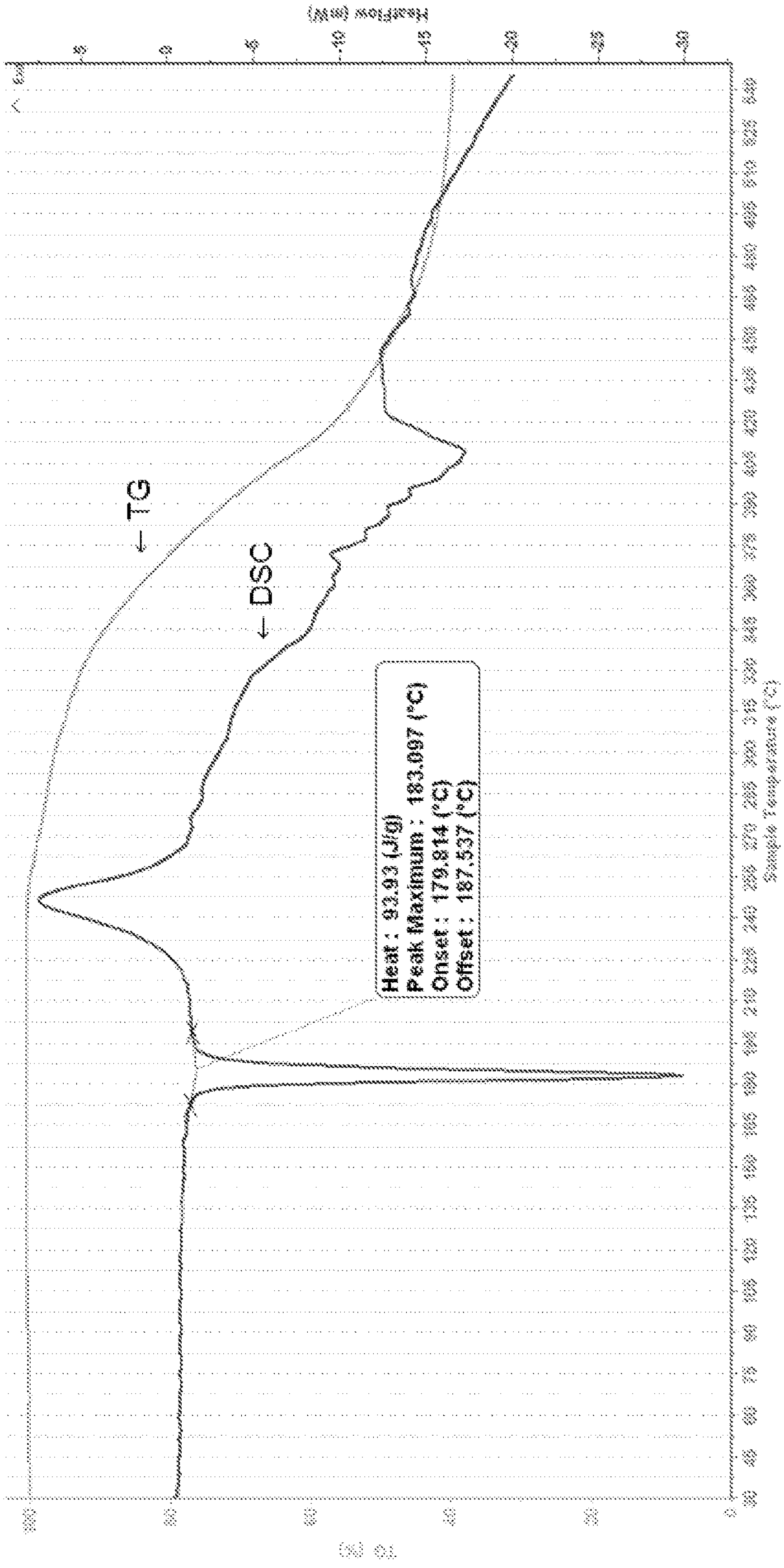
FIG. 1D shows an overlay of a thermogravimetric (TG) thermogram and a DSC thermogram of Reference B.

The XRPD analysis and TG/DSC analysis of Reference B were also performed. FIG. 1C shows an XRPD diffractogram of Reference B, and Table 2 lists XRPD peaks represented in FIG. 1C. FIG. 1D shows an overlay of a TG thermogram of Reference B and a DSC thermogram of Reference B with one endothermic event (peak maximum at about 183° C.) and one exothermic event.

XRPD analysis for FIG. 1C and Table 2 was carried out using a Bruker D8 Discover diffractometer with DAVINCI configuration, in transmission mode (scan type: TwoTheta or Offset Coupled TwoTheta/Theta) scanning about 5 mg of Reference B at between 1.5 and 45° 2θ angles, and using the following measurements characteristics: acquisition time was 53 minutes, increment per step was 0.01°, time per step was 0.7 s, and generator voltage/generator amperage was 40 mA/40 kV to reach 1.6 kW power. The raw data was imported in the Diffrac. EVA5.0 software and it was processed using the subsequent parameters: background subtraction and Kα2 stripping were performed before peak determination, and the peak search operation was performed with a threshold of 1 and a peak width of 0.153 for the sample. Only the resulting peaks having relative intensity of greater than 2% were considered. The degree of crystallinity was calculated using the Diffrac.EVA5.0 software option. The degree of crystallinity of Reference B was 85.1% with 14.9% amorphous phase.

TABLE 2

| XRPD Data for Reference B | | |
|---|---|---|
| Angle 2θ (°) | Net Intensity (counts) | Rel. Intensity (%) |
| 6.67 | 287.05 | 6.10 |
| 6.92 | 656.31 | 13.95 |
| 8.26 | 113.50 | 2.41 |
| 8.57 | 380.56 | 8.09 |
| 10.17 | 128.57 | 2.73 |
| 11.22 | 258.56 | 5.50 |
| 11.71 | 1718.23 | 36.53 |
| 14.73 | 328.32 | 6.98 |
| 15.44 | 662.52 | 14.09 |
| 16.76 | 797.82 | 16.96 |
| 16.94 | 125.17 | 2.66 |
| 17.80 | 127.99 | 2.72 |
| 18.14 | 149.55 | 3.18 |
| 18.59 | 1108.99 | 23.58 |
| 18.94 | 1423.19 | 30.26 |
| 19.22 | 267.97 | 5.70 |
| 19.54 | 577.37 | 12.28 |
| 20.40 | 4703.14 | 100.00 |
| 20.66 | 373.47 | 7.94 |
| 21.15 | 1970.68 | 41.90 |
| 21.42 | 3983.23 | 84.69 |
| 21.76 | 877.82 | 18.66 |
| 22.14 | 575.15 | 12.23 |
| 22.33 | 148.16 | 3.15 |
| 22.91 | 124.08 | 2.64 |
| 23.33 | 750.03 | 15.95 |
| 23.93 | 1355.51 | 28.82 |
| 24.58 | 488.33 | 10.38 |
| 24.70 | 303.72 | 6.46 |
| 26.15 | 225.95 | 4.80 |
| 26.53 | 163.51 | 3.48 |
| 27.19 | 185.76 | 3.95 |
| 27.69 | 797.21 | 16.95 |
| 27.99 | 224.00 | 4.76 |
| 29.07 | 126.74 | 2.69 |
| 29.57 | 195.09 | 4.15 |
| 31.27 | 167.71 | 3.57 |
| 31.99 | 228.62 | 4.86 |
| 32.39 | 331.96 | 7.06 |
| 32.64 | 259.17 | 5.51 |
| 33.23 | 140.20 | 2.98 |
| 33.41 | 210.77 | 4.48 |
| 34.31 | 97.99 | 2.08 |
| 37.97 | 102.05 | 2.17 |
| 38.53 | 94.74 | 2.01 |
| 40.43 | 196.96 | 4.19 |

Example 1

Procedure A: Phentolamine mesylate (3.45 g, 1 equiv.) prepared according to Example 2 of U.S. Pat. No. 11,566,005 was added to a 100 mL reaction vessel having a torispherical bottom and equipped mechanical stirring. The reaction vessel was charged with acetone (37 mL), water (3.2 mL), and methane sulfonic acid (0.055 ml, 0.1 equiv.) and allowed to stir at 25° C. for 0.5 h. The resultant reaction mixture was a purple suspension. The reaction vessel was heated to 45° C. and allowed to stir for 0.5 h at 45° C. The reaction mixture became a solution. The reaction vessel was cooled to 25° C. over 20 minutes. The reaction mixture remained a solution. t-Butyl methyl ether (TBME, 34.5 mL) was added to the reaction vessel, and a white solid precipitated. The reaction vessel was cooled to 0° C. at 1.33° C./min and dark droplets were observed. The reaction mixture was stirred for 1 h at 0° C. The reaction vessel was further cooled to −20° C. at 1° C./min then allowed to stir for 3 hours at −20° C.

The reaction mixture was filtered under vacuum, and the resultant filter cake, off-white solid with light purple tinge, was washed with TBME (2×10 mL) and air dried under vacuum. The resultant solid was further dried in in a rotary evaporator at 40° C. for 48 h. The further dried phentolamine mesylate was analyzed by XRPD and DSC.

FIG. 2A shows an XRPD diffractogram of the phentolamine mesylate obtained according to this Example 1, and Table 3 lists XRPD peaks represented in FIG. 2A.

TABLE 3

| XRPD Data for Phentolamine Mesylate from this Example 1 | | | |
|---|---|---|---|
| 2-theta Angle (°) | d Value (Å) | Height (Counts) | Rel. Intensity (%) |
| 8.4 | 10.5 | 13087.5 | 54.7 |
| 8.9 | 9.9 | 7267.0 | 30.4 |
| 10.3 | 8.6 | 734.9 | 3.1 |
| 10.9 | 8.1 | 1534.1 | 6.4 |
| 11.1 | 7.9 | 2538.4 | 10.6 |
| 11.5 | 7.7 | 3563.9 | 14.9 |
| 13.1 | 6.7 | 23928.7 | 100.0 |
| 15.8 | 5.6 | 1622.0 | 6.8 |
| 16.3 | 5.4 | 5164.0 | 21.6 |
| 16.9 | 5.3 | 8619.7 | 36.0 |
| 18.4 | 4.8 | 9063.7 | 37.9 |
| 18.8 | 4.7 | 14551.2 | 60.8 |
| 19.2 | 4.6 | 5768.1 | 24.1 |
| 19.4 | 4.6 | 17489.2 | 73.1 |
| 20.0 | 4.4 | 14398.7 | 60.2 |
| 20.5 | 4.3 | 4527.6 | 18.9 |
| 20.8 | 4.3 | 19619.5 | 82.0 |
| 21.1 | 4.2 | 1468.2 | 6.1 |
| 21.3 | 4.2 | 1041.1 | 4.4 |
| 21.5 | 4.1 | 1356.4 | 5.7 |
| 21.9 | 4.0 | 2909.9 | 12.2 |
| 22.2 | 4.0 | 7680.3 | 32.1 |
| 22.9 | 3.9 | 1817.8 | 7.6 |
| 23.2 | 3.8 | 2789.5 | 11.7 |
| 23.5 | 3.8 | 2324.4 | 9.7 |
| 24.0 | 3.7 | 4321.5 | 18.1 |
| 24.3 | 3.7 | 2614.2 | 10.9 |
| 24.9 | 3.6 | 329.8 | 1.4 |
| 25.4 | 3.5 | 3062.8 | 12.8 |
| 26.3 | 3.4 | 2586.7 | 10.8 |
| 27.0 | 3.3 | 4128.9 | 17.3 |
| 27.4 | 3.3 | 2272.9 | 9.5 |
| 28.3 | 3.2 | 484.2 | 2.0 |
| 28.5 | 3.1 | 2800.0 | 11.7 |
| 28.7 | 3.1 | 1827.4 | 7.6 |
| 29.3 | 3.0 | 1772.2 | 7.4 |
| 30.4 | 2.9 | 2102.5 | 8.8 |
| 31.2 | 2.9 | 709.6 | 3.0 |
| 31.5 | 2.8 | 1127.5 | 4.7 |
| 31.9 | 2.8 | 1198.1 | 5.0 |
| 32.1 | 2.8 | 1592.9 | 6.7 |
| 35.1 | 2.6 | 2940.6 | 12.3 |
| 36.3 | 2.5 | 1266.5 | 5.3 |

The DSC analysis of the phentolamine mesylate obtained according to this Example 1 showed two large endothermic events: a first event which onset at about 113° C. (peak maximum at about 120° C.) and a second event which onset at about 130° C. (peak maximum at about 133° C.) (FIG. 2B). The DSC analysis also showed one small endothermic event which onset at about 179° C. (peak maximum at about 180° C.).

Procedure B: Phentolamine mesylate (20 mg) prepared according to Example 2 of U.S. Pat. No. 11,566,005 was suspended in dichloromethane (800 μL). The suspension was subjected to heat-cool cycles between 25° C. and 50° C. (2 h at each temperature, with heating and cooling ramps of 1° C./min) for about 3 days. The resultant reaction mixture was centrifuged at 4000 rpm at 25° C. for 10-15 minutes and the resultant supernatant was decanted. The residual solid was dried under vacuum at 25° C. for 16 h to provide an off-white/pink solid. The solid's XRPD pattern was consistent with the XRPD pattern depicted in FIG. 2A.

Procedure C: Phentolamine mesylate (963 mg) prepared according to Example 2 of U.S. Pat. No. 11,566,005 was dissolved in methyl ethyl ketone (MEK):water 96:4 w/w (6 ml) at 80° C. The solution was cooled to 45° C. at 0.5° C./min. Seeds of phentolamine mesylate obtained according to Procedure B of this Example 1 were added (approximately 2 mg) and the resultant mixture was cooled further to 10° C. and allowed to stir for 30 minutes. The resulting suspension was heated to 35° C. and vacuum was applied to remove approximately ⅓ of the volume. Then, the vacuum was removed and the suspension was cooled to 10° C. and allowed to stir for 40 minutes. The resultant solid was isolated by vacuum filtration, washed with cold MEK (0.5 ml) and dried for 16 h under vacuum at about 0.24 bar at ambient temperature to provide an off-white/pink solid (677 mg). The solid's XRPD pattern was consistent with the XRPD pattern depicted in FIG. 2A.

Procedure D: Phentolamine mesylate (93.4 mg) prepared according to Example 2 of U.S. Pat. No. 11,566,005 was suspended in MEK:water 96:4 w:w (497 mg) at room temperature. The mixture was subjected to three heat-cool cycles between 10° C. and 77° C. using heating and cooling rates of 0.5° C./min (with no holding time at 10° C. or 77° C.). At the end of the third cycle, the temperature was held at 10° C. for about 7 hours. The resultant solid was isolated by filtration to provide an off-white/pink solid. The solid's XRPD pattern was consistent with the XRPD pattern depicted in FIG. 2A.

Example 2

Phentolamine mesylate (12.7 mg) obtained according to Example 1 above was heated to 126° C. at 10° C./min and was allowed to cool to room temperature. The resultant phentolamine mesylate was analyzed by XRPD and DSC.

FIG. 3A shows an XRPD diffractogram of the phentolamine mesylate obtained by this Example 2, and Table 4 lists XRPD peaks represented in FIG. 3A. The XRPD diffractogram's peak at 6.9 degrees 2-theta and peak at 11.6 degrees 2-theta indicate a presence of a small amount of phentolamine mesylate having XRPD peaks of Reference A.

TABLE 4

XRPD Data for Phentolamine Mesylate Obtained According to this Example 2

| 2-theta Angle (°) | d Value (Å) | Height (Counts) | Rel. Intensity (%) |
|---|---|---|---|
| 6.9 | 12.9 | 1140.7 | 9.9 |
| 8.3 | 10.6 | 11494.5 | 100.0 |
| 9.0 | 9.8 | 1139.3 | 9.9 |
| 10.3 | 8.6 | 334.1 | 2.9 |
| 11.3 | 7.8 | 1462.3 | 12.7 |
| 11.6 | 7.6 | 545.7 | 4.8 |
| 13.3 | 6.7 | 8206.1 | 71.4 |
| 13.8 | 6.4 | 276.2 | 2.4 |
| 14.7 | 6.0 | 353.2 | 3.1 |
| 15.4 | 5.8 | 243.4 | 2.1 |
| 15.7 | 5.6 | 1166.8 | 10.2 |
| 16.7 | 5.3 | 6842.4 | 59.5 |
| 17.1 | 5.2 | 644.3 | 5.6 |
| 18.5 | 4.8 | 739.8 | 6.4 |
| 18.8 | 4.7 | 4347.5 | 37.8 |
| 18.9 | 4.7 | 5387.5 | 46.9 |
| 19.1 | 4.6 | 1570.0 | 13.7 |
| 19.4 | 4.6 | 1421.0 | 12.4 |
| 19.7 | 4.5 | 6097.0 | 53.0 |
| 20.3 | 4.4 | 6631.7 | 57.7 |
| 21.0 | 4.2 | 2408.3 | 21.0 |
| 21.4 | 4.2 | 1303.7 | 11.3 |

TABLE 4-continued

XRPD Data for Phentolamine Mesylate Obtained According to this Example 2

| 2-theta Angle (°) | d Value (Å) | Height (Counts) | Rel. Intensity (%) |
|---|---|---|---|
| 22.0 | 4.0 | 2075.0 | 18.1 |
| 22.5 | 3.9 | 1615.1 | 14.1 |
| 23.0 | 3.9 | 877.9 | 7.6 |
| 23.5 | 3.8 | 1890.5 | 16.5 |
| 24.7 | 3.6 | 411.1 | 3.6 |
| 25.2 | 3.5 | 768.2 | 6.7 |
| 25.4 | 3.5 | 1037.7 | 9.0 |
| 25.9 | 3.4 | 491.2 | 4.3 |
| 27.3 | 3.3 | 1502.4 | 13.1 |
| 29.9 | 3.0 | 471.4 | 4.1 |
| 30.4 | 2.9 | 525.7 | 4.6 |

DSC analysis of the phentolamine mesylate obtained according to this Example 2 showed a small endothermic event having an onset at about 129° C. (peak maximum at about 133° C.) and a small exothermic event having an onset at about 135° C. (peak maximum at about 138° C.) (FIG. 3B). The DSC analysis also showed a sharp endothermic event having an onset at about 178° C. (peak maximum at about 180° C.).

Example 3

A suspension of Reference A (20 mg) in acetone (50 μL) was subjected to heat-cool cycles between 25° C. and 50° C. (2 h at each temperature, with heating and cooling ramps of 1° C./min) for up to three days. The resultant reaction mixture was centrifuged at 4000 rpm at 25° C. for 10-15 minutes, and the resultant supernatant was decanted. The residual solid was taken with a spatula and analyzed wet by XRPD.

FIG. 4A shows an XRPD diffractogram of the phentolamine mesylate obtained according to this Example 3, and Table 5 below lists XRPD peaks represented in FIG. 4A.

TABLE 5

XRPD Data for Phentolamine Mesylate Obtained According to Example 3

| 2-theta Angle (°) | d Value (Å) | Height (Counts) | Rel. Intensity (%) |
|---|---|---|---|
| 7.1 | 12.4 | 4741.1 | 54.3 |
| 8.9 | 10.0 | 2153.4 | 24.7 |
| 10.9 | 8.1 | 331.2 | 3.8 |
| 11.8 | 7.5 | 388.3 | 4.5 |
| 13.0 | 6.8 | 3116.0 | 35.7 |
| 14.3 | 6.2 | 740.7 | 8.5 |
| 14.7 | 6.0 | 626.7 | 7.2 |
| 15.1 | 5.9 | 954.4 | 10.9 |
| 16.2 | 5.5 | 598.4 | 6.9 |
| 16.5 | 5.4 | 628.2 | 7.2 |
| 17.1 | 5.2 | 489.1 | 5.6 |
| 17.8 | 5.0 | 1450.0 | 16.6 |
| 19.0 | 4.7 | 2307.1 | 26.4 |
| 19.9 | 4.5 | 8733.6 | 100.0 |
| 20.2 | 4.4 | 1626.0 | 18.6 |
| 20.4 | 4.4 | 765.2 | 8.8 |
| 21.0 | 4.2 | 1854.5 | 21.2 |
| 21.4 | 4.1 | 743.3 | 8.5 |
| 21.9 | 4.1 | 2216.7 | 25.4 |
| 22.4 | 4.0 | 451.8 | 5.2 |
| 22.6 | 3.9 | 978.2 | 11.2 |
| 23.5 | 3.8 | 849.1 | 9.7 |
| 24.3 | 3.7 | 740.1 | 8.5 |
| 24.5 | 3.6 | 257.3 | 3.0 |
| 25.2 | 3.5 | 168.2 | 1.9 |
| 25.6 | 3.5 | 659.6 | 7.6 |

TABLE 5-continued

XRPD Data for Phentolamine Mesylate Obtained According to Example 3

| 2-theta Angle (°) | d Value (Å) | Height (Counts) | Rel. Intensity (%) |
|---|---|---|---|
| 26.1 | 3.4 | 400.5 | 4.6 |
| 26.3 | 3.4 | 443.1 | 5.1 |
| 26.9 | 3.3 | 387.2 | 4.4 |
| 27.3 | 3.3 | 324.6 | 3.7 |
| 28.4 | 3.1 | 145.9 | 1.7 |
| 29.2 | 3.1 | 871.2 | 10.0 |
| 30.7 | 2.9 | 305.5 | 3.5 |
| 32.0 | 2.8 | 218.6 | 2.5 |
| 33.1 | 2.7 | 180.7 | 2.1 |
| 33.9 | 2.6 | 442.3 | 5.1 |
| 34.4 | 2.6 | 339.1 | 3.9 |
| 35.0 | 2.6 | 142.9 | 1.6 |
| 36.6 | 2.5 | 201.5 | 2.3 |

DSC analysis of the phentolamine mesylate obtained according to this Example 3 showed two endothermic events: a first event having an onset at about 99° C. (peak maximum at about 100° C.) and a second event having an onset at about 179° C. (peak maximum at about 181° C.) (FIG. 4B).

A mass loss of about 7% was observed on the TG curve, corresponding to the first endothermic event (FIG. 4C).

A $^1$H-NMR spectrum of the phentolamine mesylate obtained according to this Example 3 was obtained (FIG. 4D).

Based on the TG/DSC and $^1$H-NMR data, the phentolamine mesylate obtained according to this Example 3 is an acetone solvate.

Example 4

Reference A (50 mg) was suspended in MeCN (500 μl) and slurried at 5° C. for 1 week. The resultant solid was isolated after 1 week by vacuum filtration at 0.24 bar at 25° C. and analyzed by XRPD.

FIG. 5A shows an XRPD diffractogram of the phentolamine mesylate obtained according to this Example 4. DSC analysis of the phentolamine mesylate obtained according to this Example 4 showed multiple events (FIG. 5B): a broad endothermic event having an onset at about 41° C. (peak maximum at about 52° C.); a broad endothermic event having an onset at about 91° C. (peak maximum at about 99° C.); an endothermic event having an onset at about 110° C. (peak maximum at about 114° C.); an exothermic event having an onset at about 129° C. (peak maximum at about 133° C.); and a sharp endothermic event having an onset at about 178° C. (peak maximum at about 180° C.).

A mass loss of about 3% and a mass loss of about 5% was observed according to the TG curve (FIG. 5C).

The phentolamine mesylate obtained according to this Example 4 was further dried at 0.24 bar and 25° C. for 16 hours. The XRPD analysis of the further dried material indicated that the phentolamine mesylate form exhibiting XRPD pattern of FIG. 5A, upon further drying, converted to a mixture of the phentolamine mesylate having XRPD peaks of Reference A and the phentolamine mesylate obtained according to Example 1.

Example 5

Reference A (20 mg) was placed in a 2 mL HPLC vial equipped with 3 stainless steel 3 mm diameter balls. 1,4-Dioxane (20 μL) was added to the vial at room temperature and the phentolamine mesylate/1,4-dioxane mixture was ground using a Fritsch Pulverisette planetary mill at 400 rpm for 3 h. The resultant solid was dried under vacuum at 0.24 bar for 16 h and analyzed by XRPD.

FIG. 6A shows an XRPD diffractogram of the phentolamine mesylate obtained according to this Example 5, and Table 6 below lists XRPD peaks represented in FIG. 6A.

TABLE 6

XRPD Data for Phentolamine Mesylate Obtained According to Example 5

| 2-theta Angle (°) | d Value (Å) | Height (Counts) | Rel. Intensity (%) |
|---|---|---|---|
| 7.4 | 12.0 | 16829.9 | 40.1 |
| 9.2 | 9.6 | 7349.4 | 17.5 |
| 10.8 | 8.2 | 5357.7 | 12.8 |
| 11.3 | 7.8 | 577.3 | 1.4 |
| 12.7 | 7.0 | 1174.1 | 2.8 |
| 13.1 | 6.8 | 14276.7 | 34.0 |
| 14.7 | 6.0 | 6144.0 | 14.6 |
| 14.8 | 6.0 | 3609.2 | 8.6 |
| 15.8 | 5.6 | 5730.2 | 13.7 |
| 16.1 | 5.5 | 1909.1 | 4.6 |
| 16.6 | 5.3 | 782.1 | 1.9 |
| 17.5 | 5.1 | 1751.3 | 4.2 |
| 18.4 | 4.8 | 11291.1 | 26.9 |
| 18.7 | 4.7 | 4141.9 | 9.9 |
| 19.5 | 4.6 | 6051.5 | 14.4 |
| 19.8 | 4.5 | 41962.1 | 100.0 |
| 20.2 | 4.4 | 1880.3 | 4.5 |
| 20.7 | 4.3 | 14457.0 | 34.5 |
| 20.9 | 4.3 | 33417.6 | 79.6 |
| 21.2 | 4.2 | 3378.1 | 8.1 |
| 21.7 | 4.1 | 2336.7 | 5.6 |
| 21.9 | 4.1 | 3102.7 | 7.4 |
| 22.2 | 4.0 | 2030.7 | 4.8 |
| 22.7 | 3.9 | 4311.6 | 10.3 |
| 23.0 | 3.9 | 1937.4 | 4.6 |
| 23.3 | 3.8 | 2502.8 | 6.0 |
| 24.2 | 3.7 | 804.3 | 1.9 |
| 24.6 | 3.6 | 3357.1 | 8.0 |
| 24.9 | 3.6 | 377.2 | 0.9 |
| 25.4 | 3.5 | 518.7 | 1.2 |
| 25.8 | 3.5 | 2029.5 | 4.8 |
| 26.3 | 3.4 | 1766.4 | 4.2 |
| 26.6 | 3.4 | 1271.4 | 3.0 |
| 26.8 | 3.3 | 1551.2 | 3.7 |
| 27.2 | 3.3 | 2051.6 | 4.9 |
| 27.4 | 3.3 | 1193.4 | 2.8 |
| 27.6 | 3.2 | 548.3 | 1.3 |
| 28.8 | 3.1 | 2364.3 | 5.6 |
| 28.9 | 3.1 | 2656.7 | 6.3 |
| 29.1 | 3.1 | 1499.2 | 3.6 |
| 29.4 | 3.0 | 770.9 | 1.8 |
| 29.8 | 3.0 | 1082.0 | 2.6 |
| 30.3 | 2.9 | 2090.0 | 5.0 |
| 30.6 | 2.9 | 1585.7 | 3.8 |

DSC analysis of the phentolamine mesylate obtained according to this Example 5 showed one endothermic event having an onset at about 140° C. (peak maximum at about 143° C.) (FIG. 6B).

A mass loss of about 9.5% was observed according to the TG curve, corresponding to the endothermic event (FIG. 6C).

A $^1$H-NMR spectrum of the phentolamine mesylate obtained according to this Example 5 was obtained (FIG. 6D).

Based on the TG/DSC and $^1$H-NMR data, the phentolamine mesylate obtained according to this Example 5 is a 1,4-dioxane solvate.

Example 6

Reference A (20 mg) was suspended in THF (100 μl) and slurried at 40° C. for 24 h. The resultant solid was centrifuged at 4000 rpm at 25° C. for 10-15 minutes, and the resultant supernatant was decanted. The residual solid was taken with a spatula and analyzed wet by XRPD.

FIG. 7 shows an XRPD diffractogram of the phentolamine mesylate obtained according to this Example 6.

The phentolamine mesylate obtained according to this Example 6 was further dried at 25° C. at 0.24 bar for 16 hours. The XRPD analysis of the further dried material indicated that the phentolamine mesylate form exhibiting XRPD pattern of FIG. 7, upon further drying, converted to the phentolamine mesylate obtained according to Example 1.

Example 7

Reference A (50 mg) was suspended in THF (500 μl) and slurried at 25° C. for 1 week. The resultant solid was centrifuged at 4000 rpm at 25° C. for 10-15 minutes, and the supernatant was decanted. The solid was analyzed wet by XRPD.

FIG. 8 shows an overlay of XRPD pattern of the phentolamine mesylate obtained according to this Example 7 (top) with an XRPD pattern of the phentolamine mesylate obtained according to Example 6 (bottom). FIG. 8 indicates that the phentolamine mesylate obtained according to this Example 7 is a mixture that includes the phentolamine mesylate obtained according to Example 6.

The phentolamine mesylate obtained according to this Example 7 was further dried at 0.24 bars at 25° C. for 16 hours. The XRPD analysis of the further dried material indicated that the mixture converted to the phentolamine mesylate obtained according to Example 1 above.

Example 8

Reference A (20 mg) was dissolved in 2 vol of MeOH. Aliquots of isobutyl acetate (100 μL) were added until a suspension was obtained. The resultant solid was centrifuged at 4000 rpm at 25° C. for 10-15 minutes, and the supernatant was decanted. The residual wet solid was taken with a spatula and analyzed wet by XRPD.

FIG. 9 shows an XRPD diffractogram of the phentolamine mesylate obtained according to this Example 8.

Example 9

Reference A (20 mg) was placed in an open, uncapped 2 mL HPLC vial, which was subsequently placed into a 20 mL vial containing 1 mL of dichloromethane. The 20 mL vial was capped and stored at room temperature for 2 weeks while the Reference A in the smaller vial was exposed to dichloromethane vapor. The resultant solid was collected and analyzed wet by XRPD.

FIG. 10 shows an overlay of an XRPD pattern of the phentolamine mesylate obtained according to this Example 9 (bottom) with an XRPD pattern of the phentolamine mesylate obtained according to Example 1 above (top). FIG. 10 indicates that the phentolamine mesylate obtained according to this Example 9 is a mixture that includes the phentolamine mesylate obtained according to Example 1 above.

Example 10

Reference A (20 mg) was placed into an open, uncapped 2 mL HPLC vial, which was subsequently placed into a 20 mL vial containing 1 mL of chloroform. The 20 mL vial was capped and stored at room temperature for 2 weeks while the Reference A in the smaller vial was exposed to chloroform vapor. The resultant solid was collected and analyzed wet by XRPD.

FIG. 11 shows an XRPD diffractogram of the phentolamine mesylate obtained according to this Example 10.

Example 11

Reference A (20 mg) was dissolved in 2 vol of MeOH. Aliquots of ethyl acetate (100 μL) were added until a suspension was obtained. The resultant solid was centrifuged at 4000 rpm at 25° C. for 10-15 minutes, and the resultant supernatant was decanted. The residual solid was taken with a spatula and analyzed wet by XRPD.

FIG. 12 shows an XRPD diffractogram of the phentolamine mesylate obtained according to this Example 11.

The phentolamine mesylate obtained according to this Example 11 was further dried at 25° C. and 0.24 bar for 16 hours. The XRPD analysis of the further dried material indicated that the phentolamine mesylate obtained according to this Example 11 converted to the phentolamine mesylate obtained according to Example 1 above.

Example 12

Reference A (20 mg) was dissolved in 2 vol of DMSO. Aliquots of methyl ethyl ketone (100 μL) were added until a suspension was obtained. The resultant solid was centrifuged at 4000 rpm at 25° C. for 10-15 minutes, and the resultant supernatant was decanted. The residual solid was taken with a spatula and analyzed wet by XRPD.

FIG. 13 shows an XRPD diffractogram of the phentolamine mesylate obtained according to this Example 12.

The phentolamine mesylate obtained according to this Example 12 was further dried at 25° C. and 0.24 bar for 16 hours. The XRPD analysis of the further dried material indicated that the phentolamine mesylate obtained according to this Example 12 converted to the phentolamine mesylate obtained according to Example 1 above.

What is claimed is:

1. Phentolamine mesylate that exhibits an X-ray powder diffraction (XRPD) pattern comprising a peak at 8.4±0.2 degrees 2-theta, a peak at 13.1±0.2 degrees 2-theta, a peak at 16.3±0.2 degrees 2-theta, a peak at 19.4±0.2 degrees 2-theta, and a peak at 20.8±0.2 degrees 2-theta.

2. The phentolamine mesylate of claim 1, wherein the XRPD pattern further comprises a peak at 8.9±0.2 degrees 2-theta, a peak at 10.3±0.2 degrees 2-theta, a peak at 10.9±0.2 degrees 2-theta, a peak at 11.1±0.2 degrees 2-theta, a peak at 16.9±0.2 degrees 2-theta, a peak at 18.4±0.2 degrees 2-theta, a peak at 18.8±0.2 degrees 2-theta, a peak at 19.2±0.2 degrees 2-theta, a peak at 20.0±0.2 degrees 2-theta, or a peak at 22.2=0.2 degrees 2-theta.

3. Phentolamine mesylate that exhibits an XRPD pattern that is substantially the same as that depicted in FIG. 2A.

4. A composition comprising a pharmaceutically acceptable aqueous carrier or vehicle in which the phentolamine mesylate of claim 1 is dissolved.

5. A method for treating or reversing pharmacologically induced mydriasis, comprising administering to a subject in need thereof an effective amount of or the composition of claim 4.

6. The method of claim 5, wherein the pharmacologically induced mydriasis is produced by an adrenergic agonist or a parasympatholytic agent.

7. A method for treating or preventing an ocular disease or condition, comprising administering to a subject in need thereof an effective amount of claim 4.

8. The method of claim 7, wherein the ocular disease or condition is a dim or night vision disturbance.

9. The method of claim 7, wherein the ocular disease or condition is presbyopia.

10. A method for treating or reversing pharmacologically induced mydriasis, comprising dissolving the phentolamine mesylate of claim 1 in a pharmaceutically acceptable aqueous carrier or vehicle to provide an ophthalmic solution and administering to a subject in need of treatment or reversal of pharmacologically induced mydriasis an effective amount of the ophthalmic solution.

11. The method of claim 10, wherein the pharmacologically induced mydriasis is produced by an adrenergic agonist or a parasympatholytic agent.

12. A method for making the phentolamine mesylate of claim 1, comprising:

(a) heating a mixture comprising (i) phentolamine mesylate that exhibits an XRPD pattern comprising a peak at 6.87±0.2 degrees 2-theta, a peak at 11.65±0.2 degrees 2-theta, a peak at 13.15±0.2 degrees 2-theta, a peak at 18.86±0.2 degrees 2-theta, a peak at 20.32±0.2 degrees 2-theta, a peak at 20.85±0.2 degrees 2-theta, a peak at 21.07±0.2 degrees 2-theta, and a peak at 21.36±0.2 degrees 2-theta and (ii) dichloromethane at about 50° C. for about two hours to provide a heated mixture;

(b) allowing the heated mixture to cool at about 25° C. for about two hours to provide cooled phentolamine mesylate; and (c) repeating steps (a) and (b) for up to about three days to provide the phentolamine mesylate of claim 1.

13. The method of claim 12 further comprising:

(d) isolating the phentolamine mesylate of claim 1.

14. A composition comprising a pharmaceutically acceptable aqueous carrier or vehicle in which the phentolamine mesylate of claim 2 is dissolved.

15. A composition comprising a pharmaceutically acceptable aqueous carrier or vehicle in which the phentolamine mesylate of claim 3 is dissolved.

16. A method for treating or reversing pharmacologically induced mydriasis, comprising administering to a subject in need thereof an effective amount of the composition of claim 14.

17. The method of claim 16, wherein the pharmacologically induced mydriasis is produced by an adrenergic agonist or a parasympatholytic agent.

18. A method for treating or reversing pharmacologically induced mydriasis, comprising administering to a subject in need thereof an effective amount of the composition of claim 15.

19. The method of claim 18, wherein the pharmacologically induced mydriasis is produced by an adrenergic agonist or a parasympatholytic agent.

20. A method for treating or preventing an ocular disease or condition, comprising administering to a subject in need thereof an effective amount of the composition of claim 14.

21. The method of claim 20, wherein the ocular disease or condition is a dim or night vision disturbance.

22. The method of claim 20, wherein the ocular disease or condition is presbyopia.

23. A method for treating or preventing an ocular disease or condition, comprising administering to a subject in need thereof an effective amount of the composition of claim 15.

24. The method of claim 23, wherein the ocular disease or condition is a dim or night vision disturbance.

25. The method of claim 23, wherein the ocular disease or condition is presbyopia.

26. A method for treating or reversing pharmacologically induced mydriasis, comprising dissolving the phentolamine mesylate of claim 2 in a pharmaceutically acceptable aqueous carrier or vehicle to provide an ophthalmic solution and administering to a subject in need of treatment or reversal of pharmacologically induced mydriasis an effective amount of the ophthalmic solution.

27. The method of claim 26, wherein the pharmacologically induced mydriasis is produced by an adrenergic agonist or a parasympatholytic agent.

28. A method for treating or reversing pharmacologically induced mydriasis, comprising dissolving the phentolamine mesylate of claim 3 in a pharmaceutically acceptable aqueous carrier or vehicle to provide an ophthalmic solution and administering to a subject in need of treatment or reversal of pharmacologically induced mydriasis an effective amount of the ophthalmic solution.

29. The method of claim 28, wherein the pharmacologically induced mydriasis is produced by an adrenergic agonist or a parasympatholytic agent.

30. A method for treating or preventing an ocular disease or condition, comprising dissolving the phentolamine mesylate of claim 1 in a pharmaceutically acceptable aqueous carrier or vehicle to provide an ophthalmic solution and administering to a subject in need thereof an effective amount of the ophthalmic solution.

31. The method of claim 30, wherein the ocular disease or condition is a dim or night vision disturbance.

32. The method of claim 30, wherein the ocular disease or condition is presbyopia.

33. A method for treating or preventing an ocular disease or condition, comprising dissolving the phentolamine mesylate of claim 2 in a pharmaceutically acceptable aqueous carrier or vehicle to provide an ophthalmic solution and administering to a subject in need thereof an effective amount of the ophthalmic solution.

34. The method of claim 33, wherein the ocular disease or condition is a dim or night vision disturbance.

35. The method of claim 33, wherein the ocular disease or condition is presbyopia.

36. A method for treating or preventing an ocular disease or condition, comprising dissolving the phentolamine mesylate of claim 3 in a pharmaceutically acceptable aqueous carrier or vehicle to provide an ophthalmic solution and administering to a subject in need thereof an effective amount of the ophthalmic solution.

37. The method of claim 36, wherein the ocular disease or condition is a dim or night vision disturbance.

38. The method of claim 36, wherein the ocular disease or condition is presbyopia.

* * * * *